United States Patent
Hwang et al.

(10) Patent No.: US 10,499,982 B2
(45) Date of Patent: Dec. 10, 2019

(54) CATHETER FOR DENERVATION

(71) Applicant: HANDOK KALOS MEDICAL INC., Seoul (KR)

(72) Inventors: In-Je Hwang, Seongnam-si (KR); Hae-Won Jang, Seoul (KR); Seung-Woo Song, Seoul (KR); Woo-Ick Jang, Seoul (KR)

(73) Assignee: HANDOK KALOS MEDICAL INC., Seoul (KR)

( * ) Notice: Subject to any disclaimer, the term of this patent is extended or adjusted under 35 U.S.C. 154(b) by 662 days.

(21) Appl. No.: 14/763,382

(22) PCT Filed: Feb. 5, 2014

(86) PCT No.: PCT/KR2014/000997
§ 371 (c)(1),
(2) Date: Jul. 24, 2015

(87) PCT Pub. No.: WO2014/123359
PCT Pub. Date: Aug. 14, 2014

(65) Prior Publication Data
US 2015/0351835 A1 Dec. 10, 2015

(30) Foreign Application Priority Data

Feb. 5, 2013 (KR) .................. 10-2013-0013100
Feb. 5, 2013 (KR) .................. 10-2013-0013101
(Continued)

(51) Int. Cl.
*A61B 18/14* (2006.01)
*A61B 18/00* (2006.01)

(52) U.S. Cl.
CPC ............. *A61B 18/1492* (2013.01); *A61B 2018/00404* (2013.01); *A61B 2018/00434* (2013.01);
(Continued)

(58) Field of Classification Search
CPC ...... A61B 18/1492; A61B 2018/00404; A61B 2018/00434; A61B 2018/00511;
(Continued)

(56) References Cited

U.S. PATENT DOCUMENTS 5,465,717 A * 11/1995 Imran .................. A61B 5/0422
600/374
5,722,401 A * 3/1998 Pietroski .............. A61B 5/0422
600/374
(Continued)

FOREIGN PATENT DOCUMENTS

CN 1085416 A 4/1994
CN 1093933 A 10/1994
(Continued)

OTHER PUBLICATIONS

International Search Report for Application No. PCT/KR2014/000997, dated Aug. 7, 2014 (12 pages).

*Primary Examiner* — Jaymi E Della
(74) *Attorney, Agent, or Firm* — Knobbe Martens Olson & Bear LLP

(57) ABSTRACT

A catheter for denervation includes a catheter body extending in one direction to have a proximal end and a distal end and having an inner space formed along the longitudinal direction thereof, a movable member provided at the distal end of the catheter body to be movable along the longitudinal direction of the catheter body, an operating member having a distal end connected to the movable member to move the movable member, a plurality of support members having one end connected to a terminal of the catheter body and the other end connected to the movable member, wherein when the movable member moves to decrease a distance between the terminal of the catheter body and the movable member, at least a partial portion of the plurality of support members is bent so that the bending portion moves away from the catheter body, a plurality of electrodes respectively provided at the bending portion of the plurality of support members to generate heat, and a lead wire respectively electrically connected to the plurality of electrodes to give a power supply path for the plurality of electrodes.

20 Claims, 24 Drawing Sheets

(30) Foreign Application Priority Data

Feb. 5, 2013 (KR) ........................ 10-2013-0013102
Feb. 20, 2013 (KR) ........................ 10-2013-0018085

(52) U.S. Cl.
CPC ............... *A61B 2018/00511* (2013.01); *A61B 2018/00577* (2013.01); *A61B 2018/1465* (2013.01); *A61B 2018/1467* (2013.01)

(58) Field of Classification Search
CPC .. A61B 2018/00577; A61B 2018/1465; A61B 2018/1467
See application file for complete search history.

(56) References Cited

U.S. PATENT DOCUMENTS

| | | | |
|---|---|---|---|
| 5,908,446 A * | 6/1999 | Imran | A61B 5/0422 600/374 |
| 6,056,744 A | 5/2000 | Edwards | |
| 6,066,755 A * | 5/2000 | Koch | A61K 8/90 252/8.81 |
| 2002/0018866 A1 | 2/2002 | Lee et al. | |
| 2006/0058598 A1 * | 3/2006 | Esposito | A61B 18/1492 600/374 |
| 2008/0097424 A1 * | 4/2008 | Wizeman | A61B 18/1492 606/41 |
| 2008/0125772 A1 | 5/2008 | Stone et al. | |
| 2012/0029510 A1 | 2/2012 | Haverkost | |
| 2012/0271139 A1 * | 10/2012 | Kordis | A61B 5/0422 600/375 |
| 2014/0025069 A1 * | 1/2014 | Willard | A61B 18/1492 606/41 |
| 2015/0045789 A1 * | 2/2015 | Edwards | A61B 18/1206 606/41 |

FOREIGN PATENT DOCUMENTS

| | | |
|---|---|---|
| JP | 2010-507403 A | 3/2010 |
| JP | 2010-274012 A | 12/2010 |
| JP | 2012-095853 A | 5/2012 |
| KR | 10-2001-0030589 A | 4/2001 |
| RU | 2324429 C2 | 5/2008 |
| TW | 201223583 A1 | 6/2012 |
| WO | 94/22366 A1 | 10/1994 |
| WO | 00/62699 A2 | 10/2000 |
| WO | 2011/060339 A1 | 5/2011 |

* cited by examiner

[Fig. 1]
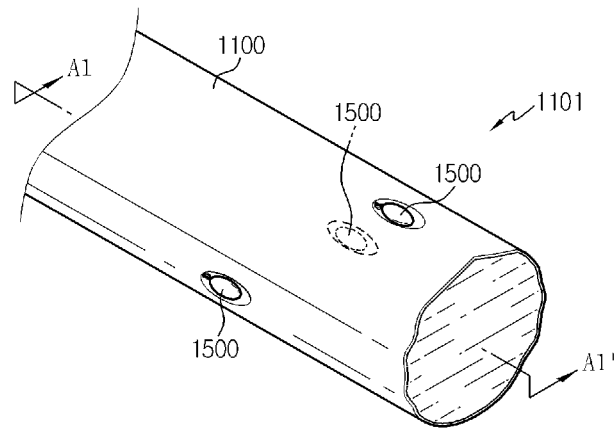
[Fig. 2]
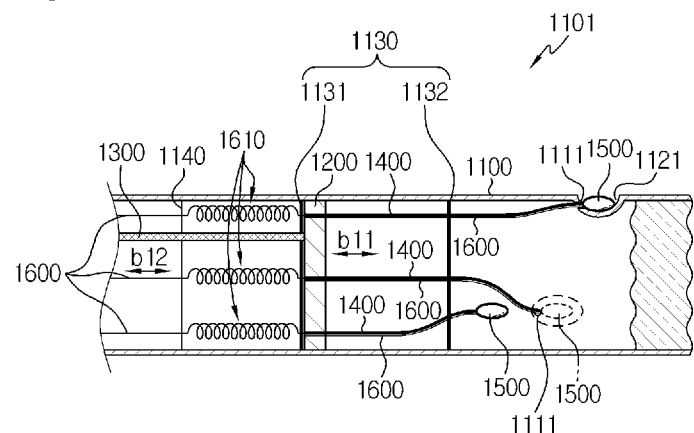
[Fig. 3]
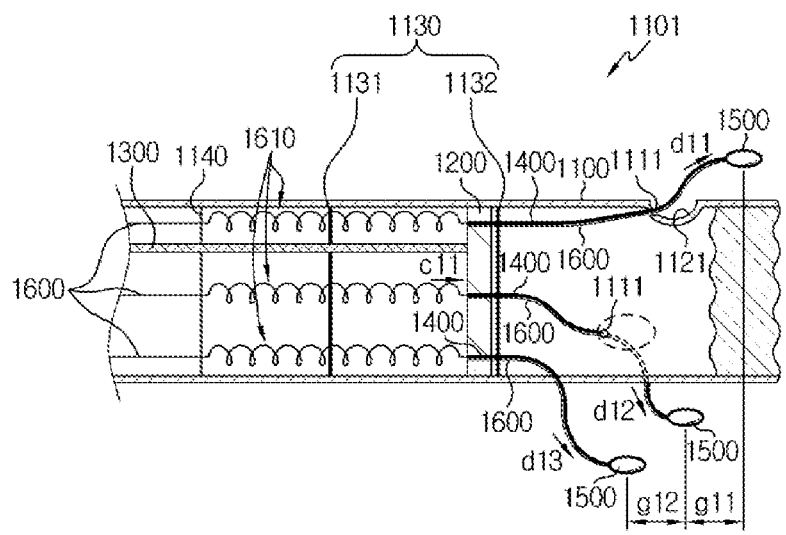

[Fig. 4]
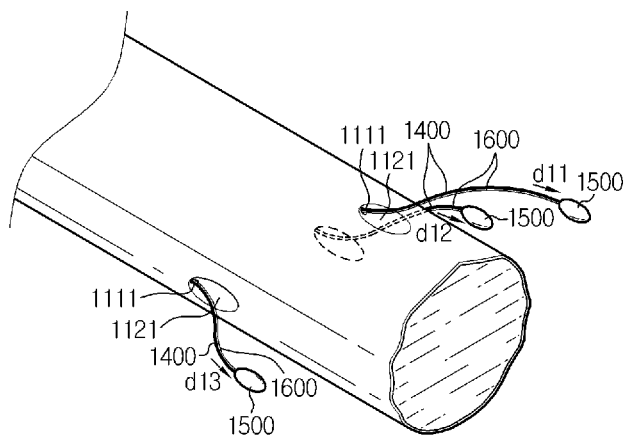
[Fig. 5]
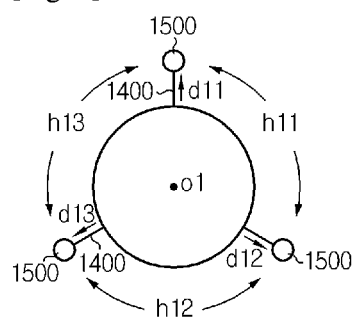
[Fig. 6]
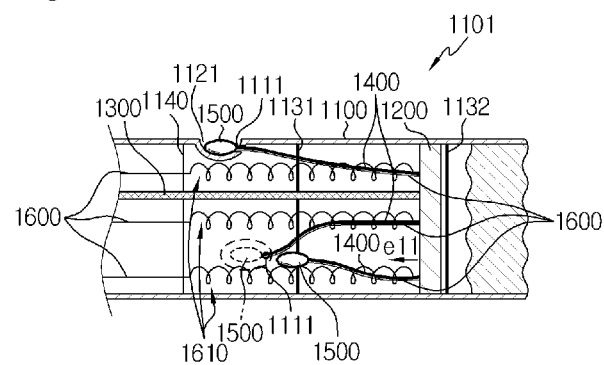
[Fig. 7]
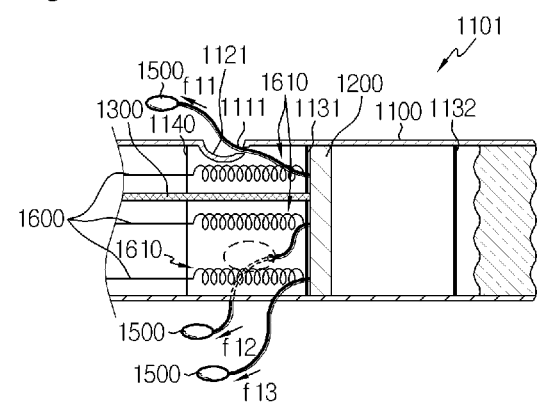

[Fig. 8]
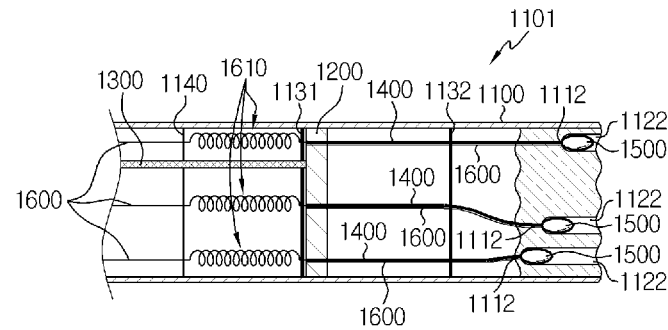
[Fig. 9]
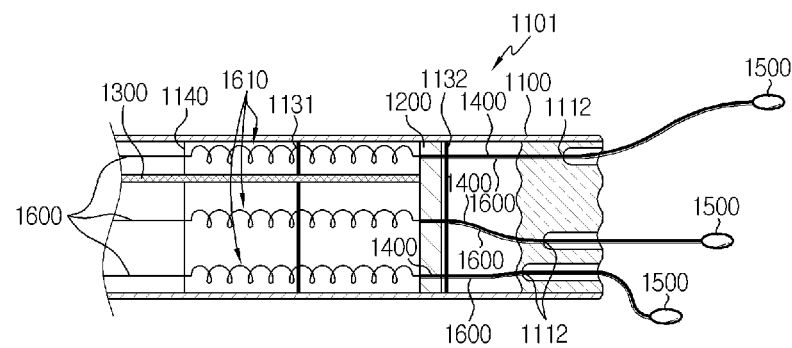
[Fig. 10]
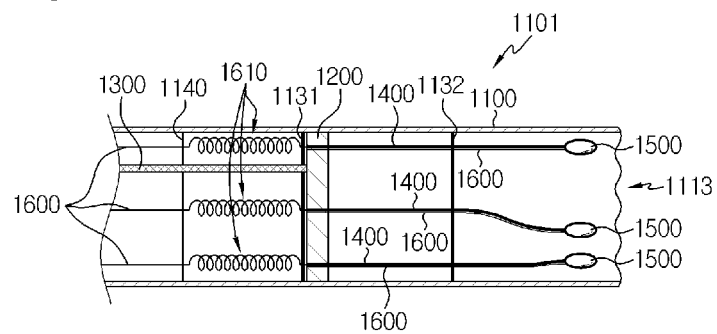
[Fig. 11]
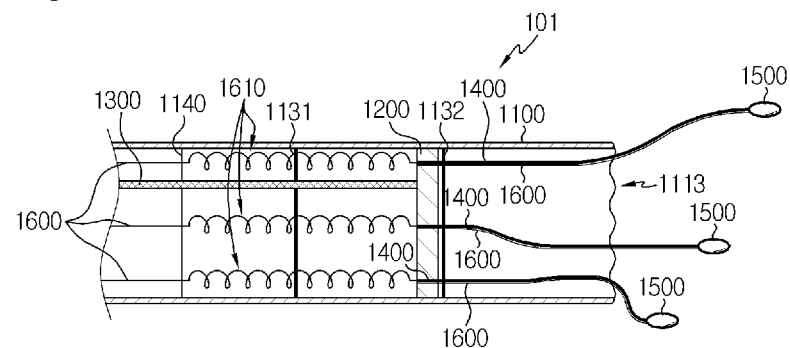

[Fig. 12]
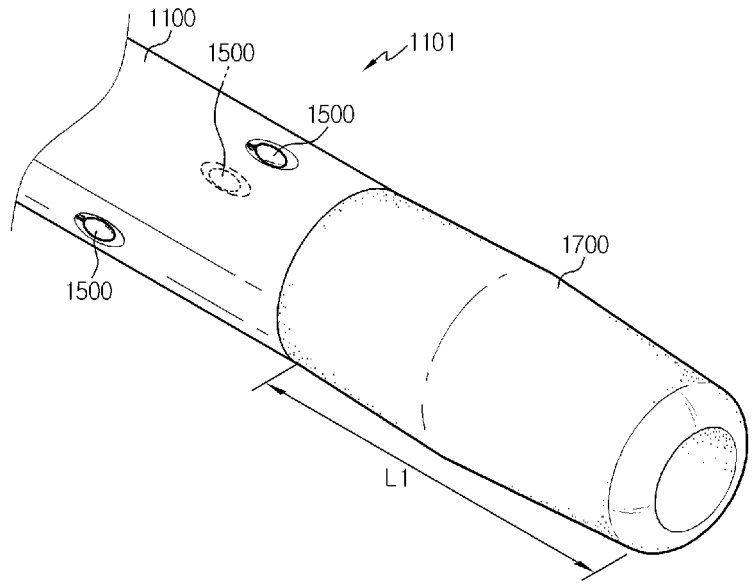
[Fig. 13]
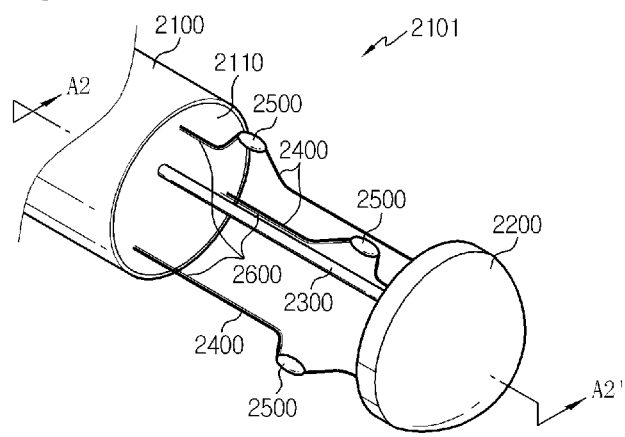
[Fig. 14]
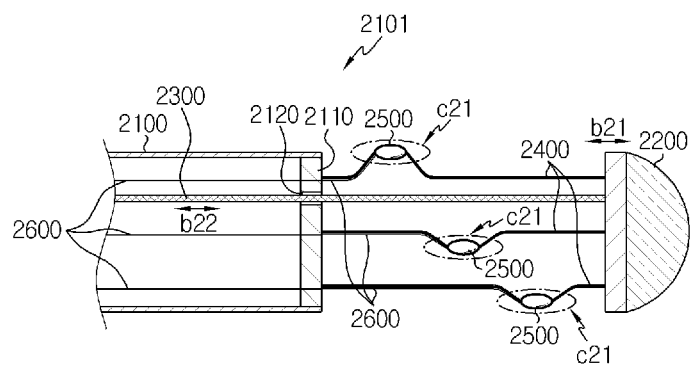

[Fig. 15]
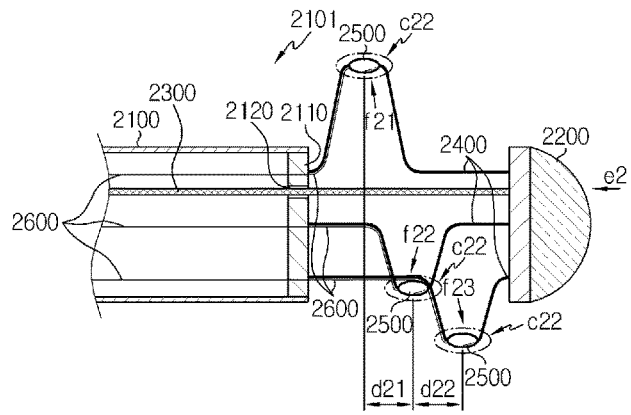
[Fig. 16]
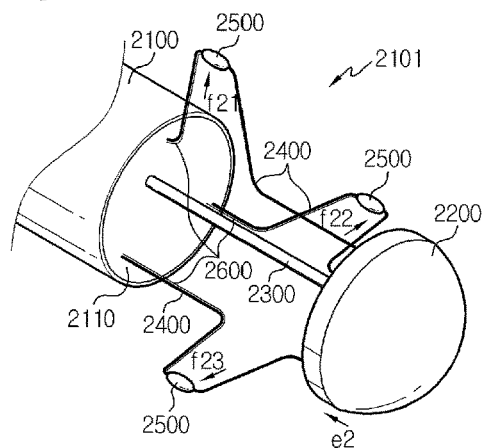
[Fig. 17]
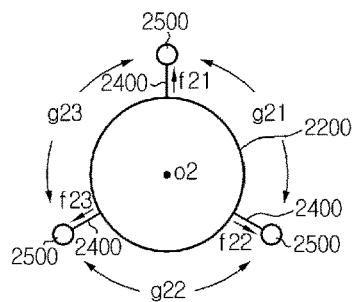
[Fig. 18]
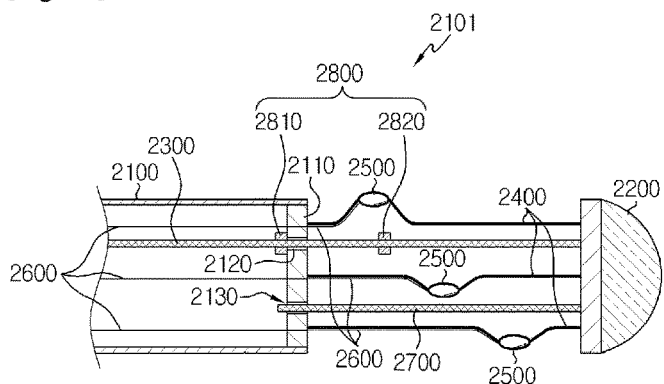

[Fig. 19]
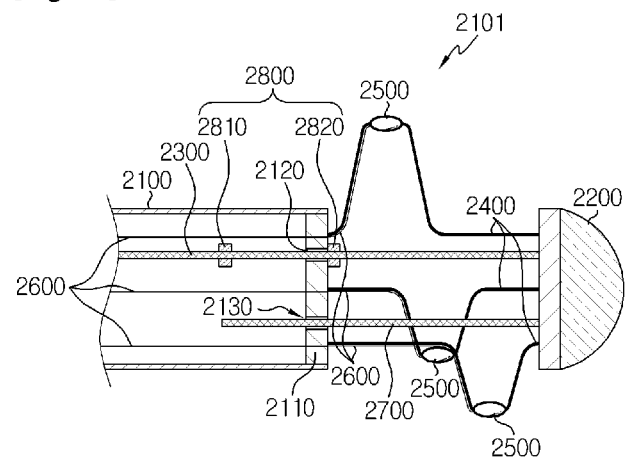
[Fig. 20]
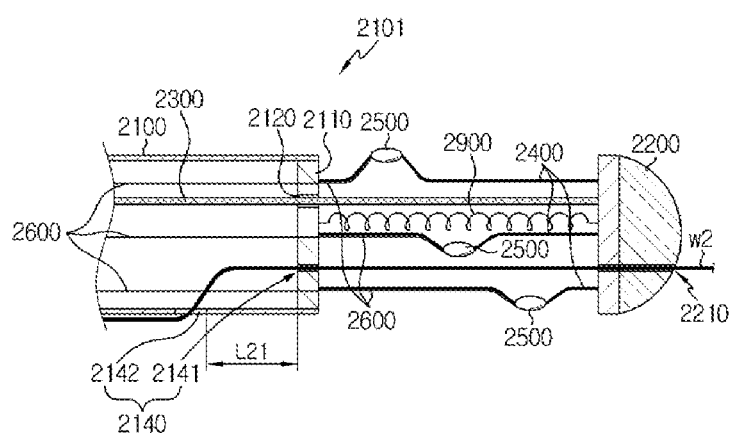
[Fig. 21]
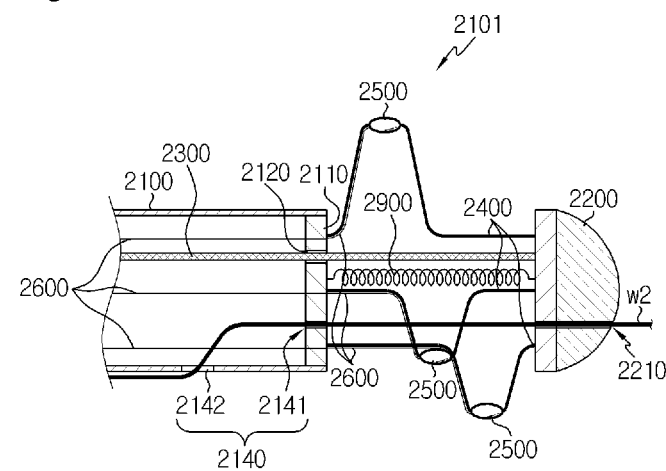

[Fig. 22]
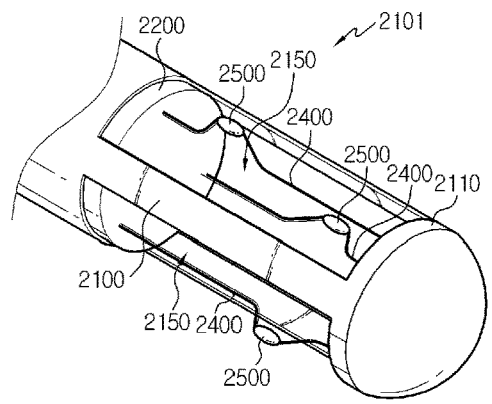
[Fig. 23]
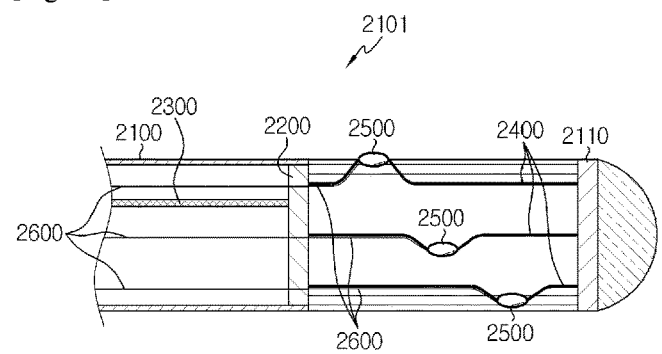
[Fig. 24]
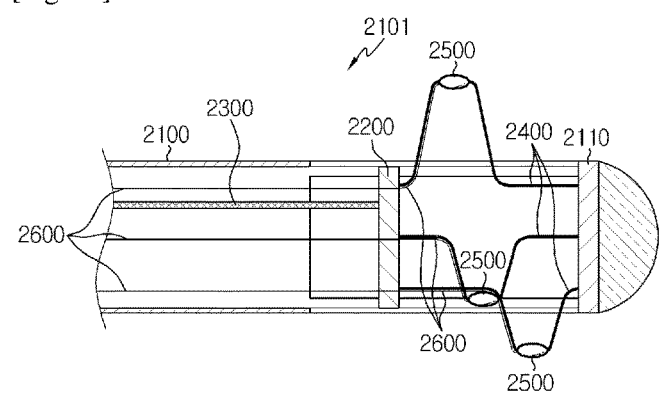
[Fig. 25]
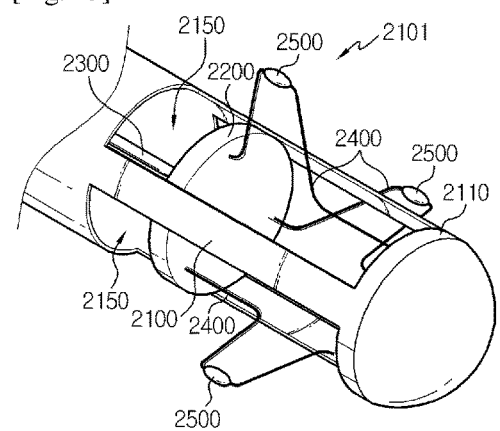

[Fig. 26]
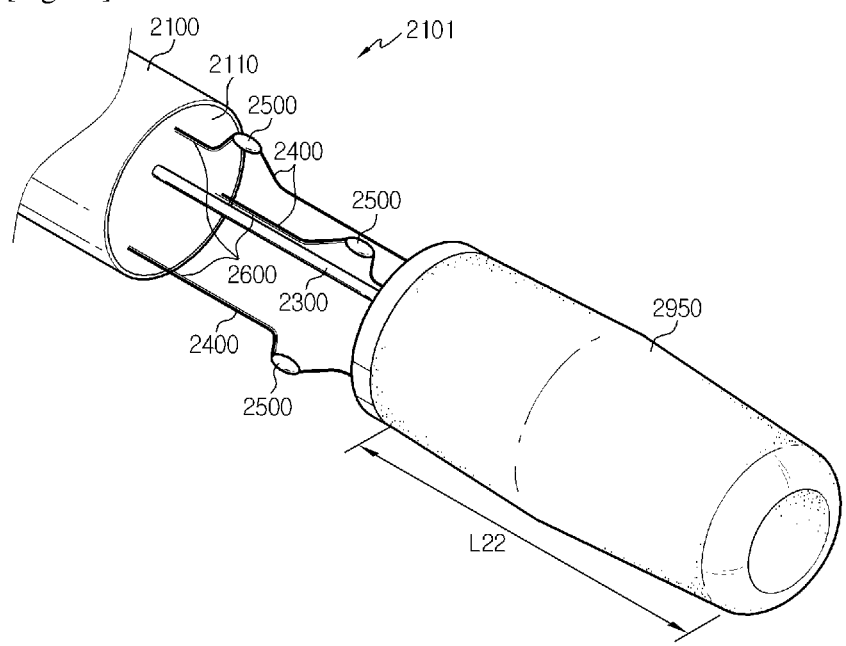
[Fig. 27]
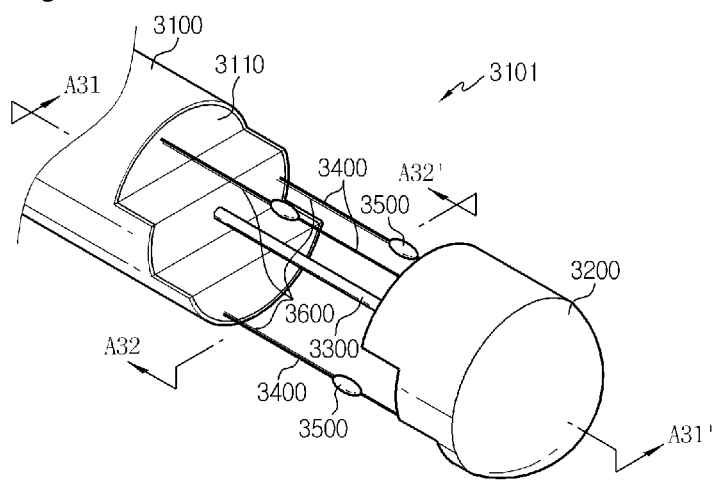
[Fig. 28]
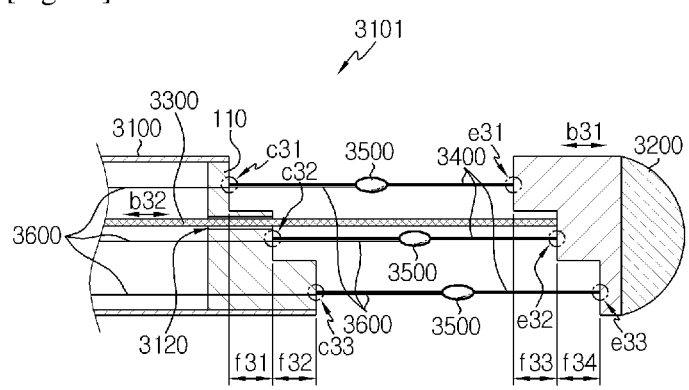

[Fig. 29]
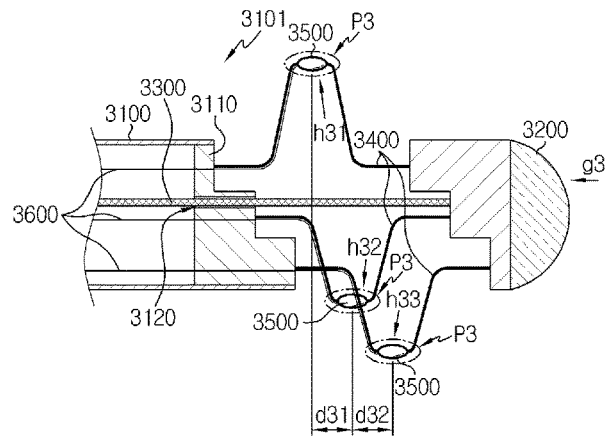
[Fig. 30]
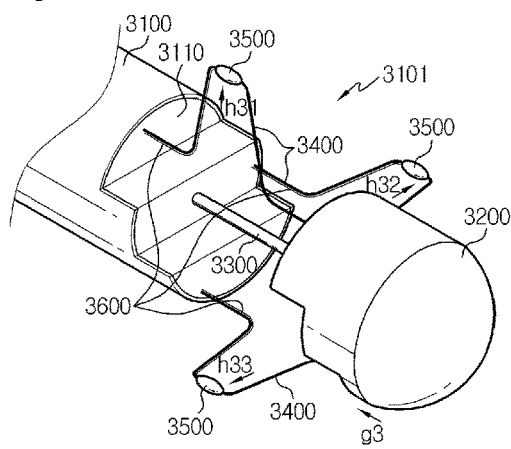
[Fig. 31]
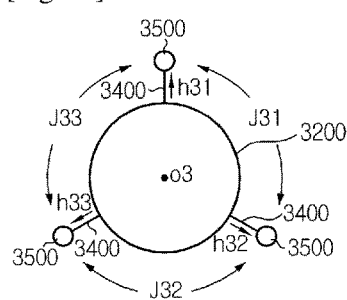
[Fig. 32]
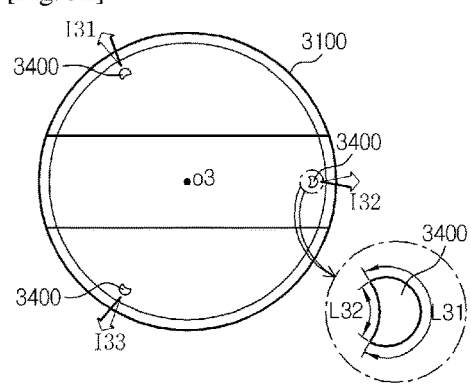

[Fig. 33]
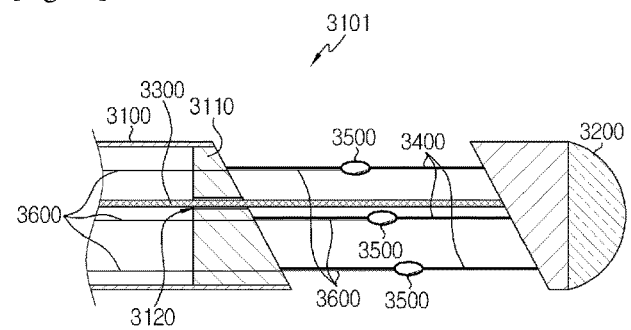
[Fig. 34]
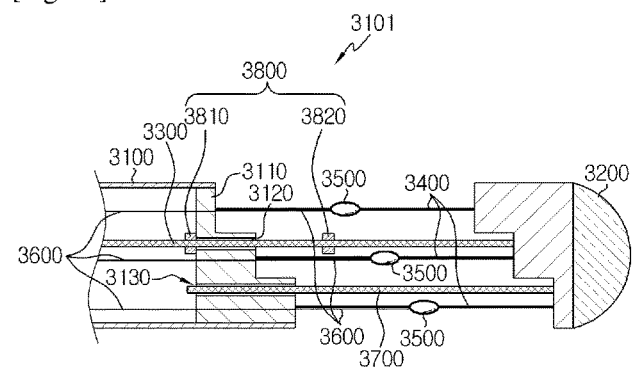
[Fig. 35]
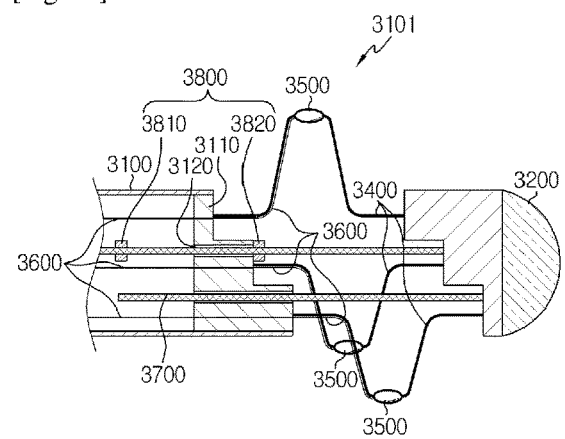
[Fig. 36]
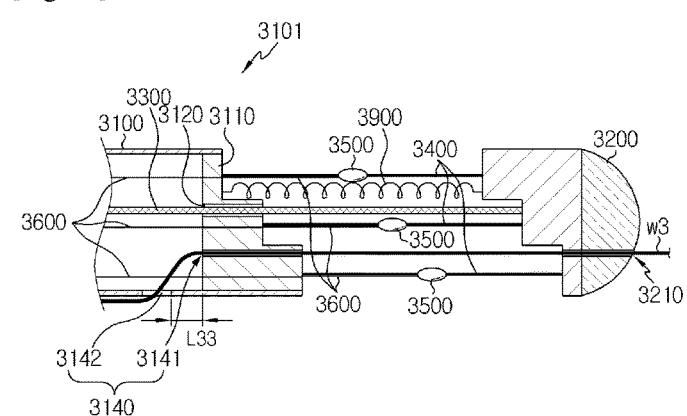

[Fig. 37]
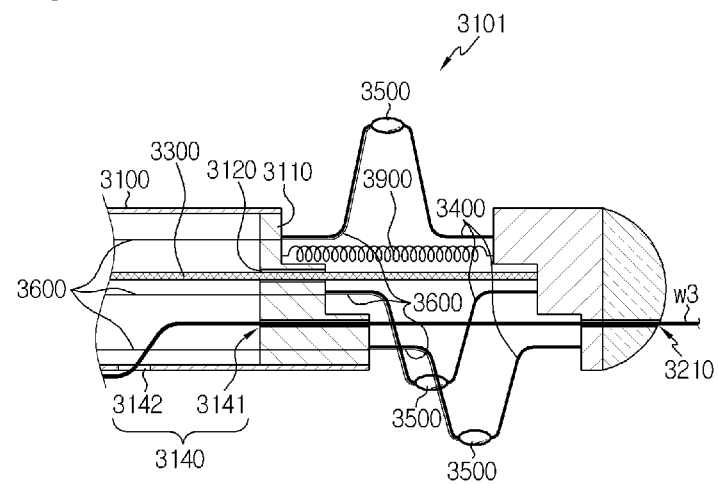
[Fig. 38]
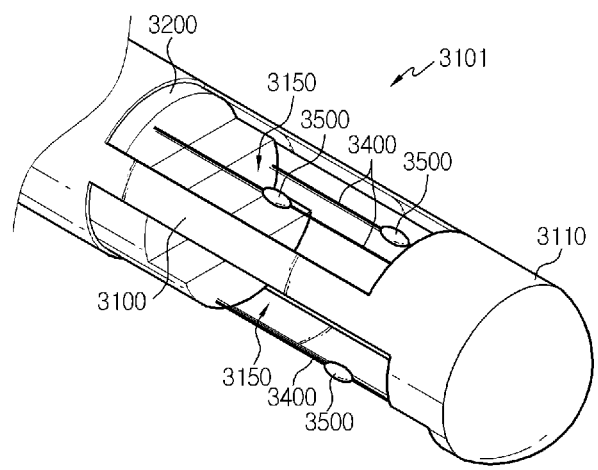
[Fig. 39]
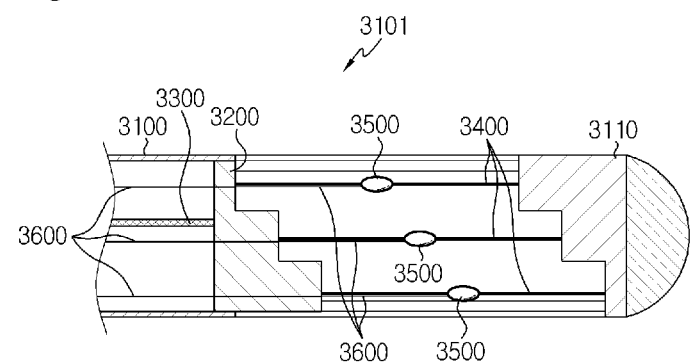

[Fig. 40]
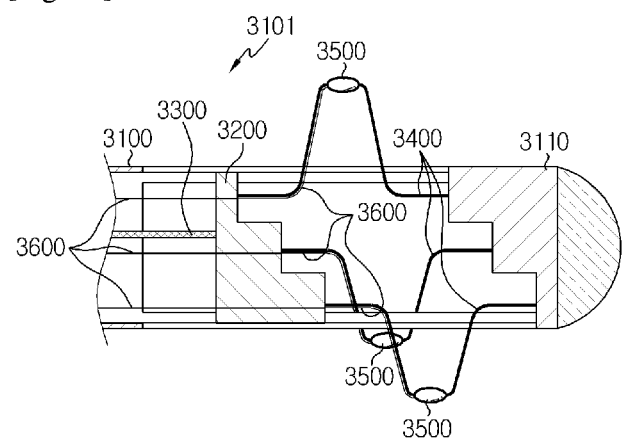
[Fig. 41]
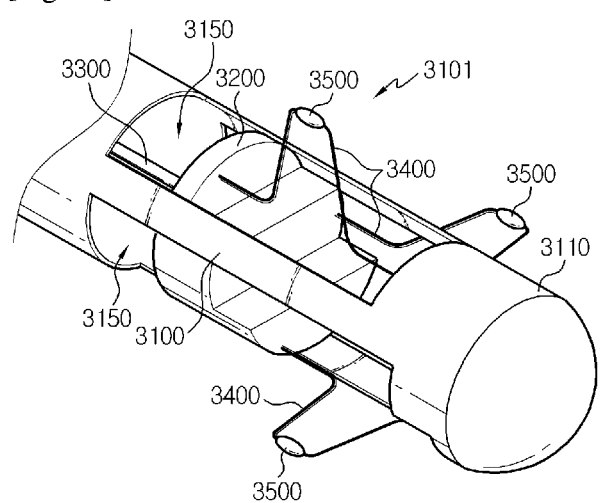

[Fig. 42]
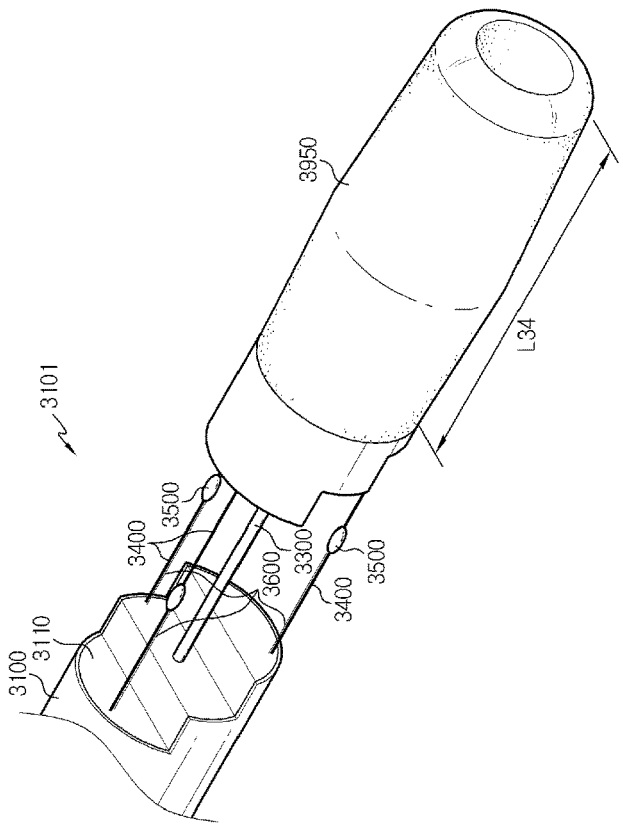
[Fig. 43]
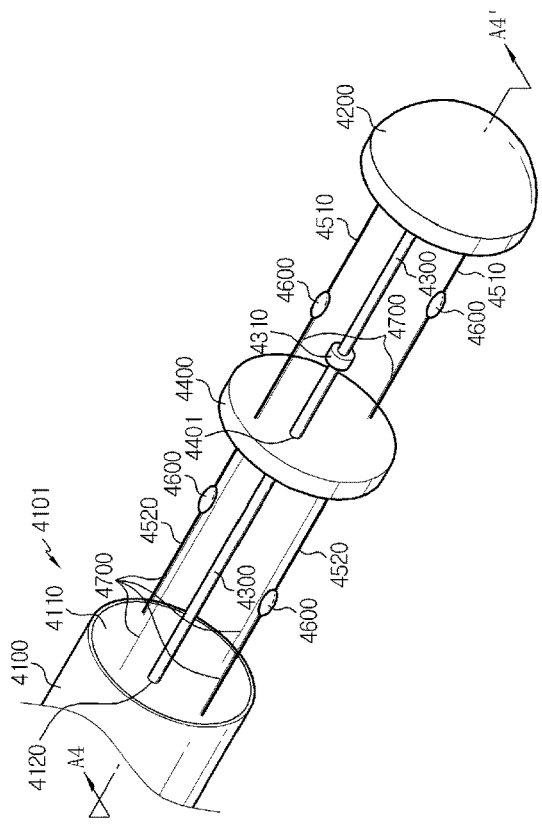

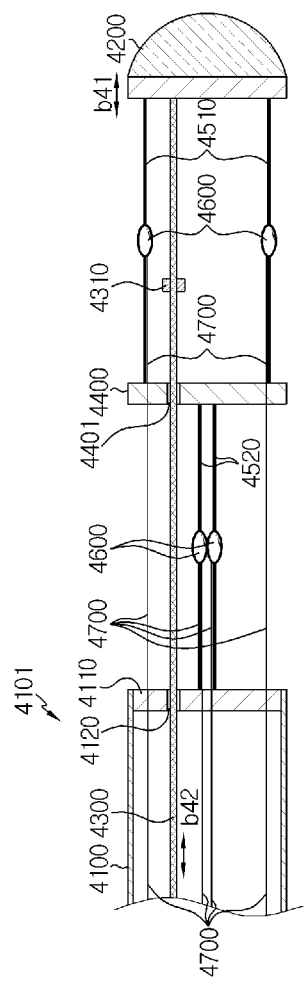

[Fig. 45]
[Fig. 46]
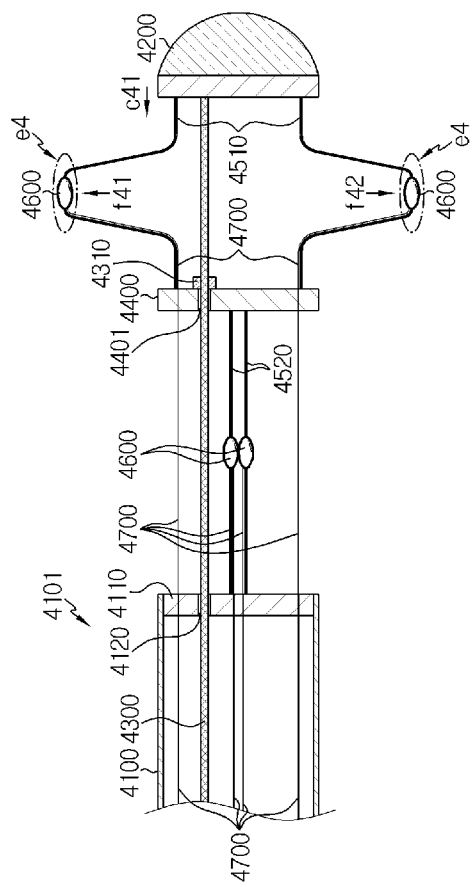
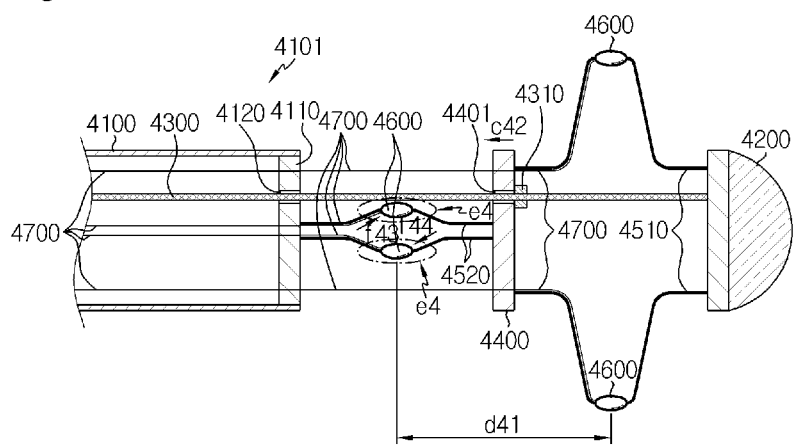

[Fig. 47]
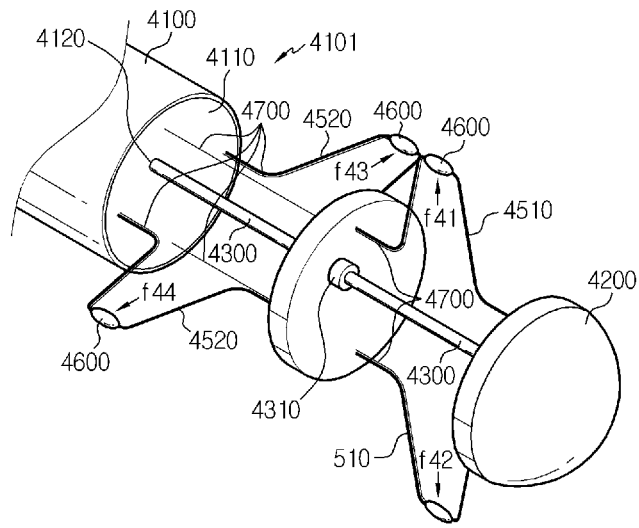
[Fig. 48]
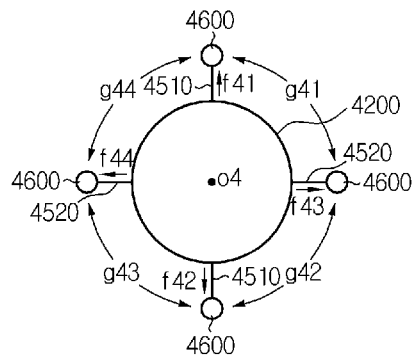
[Fig. 49]
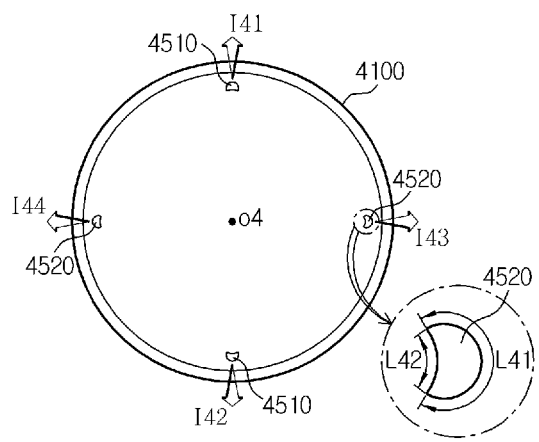

[Fig. 50]
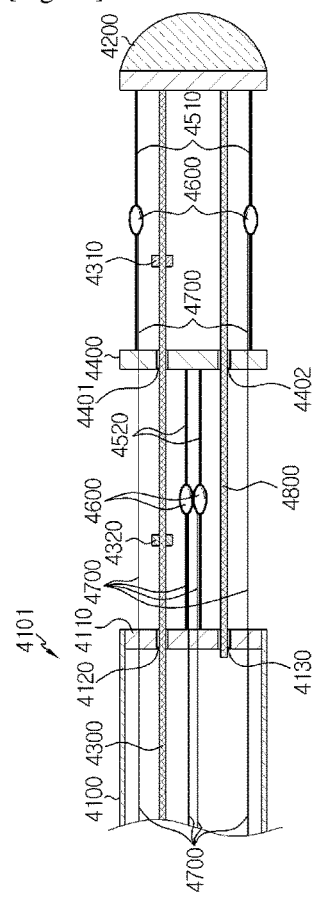
[Fig. 51]
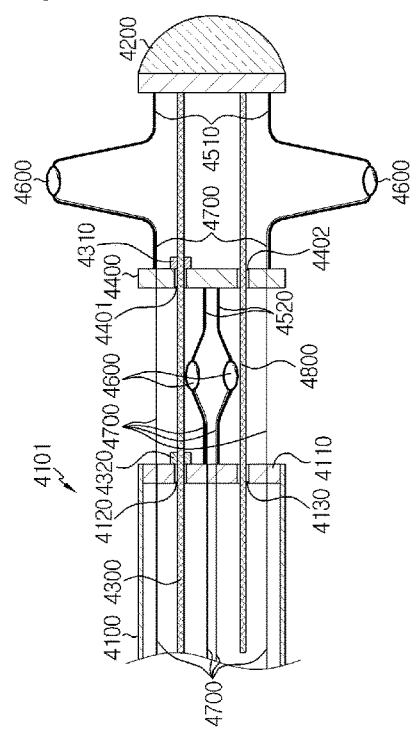

[Fig. 52]
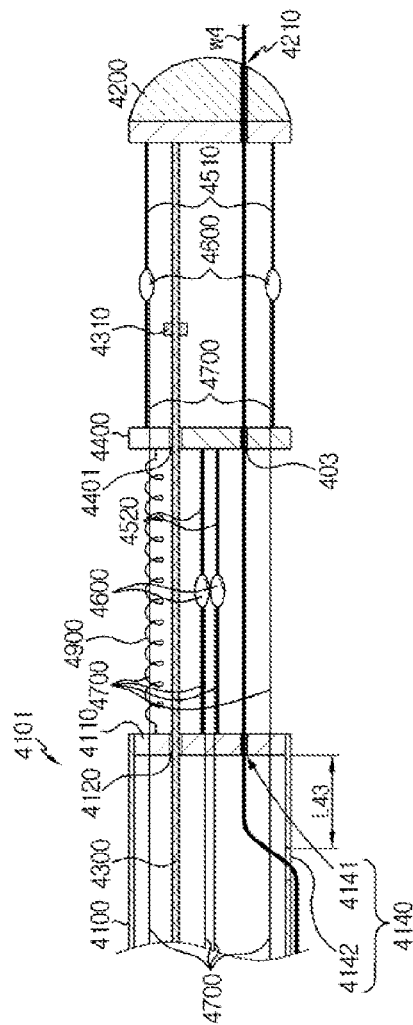

[Fig. 53]
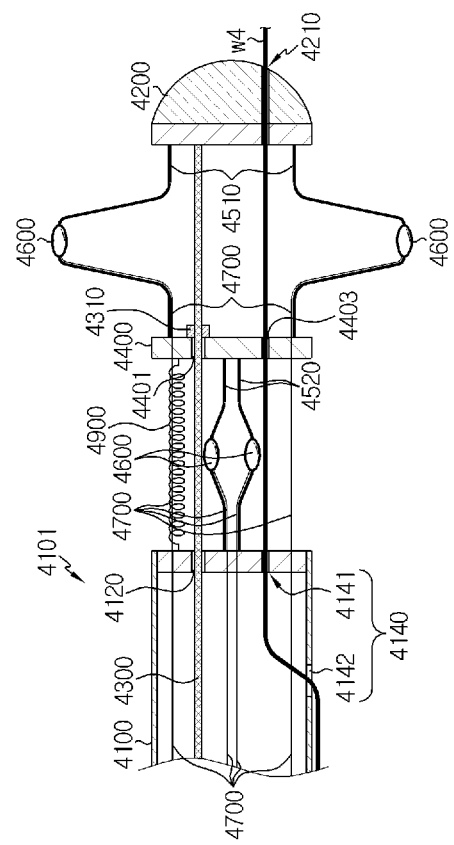

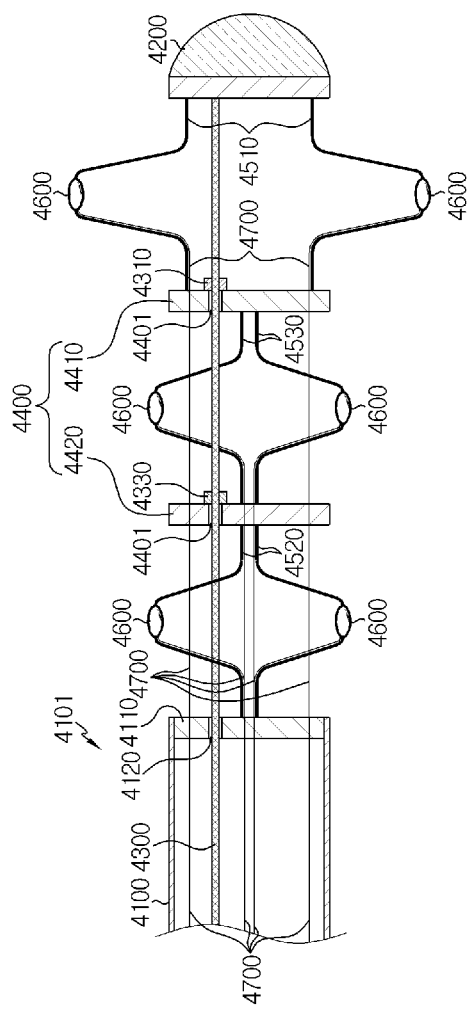
[Fig. 54]

[Fig. 55]
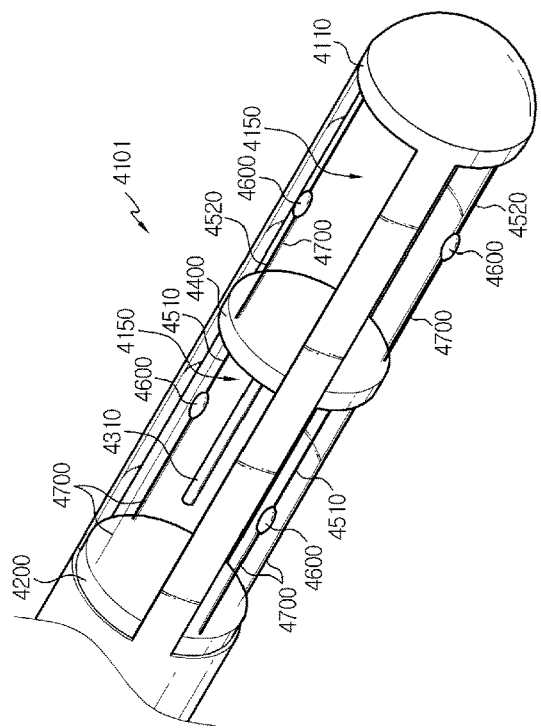
[Fig. 56]
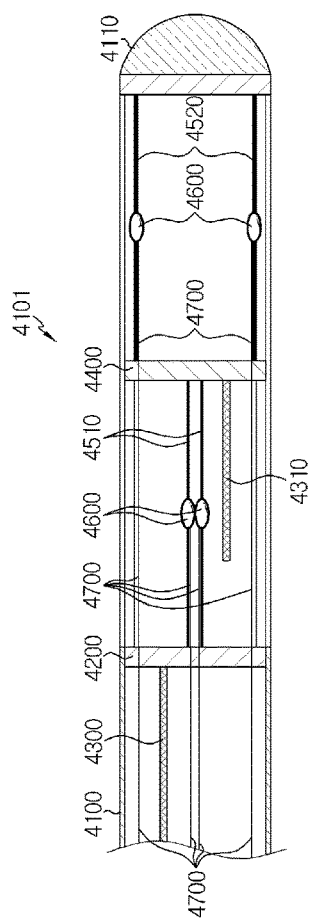

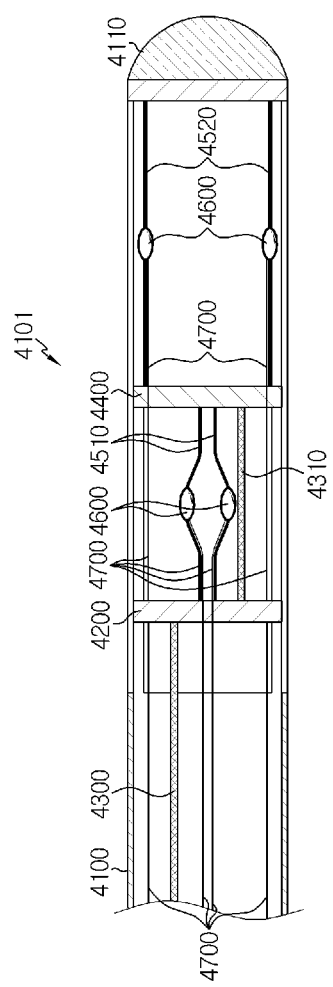
[Fig. 57]

[Fig. 58]
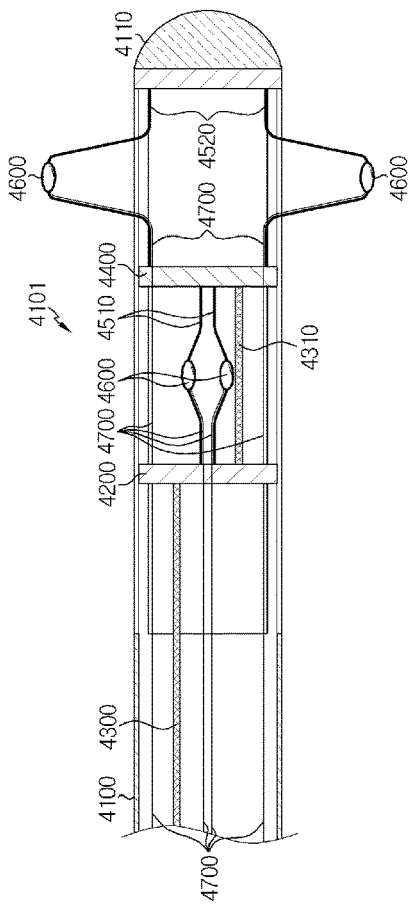
[Fig. 59]
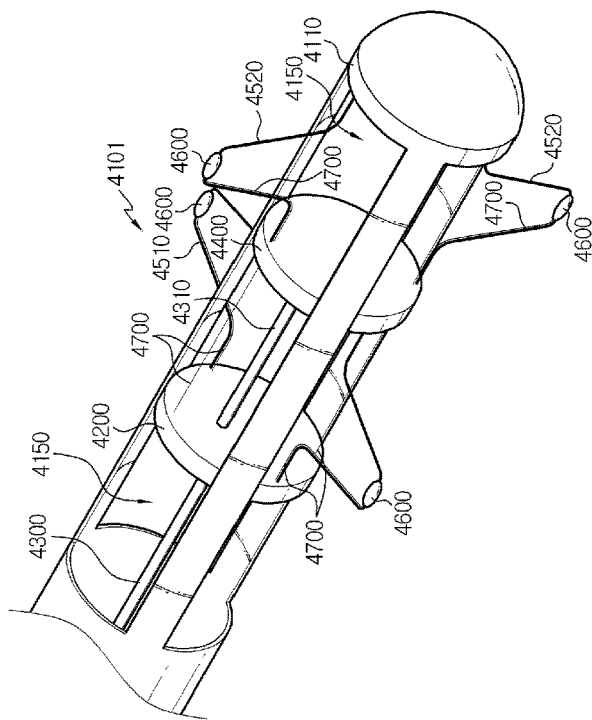

[Fig. 60]
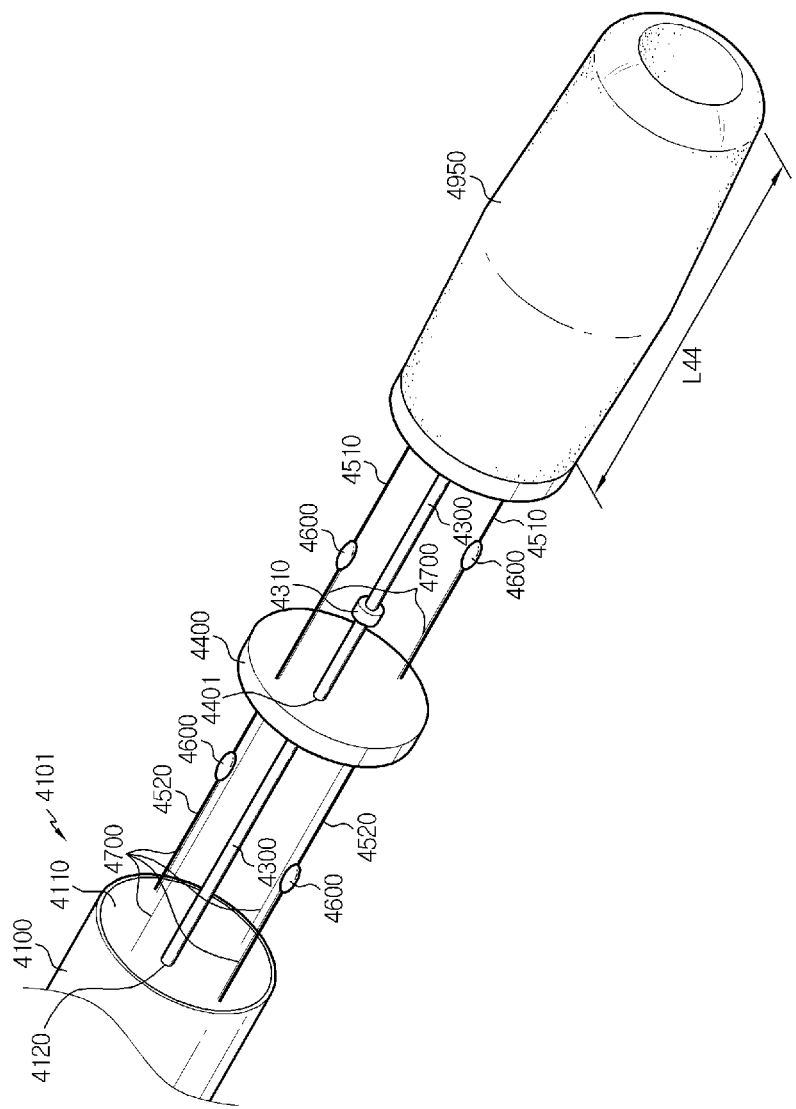

CATHETER FOR DENERVATION

CROSS-REFERENCE TO RELATED APPLICATION

The present application claims priority under 35 U.S.C. § 119 to Korean Patent Application Nos. 10-2013-0013100, 10-2013-0013101 and 10-2013-0013102 filed on Feb. 5, 2013, and Korean Patent Application No. 10-2013-0018085 filed on Feb. 20, 2013 in the Republic of Korea, and under 35 U.S.C. § 365 to PCT/KR2014/000997 filed on Feb. 5, 2014, the disclosures of which are incorporated herein by reference.

TECHNICAL FIELD

The present disclosure relates to a catheter, and more particularly, to a catheter for denervation, which ablates a part of nerves to inactivate nerve conduction, and a denervation apparatus having the catheter.

BACKGROUND ART

Denervation is a surgical procedure for blocking a part of nerve paths for various nerves such as sensory nerves and automatic nerves so that stimulation or information is not delivered. The denervation is being used more and more for treatment of several diseases such as arrhythmia, pain relief, plastic surgery or the like.

In particular, as it has been recently reported that the denervation is available for treatment of hypertension, many endeavors are being made to apply the denervation for effective treatment of hypertension.

In case of hypertension, since blood pressure can be mostly controlled with drugs, most hypertensive patients are depending on drugs until now. However, if blood pressure is lowered with drugs, a hypertensive patient should take the drugs continually, which causes inconvenience and increases costs. In addition, if drugs are taken for a long time, various problems such as damage to internal organs or other side effects. Moreover, some hypertensive patients suffer from intractable hypertension which does not allow easy control of blood pressure with drugs. Since the intractable hypertension is not treated with drugs, the possibility of accidents such as a stroke, an irregular heartbeat, a kidney disease or the like increases. Therefore, the treatment of intractable hypertension is a very serious and urgent issue.

In this circumstance, the denervation attracts attention as an innovative scheme to treat hypertension. In particular, the denervation for treating hypertension may be performed by ablating sympathetic nerves around renal nerves, namely the renal artery, to inactivate nerve conduction so that the renal nerves are blocked. If the renal nerve is activated, the production of renin hormone increases by the kidney, which may cause the increase of blood pressure. Therefore, if the renal nerve is blocked, nerve conduction is not performed, and thus the hypertension may be treated, as proven by various recent experiments.

As described above, a representative renal denervation for treating hypertension is using a catheter. In the denervation using a catheter, a catheter is inserted into a part of a human body, for example the thigh, and a distal end of the catheter is located at the renal artery. In this state, heat is generated at the distal end of the catheter by means of radio frequency (RF) energy or the like to block sympathetic nerves around the renal artery.

If the denervation using a catheter is performed, a very small region is cut in a human body in comparison to the denervation using an abdominal operation. Therefore, latent complications or side effects may greatly decrease, and the time taken for treatment or recovery is very short due to local anesthesia. Therefore, the denervation using a catheter is spotlighted as a next-generation hypertension treatment method due to the above advantages.

However, the denervation using a catheter, particularly the denervation for treating hypertension, is not yet sufficiently developed and thus there is much room for improvement.

In particular, some of catheters which have been proposed for treating denervation include only one electrode to emit energy such as high frequency, and the electrode is located in a blood vessel, for example in the renal artery to block nerves around the blood vessel. However, in this configuration, the electrode may not be positioned at a proper location of the renal nerve, and thus the renal nerve may not be properly blocked. Therefore, in case of such a catheter, the electrode should be located at various locations of the renal artery in order to properly block the renal nerve, which may increase the time for operation and also result in complicated operating procedures.

To solve this problem, it has been recently proposed to dispose a plurality of electrodes at a distal end of a catheter. However, if a plurality of electrodes is disposed in this way, the distal end of the catheter where the electrodes are disposed, namely a catheter tip, has a complicated structure and a great size. If the distal end of the catheter increases as mentioned above, the catheter may not easily move along a blood vessel with a small diameter, like the renal artery, and may also damage the inner wall of the blood vessel. Further, at the present, when a catheter is used, in order to protect organs such as blood vessels and allow easy movement of the catheter to a destination, a tube, called a sheath, is located in an organ such as a blood vessel, and then the catheter is moved through the sheath near to a destination. In this case, if the catheter has a great distal end, the catheter may not be easily moved into the sheath, which may make it difficult to the sheath during an operation.

In addition, some of catheters proposed in the past may cause stenosis since a blood vessel may be narrowed at an ablated region, and some of catheters proposed in the past may also be not easily manipulated.

Moreover, some of catheters proposed in the past may not ensure a proper contact between an electrode and a blood vessel. In this case, thermal energy by the electrode reaching the nerve may not be in a sufficient level, which may not properly block the nerve.

DISCLOSURE

Technical Problem

The present disclosure is designed to solve the problems of the related art, and therefore the present disclosure is directed to providing a catheter for denervation, which may effectively block nerves around a blood vessel by including a plurality of electrodes and also improve a tip structure not to increase a size.

Other objects and advantages of the present disclosure will be understood from the following descriptions and become apparent by the embodiments of the present disclosure. In addition, it is understood that the objects and advantages of the present disclosure may be implemented by components defined in the appended claims or their combinations.

Technical Solution

In a first aspect of the present disclosure, there is provided a catheter for denervation, which includes a catheter body extending in one direction to have a proximal end and a distal end and having an inner space formed along the longitudinal direction thereof; a movable member configured to be movable in the inner space of the catheter body along the longitudinal direction of the catheter body; an operating member having a distal end connected to the movable member to move the movable member; a plurality of support members having one end connected to the movable member and configured so that the other end thereof moves close to or farther from catheter body according to the movement of the movable member; a plurality of electrodes respectively provided at the other end of the plurality of support members to generate heat; and a lead wire respectively electrically connected to the plurality of electrodes to give a power supply path for the plurality of electrodes, the lead wire having a variable region whose length is changeable so that a proximal end of the variable region is fixed to one side of the catheter body and a distal end of the variable region is fixed to the movable member.

Preferably, the catheter body has a plurality of side holes formed in a side surface of the distal end thereof, and the plurality of support members moves through the side holes into or out of the catheter body.

More preferably, the plurality of side holes is located close to the distal end of the catheter body in comparison to the movable member, the movable member is connected to a proximal end of the plurality of support members and the electrode is provided at a distal end of the plurality of support members, respectively, and when the movable member moves in a direction from the proximal end of the catheter body toward the distal end of the catheter body, the electrode moves farther from the catheter body.

Also preferably, the plurality of side holes is located close to the proximal end of the catheter body in comparison to the movable member, the movable member is connected to a distal end of the plurality of support members and the electrode is provided at a proximal end of the plurality of support members, respectively, and when the movable member moves in a direction from the distal end of the catheter body toward the proximal end of the catheter body, the electrode moves farther from the catheter body.

Also preferably, the catheter body has a side insert groove formed in a region where the side hole is formed, the side insert groove being concave toward the inside of the catheter body so that the electrode is inserted therein.

Also preferably, the catheter body has a plurality of front holes formed in a front surface of the distal end thereof, and the plurality of support members moves through the front holes into or out of the catheter body.

Also preferably, the catheter body has an opening formed in a front surface of the distal end thereof, and the plurality of support members and the plurality of electrodes move through the opening to be received in the inner space of the catheter body or to be drawn out of the catheter body.

Also preferably, in a state in which the other end of the support member moves away from the catheter body, the plurality of electrodes is spaced apart from each other by a predetermined distance in the longitudinal direction of the catheter body.

Also preferably, in a state in which the other end of the support member moves away from the catheter body, the plurality of electrodes is spaced apart from each other by 0.3 cm to 0.8 cm in the longitudinal direction of the catheter body.

Also preferably, the plurality of electrodes generates heat by means of radio frequency.

Also preferably, the support member is pre-shaped so that the other end thereof moves away from the catheter body according to the movement of the movable member.

Also preferably, the catheter body includes at least one stopper provided in the inner space to limit a moving distance of the movable member.

Also preferably, the catheter body has a guide hole formed in the distal end so that a guide wire moves therethrough.

Also preferably, the catheter for denervation may further include an elastic member connected between the catheter body and the movable member.

In another aspect, there is also provided a denervation apparatus which includes the catheter for denervation according to the first aspect of the present disclosure.

In a second aspect of the present disclosure, there is provided a catheter for denervation, which includes a catheter body extending in one direction to have a proximal end and a distal end and having an inner space formed along the longitudinal direction thereof; a movable member provided at the distal end of the catheter body to be movable along the longitudinal direction of the catheter body; an operating member having a distal end connected to the movable member to move the movable member; a plurality of support members having one end connected to a terminal of the catheter body and the other end connected to the movable member, wherein when the movable member moves to decrease a distance between the terminal of the catheter body and the movable member, at least a partial portion of the plurality of support members is bent so that the bending portion moves away from the catheter body; a plurality of electrodes respectively provided at the bending portion of the plurality of support members to generate heat; and a lead wire respectively electrically connected to the plurality of electrodes to give a power supply path for the plurality of electrodes.

Preferably, the movable member is provided out of the catheter body.

More preferably, the catheter according to the second aspect of the present disclosure may further include a reinforcing member extending in the longitudinal direction of the catheter body and provided between the catheter body and the movable member, wherein a distal end of the reinforcing member is fixed to the movable member and a proximal end of the reinforcing member is inserted into a through hole of the catheter body, so that the proximal end of the reinforcing member moves through the through hole of the catheter body according to the movement of the movable member.

Also preferably, the movable member is provided in the inner space of the catheter body, and the catheter body has an opening through which the bending portion of the support member is drawn out of the catheter body when the support member is bent.

Also preferably, in a state in which the bending portion of the support member moves away from the catheter body, the plurality of electrodes is spaced apart from each other by a predetermined distance in the longitudinal direction of the catheter body.

Also preferably, in a state in which the bending portion of the support member moves away from the catheter body, the plurality of electrodes is spaced apart from each other by 0.3 cm to 0.8 cm in the longitudinal direction of the catheter body.

Also preferably, the surfaces of the catheter body and the movable member connected to the support member are perpendicular to the longitudinal direction of the catheter body.

Also preferably, the plurality of electrodes generates heat by means of radio frequency.

Also preferably, the catheter body has a guide hole formed in the distal end so that a guide wire moves therethrough.

Also preferably, the catheter according to the present disclosure may further include at least one stopper for limiting a moving distance of the movable member.

Also preferably, the catheter according to the present disclosure may further include an elastic member connected to the movable member to give a restoring force with respect to the movement of the movable member.

In another aspect, there is also provided a denervation apparatus which includes the catheter for denervation according to the second aspect of the present disclosure.

In a third aspect of the present disclosure, there is provided a catheter for denervation, which includes a catheter body extending in one direction to have a proximal end and a distal end and having an inner space formed along the longitudinal direction thereof; a movable member provided at the distal end of the catheter body to be movable along the longitudinal direction of the catheter body; an operating member having a distal end connected to the movable member to move the movable member; a plurality of support members having one end connected to a terminal of the catheter body and the other end connected to the movable member, wherein when the movable member moves to decrease a distance between the terminal of the catheter body and the movable member, at least a partial portion of the plurality of support members is bent so that the bending portion moves away from the catheter body; a plurality of electrodes respectively provided at the bending portion of the plurality of support members to generate heat; and a lead wire respectively electrically connected to the plurality of electrodes to give a power supply path for the plurality of electrodes, wherein at least one of the catheter body and the movable member is connected to at least two support members at points which are spaced apart from each other by a predetermined distance in the longitudinal direction of the catheter body.

Preferably, at least one of the catheter body and the movable member has a step formed at a surface thereof which is connected to the support member.

Also preferably, at least one of the catheter body and the movable member is inclined at a surface thereof which is connected to the support member.

Also preferably, the movable member is provided out of the catheter body.

More preferably, the catheter for denervation according to the third aspect of the present disclosure may further include a reinforcing member extending in the longitudinal direction of the catheter body and provided between the catheter body and the movable member, wherein a distal end of the reinforcing member is fixed to the movable member and a proximal end of the reinforcing member is inserted into a through hole of the catheter body, so that the proximal end of the reinforcing member moves through the through hole of the catheter body according to the movement of the movable member.

Also preferably, the movable member is provided in the inner space of the catheter body, and the catheter body has an opening through which the bending portion of the support member is drawn out of the catheter body when the support member is bent.

Also preferably, the surface of the catheter body and the surface of the movable member, which are connected to the support member, are matched with each other.

Also preferably, in a state in which the bending portion of the support member moves away from the catheter body, the plurality of electrodes is spaced apart from each other by 0.3 cm to 0.8 cm in the longitudinal direction of the catheter body.

Also preferably, a section of the support member in the width direction has an outer surface length longer than an inner surface length thereof.

Also preferably, the support member has a curved portion formed so that the bending portion has a bending direction to move away from the catheter body.

Also preferably, the support member is pre-shaped so that the bending portion has a bending direction to move away from the catheter body.

Also preferably, in a state in which the bending portion of the support member moves away from the catheter body, the plurality of electrodes is spaced apart from each other by a predetermined angle based on a central axis of the catheter body in the longitudinal direction.

Also preferably, the plurality of electrodes generates heat by means of radio frequency.

Also preferably, the catheter body has a guide hole formed in the distal end so that a guide wire moves therethrough.

Also preferably, the catheter for denervation according to the present disclosure may further include at least one stopper for limiting a moving distance of the movable member.

Also preferably, the catheter for denervation according to the present disclosure may further include an elastic member connected to the movable member to give a restoring force with respect to the movement of the movable member.

In another aspect, there is also provided a denervation apparatus which includes the catheter for denervation according to the third aspect of the present disclosure.

In a fourth aspect of the present disclosure, there is provided a catheter for denervation, which includes a catheter body extending in one direction to have a proximal end and a distal end and having an inner space formed along the longitudinal direction thereof; a movable member provided at the distal end of the catheter body to be movable along the longitudinal direction of the catheter body; an operating member having a distal end connected to the movable member to move the movable member; an intermediate member provided between a terminal of the catheter body and the movable member to be movable along the longitudinal direction of the catheter body; a first stopper for allowing the intermediate member to move by the operating member when a distance between the movable member and the intermediate member decreases to a predetermined level; a first support member having one end connected to the intermediate member and the other end connected to the movable member, wherein when the movable member moves to decrease the distance between the intermediate member and the movable member, at least a partial portion of the first support member is bent so that the bending portion moves away from the catheter body; a second support member having one end connected to the terminal of the catheter body and the other end connected to the intermediate member, wherein when the intermediate member moves to decrease the distance between the intermediate member and the terminal of the catheter body, at least a partial portion of the second support member is bent so that the bending portion moves away from the catheter body; a plurality of electrodes respectively provided at the bending portions of the first support member and the second support member to generate heat; and a lead wire respectively electrically connected to the plurality of electrodes to give a power supply path for the plurality of electrodes.

Preferably, the movable member and the intermediate member are provided out of the catheter body, and the intermediate member has an insert hole through which the operating member is inserted.

Also preferably, the movable member and the intermediate member are provided in the catheter body, and the catheter body has an opening through which the bending portions of the first support member and the second support member are drawn out of the catheter body when the first support member and the second support member are bent.

Also preferably, in a state in which the bending portions of the first support member and the second support member move away from the catheter body, the electrodes provided at the first support member and the second support member are spaced apart from each other by 0.3 cm to 0.8 cm in the longitudinal direction of the catheter body.

Also preferably, sections of the first support member and the second support member in the width direction have an outer surface length longer than an inner surface length thereof.

Also preferably, the first support member and the second support member have a curved portion formed so that the bending portion has a bending direction to move away from the catheter body.

Also preferably, the first support member and the second support member are pre-shaped so that the bending portion has a bending direction to move away from the catheter body.

Also preferably, in a state in which the bending portions of the first support member and the second support member moves away from the catheter body, the plurality of electrodes is spaced apart from each other by a predetermined angle based on a central axis of the catheter body in the longitudinal direction.

Also preferably, the first support member and the second support member respectively include a plurality of unit support members.

Also preferably, the intermediate member includes a plurality of unit intermediate members, the catheter further comprises a third support member having both ends connected to the plurality of unit intermediate members, wherein when a distance between the plurality of unit intermediate members decreases, at least a partial portion of the third support member is bent so that the bending portion moves away from the catheter body, wherein an electrode is provided at the bending portion.

Also preferably, the plurality of electrodes generates heat by means of radio frequency.

Also preferably, the catheter body has a guide hole formed in the distal end so that a guide wire moves therethrough.

Also preferably, the first stopper is provided at the operating member between the movable member and the intermediate member to be hooked by an insert hole of the intermediate member through which the operating member is inserted.

Also preferably, the catheter according to the present disclosure may further include a second stopper provide at the operating member between the intermediate member and the terminal of the catheter body to be hooked by an operation hole of the catheter body through which the operating member is inserted.

Also preferably, the catheter according to the present disclosure may further include an elastic member connected to the intermediate member to give a restoring force with respect to the movement of the intermediate member.

In another aspect, there is also provided a denervation apparatus which includes the catheter for denervation according to the fourth aspect of the present disclosure.

Advantageous Effects

According to the present disclosure, since a plurality of electrodes is provided at a distal end of a catheter body, it is possible to effectively block nerves around a blood vessel.

In particular, according to an embodiment of the present disclosure, the plurality of electrodes is inclined with a predetermined angle based on a central axis of the catheter body to be disposed widely in 360° directions along the inner circumference of the blood vessel, which makes it possible to ablate nerves around the blood vessel to the maximum.

In addition, according to an embodiment of the present disclosure, the plurality of electrodes are not located on a single section of the blood vessel but spaced from each other in the longitudinal direction of the blood vessel, which may prevent stenosis from being generated due to ablation.

Moreover, according to the present disclosure, a distal end of the catheter body, namely a catheter tip, may not have a complicated structure and a large size. Therefore, the catheter tip may easily move through a blood vessel with a small diameter, and it is also possible to prevent a wall of the blood vessel from being damaged by a moving catheter. Moreover, the present disclosure may be very easily applied to an operation in which a separate component such as a sheath is inserted into the blood vessel and then the catheter is inserted into the sheath, without directly inserting the catheter into a blood vessel, it is possible insert.

In addition, according to an embodiment of the present disclosure, a lead wire connected to the electrodes to supply electric energy to the electrodes is partially formed with a coil shape near the distal end. Therefore, the length of the lead wire may be easily adjusted due to the portion with such a coil shape, and it is not needed to move the entire lead wire through the catheter body.

Moreover, according to the present disclosure, since the electrodes are inserted into the catheter body, it is possible to prevent or minimize protrusion of the electrodes out of the outer surface of the catheter body. Therefore, when the distal end of the catheter moves through the blood vessel, it is possible to prevent the inner wall of the blood vessel from being damaged by the electrodes.

Meanwhile, the present disclosure may be widely used for treating various diseases or relieving pain by using a catheter, and particularly, the present invention may be more effectively applied to medical operations for treating hypertension by blocking sympathetic nerves around a renal artery.

DESCRIPTION OF DRAWINGS

The accompanying drawings illustrate preferred embodiments of the present disclosure and, together with the foregoing disclosure, serve to provide further understanding of the technical spirit of the present disclosure. However, the present disclosure is not to be construed as being limited to the drawings. In the drawings:

FIG. 1 is a perspective view schematically showing a distal end of a catheter according to a first aspect of the present disclosure;

FIG. 2 is a cross-sectional view, taken along the line A1-A1' of FIG. 1;

FIG. 3 is a cross-sectional view schematically showing that a support member whose one end is connected to a movable member has the other end moving away from a catheter body by the movement of the movable member, in the configuration of FIG. 2;

FIG. 4 is a perspective view of FIG. 3;

FIG. 5 is a front view of FIG. 3;

FIG. 6 is a cross-sectional view showing a distal end of a catheter for denervation according to another embodiment of the present disclosure;

FIG. 7 is a schematic diagram showing that an electrode moves away from the catheter body by the movement of the movable member, in the configuration of FIG. 6;

FIG. 8 is a cross-sectional view schematically showing a distal end of a catheter for denervation according to another embodiment of the present disclosure;

FIG. 9 is a schematic diagram showing that an electrode moves away from the catheter body by the movement of the movable member, in the configuration of FIG. 8;

FIG. 10 is a cross-sectional view schematically showing a distal end of a catheter for denervation according to another embodiment of the present disclosure;

FIG. 11 is a schematic diagram showing that an electrode moves away from the catheter body by the movement of the movable member, in the configuration of FIG. 10;

FIG. 12 is a perspective view schematically showing a distal end of a catheter for denervation according to another embodiment of the present disclosure;

FIG. 13 is a perspective view schematically showing a distal end of a catheter according to a second aspect of the present disclosure;

FIG. 14 is a cross-sectional view, taken along the line A2-A2' of FIG. 13;

FIG. 15 a cross-sectional view schematically showing that an electrode moves away from the catheter body by the movement of the movable member, in the configuration of FIG. 14;

FIG. 16 is a perspective view of FIG. 15;

FIG. 17 is a front view of FIG. 16;

FIG. 18 is a cross-sectional view schematically showing a distal end of a catheter for denervation according to another embodiment of the present disclosure;

FIG. 19 is a cross-sectional view schematically showing that an electrode moves away from the catheter body by the movement of the movable member, in the configuration of FIG. 18;

FIG. 20 is a cross-sectional view schematically showing a distal end of a catheter for denervation according to another embodiment of the present disclosure;

FIG. 21 is a cross-sectional view schematically showing that an electrode moves away from the catheter body by the movement of the movable member, in the configuration of FIG. 20;

FIG. 22 is a cross-sectional view schematically showing a distal end of a catheter for denervation according to another embodiment of the present disclosure;

FIG. 23 is a cross-sectional view showing the catheter of FIG. 22 along the longitudinal direction;

FIG. 24 is a cross-sectional view schematically showing that an electrode moves away from the catheter body by the movement of the movable member, in the configuration of FIG. 23;

FIG. 25 is a perspective view of FIG. 24;

FIG. 26 is a perspective view schematically showing a distal end of a catheter for denervation according to another embodiment of the present disclosure;

FIG. 27 is a perspective view schematically showing a distal end of a catheter according to a third aspect of the present disclosure;

FIG. 28 is a cross-sectional view, taken along the line A31-A31' of FIG. 27;

FIG. 29 is a cross-sectional view schematically showing that a bending portion of a support member moves away from the catheter body by the movement of the movable member, in the configuration of FIG. 28;

FIG. 30 is a perspective view of FIG. 29;

FIG. 31 is a front view of FIG. 30;

FIG. 32 is a cross-sectional view, taken along the line A32-A32' of FIG. 27;

FIG. 33 is a cross-sectional view schematically showing a distal end of a catheter for denervation according to another embodiment of the present disclosure;

FIG. 34 is a cross-sectional view schematically showing a distal end of a catheter for denervation according to another embodiment of the present disclosure;

FIG. 35 is a cross-sectional view schematically showing that an electrode moves away from the catheter body by the movement of the movable member, in the configuration of FIG. 34;

FIG. 36 is a cross-sectional view schematically showing a distal end of a catheter for denervation according to another embodiment of the present disclosure;

FIG. 37 is a cross-sectional view schematically showing that an electrode moves away from the catheter body by the movement of the movable member, in the configuration of FIG. 36;

FIG. 38 is a cross-sectional view schematically showing a distal end of a catheter for denervation according to another embodiment of the present disclosure;

FIG. 39 is a cross-sectional view showing the catheter of FIG. 38 along the longitudinal direction;

FIG. 40 is a cross-sectional view schematically showing that an electrode moves away from the catheter body by the movement of the movable member, in the configuration of FIG. 39;

FIG. 41 is a perspective view of FIG. 40;

FIG. 42 is a perspective view schematically showing a distal end of a catheter for denervation according to another embodiment of the present disclosure;

FIG. 43 is a perspective view schematically showing a distal end of a catheter according to a fourth aspect of the present disclosure;

FIG. 44 is a cross-sectional view, taken along the line A4-A4' of FIG. 43;

FIG. 45 is a cross-sectional view schematically showing that a bending portion of a first support member moves away from the catheter body by the movement of the movable member, in the configuration of FIG. 44;

FIG. 46 is a cross-sectional view schematically showing that a bending portion of a second support member moves away from the catheter body by the movement of an intermediate member, in the configuration of FIG. 45;

FIG. 47 is a perspective view of FIG. 46;

FIG. 48 is a front view of FIG. 47;

FIG. 49 is a schematic diagram showing arrangements and sections in the width direction of the first support member and the second support member according to an embodiment of the present disclosure;

FIG. 50 is a cross-sectional view schematically showing a distal end of a catheter for denervation according to another embodiment of the present disclosure;

FIG. 51 is a cross-sectional view schematically showing that an electrode moves away from the catheter body by the movement of the movable member and the intermediate member, in the configuration of FIG. 50;

FIG. 52 is a cross-sectional view schematically showing a distal end of a catheter for denervation according to another embodiment of the present disclosure;

FIG. 53 is a cross-sectional view schematically showing that an electrode moves away from the catheter body by the movement of the movable member and the intermediate member, in the configuration of FIG. 52;

FIG. 54 is a cross-sectional view schematically showing a distal end of a catheter for denervation according to another embodiment of the present disclosure;

FIG. 55 is a cross-sectional view schematically showing a distal end of a catheter for denervation according to another embodiment of the present disclosure;

FIG. 56 is a cross-sectional view showing the catheter of FIG. 55 along the longitudinal direction;

FIG. 57 is a cross-sectional view schematically showing that the movable member moves in the right direction, in the configuration of FIG. 56;

FIG. 58 is a cross-sectional view schematically showing that the intermediate member moves in the right direction, in the configuration of FIG. 57;

FIG. 59 is a perspective view of FIG. 58; and

FIG. 60 is a perspective view schematically showing a distal end of a catheter for denervation according to another embodiment of the present disclosure.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

Therefore, the description proposed herein is just a preferable example for the purpose of illustrations only, not intended to limit the scope of the disclosure, so it should be understood that other equivalents and modifications could be made thereto without departing from the spirit and scope of the disclosure.

First, a catheter for denervation according to a first aspect of the present disclosure will be described with reference to FIGS. 1 to 12.

FIG. 1 is a perspective view schematically showing a distal end of a catheter according to the first aspect of the present disclosure, and FIG. 2 is a cross-sectional view, taken along the line A1-A1' of FIG. 1. FIG. 2 shows a support member and an electrode employed in the catheter of FIG. 1.

Here, the distal end of the catheter means an end of the catheter which reaches a portion of a human body under a surgical procedure, between both ends of the catheter extending in the longitudinal direction, and it may also be called a catheter tip. In addition, an end of the catheter opposite to the distal end may be called a proximal end. Hereinafter, regarding various components which extend in the longitudinal direction of the catheter and thus have both ends in the longitudinal direction, an end of a component, located at the distal end of the catheter, will be called a distal end of the corresponding component, and a proximal end of a component, located at the proximal end of the catheter, will be called a proximal end of the corresponding component.

Referring to FIGS. 1 and 2, the catheter according to the present disclosure may include a catheter body 1100, a movable member 1200, an operating member 1300, a support member 1400, an electrode 1500 and a lead wire 1600.

The catheter body 1100 has a pipe or tube shape extending in one direction and has an inner space therein along the longitudinal direction. Here, the catheter body 1100 has both ends along the longitudinal direction, where an end of the catheter body 1100 firstly inserted into a human body during a surgical procedure using the catheter and reaching a destination, namely a target for the surgical procedure, is called a distal end 1101, and an end of the catheter body 1100 located near an operator and manipulated by the operator is called a proximal end (not shown), as described above.

The catheter body 1100 has a hollow tube shape and has an inner space therein along the longitudinal direction. Therefore, various components for a surgical procedure may be provided in or move through the inner space, and substances such as drugs or washing liquids may be injected through the inner space. For this, the proximal end of the catheter body 1100 may be formed so that the inner space is open to the outside.

The catheter body 1100 may have various shapes depending on its target or purpose and may also have various inner or outer diameters. In addition, the catheter body 1100 may be made of various materials, for example soft materials such as rubber and plastic or hard material such as metal. The present disclosure is not limited to a specific shape, material or size of the catheter body 1100, and the catheter body 1100 may have various shapes, materials, sizes or the like.

Preferably, the distal end 1101 of the catheter body may be made of soft and flexible material. The distal end 1101 of the catheter body is located at a front end of the catheter. Therefore, when the catheter moves along a blood vessel or the like, the distal end 1101 of the catheter body is likely to contact an inner wall of the blood vessel or the like. However, if the distal end 1101 of the catheter body is made of such a soft and flexible material, it is possible to minimize or prevent a damage of the blood vessel or the like, caused by the distal end 1101 of the catheter body, and it is also easy to change a moving direction of the distal end 1101 of the catheter body.

In addition, in a similar way, the distal end 1101 of the catheter body may have a rounded edge. For example, the distal end 1101 of the catheter body may have a circularly protruding shape toward the front end of the catheter.

The movable member 1200 is included in the inner space of the catheter body 1100. In addition, the movable member 1200 is configured to move along the longitudinal direction of the catheter body 1100 in the inner space of the catheter body 1100. For example, if the catheter body 1100 extends long in the lateral direction as shown in FIG. 2, the movable member 1200 may be configured to be movable in the lateral direction as indicated by the arrow b11.

The operating member 1300 may be formed to extend long along the longitudinal direction of the catheter body 1100, and one end of the operating member 1300, namely a distal end thereof, is connected and fixed to the movable member 1200. The operating member 1300 may be located according to the inner space of the catheter body 1100, and the other end of the operating member 1300, namely a proximal end thereof, may be exposed out of the catheter body 1100 through the open portion of the proximal end of the catheter body 1100. In this case, an operator may pull or push the operating member 1300 manually or automatically using a separate tool. In this case, the operating member 1300 may move in the lateral direction as indicated by the arrow b12 of FIG. 2, and by doing so, the movable member 1200 connected to one end of the operating member 1300 may move the lateral direction as indicated by the arrow b11.

The support member 1400 may have a rod or plate shape extending in one direction. In addition, the support member 1400 may be configured so that among both ends thereof in the longitudinal direction, one end is connected and fixed to the movable member 1200. In this configuration, if the movable member 1200 moves, the other end of the support member 1400 may move closer to or farther from the central axis of the catheter body 1100. This will be described in more detail with reference to FIGS. 3 to 5.

FIG. 3 is a cross-sectional view schematically showing that the other end of the support member 1400 whose one end is connected to the movable member 1200 moves away from the catheter body 1100 by the movement of the movable member 1200, in the configuration of FIG. 2. FIG. 4 is a perspective view of FIG. 3, and FIG. 5 is a front view of FIG. 3.

Referring to FIGS. 3 to 5, the catheter body 1100 has a plurality of side holes 1111 formed in a side surface of the distal end 1101. For example, as shown in FIG. 3, the side holes 1111 may be formed close to the distal end of the catheter body 1100 (in the right direction in FIG. 3) in comparison to the movable member 1200.

Here, the number of the side holes 1111 may correspond to the number of the support members 1400. For example, as shown in FIGS. 3 and 4, if the catheter has three support members 1400, three side holes 1111 may also be formed in the catheter body 1100.

In this case, the plurality of support members 1400 may move into or out of the catheter body 1100 through the side holes 1111 in a one-to-one relationship. For example, as shown in FIG. 3, if three side holes 1111 are formed close to the distal end 1101 of the catheter body 1100 in comparison to the movable member 1200, proximal ends of three support members 1400 (the left ends in FIG. 3) may be connected to the movable member 1200. In addition, three support members 1400 may be configured so that their distal ends (the right end in FIG. 3) are exposed out of the catheter body 1100 according to the movement of the movable member 1200 through three side holes 1111, respectively.

In this case, if the movable member 1200 moves in the right direction, namely toward the distal end of the catheter body 1100, as indicated by the arrow c11, three support members 1400 slide through the side holes 1111, respectively, so that their distal ends move away from the catheter body 1100, as indicated by the arrows d11, d12 and d13 in FIGS. 3 and 4. Here, the movement of the distal end of the support member 1400 away from the catheter body 1100 means that the distal end of the support member 1400 gradually moves away from a central axis o1 of the catheter body 1100.

Meanwhile, the electrode 1500 is provided at the other end of the plurality of support members 1400. For example, in the embodiment depicted in FIGS. 1 to 4, the electrode 1500 may be provided at each distal end of the plurality of support members 1400.

The electrode 1500 may be connected to an energy supplying unit (not shown) through the lead wire 1600 to generate heat. In addition, the heat generated by the electrode 1500 may ablate surrounding tissues. For example, the electrode 1500 may ablate nerves around a blood vessel by generating heat of about 40° C. or above, preferably 40 to 80° C., and thus the nerves may be blocked. However, the temperature of the heat generated by the electrode 1500 may be set in various ways according to the use or purpose of the catheter.

The electrode 1500 should apply heat to nerve tissues around a blood vessel in contact with a wall of the blood vessel, and thus the electrode 1500 is preferably closely adhered to the wall of the blood vessel. Therefore, the electrode 1500 may have a curved shape, for example a circular, semicircular or oval shape, to conform to the shape of the inner wall of the blood vessel. In this embodiment, the electrode 1500 may be more clearly adhered to the wall of the blood vessel, and thus the heat generated by the electrode 1500 may be efficiently transferred to nerve tissues around the blood vessel.

The electrode 1500 may be made of material such as platinum or stainless steel, but the present disclosure is not limited to such specific materials of the electrode 1500. The electrode 1500 may be made of various materials in consideration of various factors such as a generated energy type and an operation target.

Preferably, the electrode 1500 may generate heat by means of radio frequency (RF). For example, the electrode 1500 may be connected to a high frequency generating unit through the lead wire 1600 and emits high frequency energy to ablate nerves.

Meanwhile, the electrode 1500 provided at the catheter may be a negative electrode, and a positive electrode corresponding to the negative electrode may be connected to an energy supplying unit such as a high frequency generating unit, similar to the negative electrode, and attached to a specific portion of a human body in the form or patch or the like.

Since the electrode 1500 is provided at the other end of the support member 1400, when the other end of the support member 1400 moves closer to or farther from the catheter body 1100, the electrode 1500 may also move closer to or farther from the catheter body 1100 accordingly.

For example, as shown in FIGS. 2 and 3, if the side hole 1111 is located closer to the distal end of the catheter body 1100 (in the right direction of FIGS. 2 and 3) in comparison to the movable member 1200 and the movable member 1200 is connected to the proximal end of the support member 1400, the electrode 1500 may be provided at the distal end of the support member 1400. In this embodiment, when the movable member 1200 moves in a direction from the proximal end of the catheter body 1100 toward the distal end thereof as indicated by the arrow c11 of FIG. 3, the electrode 1500 provided at the distal end of the support member 1400 may be configured to move away from the catheter body 1100. On the contrary, if the movable member 1200 moves in a direction opposite to the arrow c11 of FIG. 3, the electrode 1500 provided at the distal end of the support member 1400 may be configured to move toward the catheter body 1100.

In other words, the electrode 1500 may be configured to move toward or away from a line perpendicular to the central axis o1 according to the movement of the movable member 1200, based on the central axis o1 of the catheter body 1100 in the longitudinal direction.

For this, the support member 1400 having the electrode 1500 at the other end thereof to support the electrode 1500 may have suitable material or shape so that the electrode 1500 may move closer to or farther from the central axis o1 of the catheter body 1100 according to the movement of the movable member 1200.

For example, the support member 1400 may be pre-shaped so that when the movable member 1200 moves along the arrow c11, the other end may move away from the central axis o1 of the catheter body 1100 as shown in FIGS. 3 to 5. In particular, the support member 1400 may also be made of a shape memory alloy such as nitinol. In this embodiment, if the support member 1400 deviates from the catheter body 1100, the other end moves away from the central axis o1 of the catheter body 1100 according to the pre-shaped form, and thus the electrode 1500 provided at the other end of the support member 1400 may also move away from the central axis o1 of the catheter body 1100.

However, the present disclosure is not limited thereto, and various configurations may be used so that the other end of the support member 1400 having the electrode 1500 moves closer to or farther from the catheter body 1100 according to the movement of the movable member 1200. For example, the support member 1400 may be configured so that the other end of the support member 1400 moves closer to or farther from the catheter body 1100 by changing angles among the side hole 1111, one end of the support member 1400 and a horizontal line according to the movement of the movable member 1200. In other words, in the embodiment of FIG. 3, if the movable member 1200 moves in the direction c11, the angles among the side hole 1111, one end of the support member 1400 and the horizontal line gradually increase, the other end of the support member 1400 having the electrode 1500 may be configured to gradually move away from the catheter body 1100.

As described above, in the catheter for denervation according to the present disclosure, the electrode 1500 is provided at the other end of the support member 1400 to move closer to or farther from the catheter body 1100. Therefore, if the catheter according to the present disclosure is used to perform denervation, in a state in which the other end of the support member 1400 having the electrode 1500 is located close to the catheter body 1100, the distal end of the catheter, namely a catheter tip, may be moved to an operation target through a blood vessel. In addition, if the catheter tip reaches the operation target, the other end of the support member 1400 having the electrode 1500 is moved away from the catheter body 1100, so that electrode 1500 contacts or approaches to the inner wall of the blood vessel. In addition, in this state, energy for generating heat, for example high frequency energy, is emitted through the electrode 1500, thereby blocking nerves around the blood vessel. After that, if the denervation is completed with the energy emitted through the electrode 1500, the other end of the support member 1400 having the electrode 1500 moves again close to the catheter body 1100, and then the catheter may be extracted from the blood vessel.

Meanwhile, in a state in which the electrode 1500 moves away from the central axis o1 of the catheter body, the distance between the electrode 1500 and the central axis o1 of the catheter body may be selected in various ways according to a size of an operation target, for example an inner diameter of the blood vessel. For example, in a state in which the electrode 1500 moves farthest away from the central axis o1 of the catheter body, a distance between each electrode 1500 and the central axis o1 of the catheter body may be 2 mm to 4 mm.

The lead wire 1600 is respectively electrically connected to the plurality of electrodes 1500 to give a power supply path to the plurality of electrodes 1500. In other words, the lead wire 1600 is connected between the electrode 1500 and the energy supplying unit (not shown) so that the energy supplied from the energy supplying unit is transferred to the electrode 1500. For example, one end of the lead wire 1600 is connected to the high frequency generating unit and the other end thereof is connected to the electrode 1500 to transfer the energy generated by the high frequency generating unit to the electrode 1500, thereby allowing the electrode 1500 to generate heat by high frequency.

In particular, the lead wire 1600 according to the present disclosure may include a variable region 1610 configured to adjust its length, as shown in FIGS. 3 and 4. Here, the proximal end of the variable region 1610 may be fixed to one side of the catheter body 1100, and the distal end of the variable region 1610 may be fixed to the movable member 1200. For this, a fixing unit 1140 for fixing one end of the variable region 1610 of the lead wire 1600 to the inner space may be separately provided at the catheter body 1100, as shown in FIG. 3.

In the configuration of the present disclosure, even though the electrode 1500 is configured to move closer to or farther from the catheter body 1100 according to the movement of the movable member 1200, the lead wire 1600 may keep substantially fixed due to the variable region 1610. In other words, even though the movable member 1200 to which the distal end of the variable region 1610 (the right end in FIG. 3) is fixed moves in the direction c11 as shown in FIG. 3, only the length of the variable region 1610 increases, and thus the proximal end of the variable region 1610 (the left end in FIG. 3) may be fixed. Therefore, even though the movable member 1200 moves, only the distal end of the lead wire 1600 moves based on the variable region 1610, and most regions of the lead wire 1600 inserted into the catheter body 1100 does not need to move. For this reason, due to this configuration of the present disclosure, even though the movable member 1200 moves, an operator does not need to insert or extract the lead wire 1600, which prevents the surgical procedure of the operator from being complicated. In addition, if the blood vessel has a serious curve, the lead wire 1600 may not easily move into the catheter body 1100. At this time, since the lead wire 1600 does not need to move in the catheter body 1100 except for the catheter tip portion according to the present disclosure, no problem is caused due to difficult movement of the lead wire 1600.

Preferably, the variable region 1610 of the lead wire may have a spiral coil shape like a spring, as shown in the figures. However, the present disclosure is not limited to such a shape of the variable region. For example, the variable region 1610 of the lead wire may be bent or folded in various directions in a zigzag pattern. In other words, in the present disclosure, the variable region 1610 of the lead wire may be configured in various shapes so that a length between both ends of the variable region 1610 may be adjusted by spreading or folding the curved portion of the variable region 1610 according to the movement of the movable member 1200.

Meanwhile, even though FIGS. 3 and 4 show that three lead wires 1600 are provided at the distal end of the catheter body 1100 and the variable region 1610 is formed at each lead wire 1600, the present disclosure is not limited to this configuration. For example, the lead wire 1600 may be configured with a single wire till the movable member 1200, which diverges into three wires at the right side of the movable member 1200. In this case, only one variable region 1610 may be formed at the lead wire 1600.

The lead wire 1600 may be attached to an upper or lower portion of the support member 1400 or provided in the support member 1400, between the movable member 1200 and the electrode 1500. In addition, the lead wire 1600 may not be fixed to the support member 1400 but connected to the electrode 1500 to be separated from the support member 1400.

Moreover, the lead wire 1600 may not be provided separate from the support member 1400 but implemented to be integrated with the support member 1400. For example, at least a part of the support member 1400 may be made of electrically conductive material, so that the support member 1400 may serve as the lead wire 1600 between the movable member 1200 and the electrode 1500.

Meanwhile, even though the embodiment of FIGS. 2 and 3 has been illustrated so that the plurality of side holes 1111 are located close to the distal end of the catheter body 1100 (in the right direction) in comparison to movable member 1200, the present disclosure is not limited thereto.

FIG. 6 is a cross-sectional view showing a distal end of a catheter for denervation according to another embodiment of the present disclosure. In addition, FIG. 7 is a schematic diagram showing that the electrode 1500 moves away from the catheter body 1100 by the movement of the movable member 1200, in the configuration of FIG. 6. In this embodiment, components similar to those of FIGS. 1 to 5 will not be described in detail and components different therefrom will be described in detail.

First, referring to FIG. 6, a plurality of side holes 1111 is formed in a side surface of the catheter body 1100, and different from FIGS. 2 and 3, the side holes 1111 are located close to the proximal end of the catheter body 1100 (in the left direction in FIG. 6) in comparison to the movable member 1200. In addition, a movable member 1200 is connected to each distal end of the plurality of support members 1400, and an electrode 1500 is provided at the proximal end of the plurality of support members 1400.

At this time, as indicated by the arrow ell in FIG. 6, if the movable member 1200 moves in a direction from the distal end of the catheter body 1100 to the proximal end thereof, the electrode 1500 provided at the proximal end of the support member 1400 may deviate and move away from the catheter body 1100 as indicated by the arrows f11, f12 and f13 in FIG. 7.

In other words, even though the electrode 1500 moves away from the catheter body 1100 in the embodiment depicted in FIGS. 2 and 3 if an operator pushes the operating member 1300 toward the distal end of the catheter, in the embodiment depicted in FIGS. 6 and 7, when an operator pulls the operating member 1300 toward the proximal end of the catheter, the electrode 1500 moves away from the catheter body 1100.

Meanwhile, in the embodiment of FIGS. 6 and 7, the lead wire 1600 may also have a variable region 1610, and due to the variable region 1610, the entire portion of the lead wire 1600 does not need move even though the movable member 1200 moves. In other words, in the embodiment of FIGS. 6 and 7, a proximal end of the variable region 1610 of the lead wire 1600 is fixed to one side of the catheter body 1100, namely to the fixing unit 1140 of the catheter body 1100, and a distal end of the variable region 1610 is fixed to the movable member 1200. Therefore, when the movable member 1200 moves, only the length of the variable region 1610 changes, the entire lead wire 1600 does not need to move in the catheter body 1100 except for the variable region 1610.

Preferably, a side insert groove 1121 may be formed in the catheter body 1100. In other words, as shown in FIGS. 2 and 6, the side insert groove 1121 may be formed in a side surface of the catheter body 1100 where the side hole 1111 is formed. In addition, the side insert groove 1121 may be concave toward the inside of the catheter body 1100 so that the electrode 1500 may be inserted therein.

In this embodiment, while the distal end of the catheter body 1100, namely the catheter tip, is moving through the blood vessel, the electrode 1500 may move in a state of being inserted into the side insert groove 1121. Therefore, it is possible to minimize a damage of the blood vessel caused by the electrode 1500 while the catheter tip is moving.

For this, more preferably, when the electrode 1500 is inserted into the side insert groove 1121, the electrode 1500 may not protrude toward the outside of the side surface of the catheter body 1100. For example, in the embodiments of FIGS. 2 and 6, based on the side insert groove 1121 and the electrode 1500 located at the uppermost location, a depth of the side insert groove 1121, namely a vertical length, is equal to or greater than the vertical length of the electrode 1500. In this case, the electrode 1500 may be perfectly inserted without protruding toward the outside of the catheter body 1100.

Also preferably, in the embodiment, if the electrode 1500 is inserted into the side insert groove 1121, the side hole 1111 located at the side insert groove 1121 may be closed. In other words, in a state in which the electrode 1500 is inserted into the side insert groove 1121, the side hole 1111 of the corresponding side insert groove 1121 may not allow a fluid to flow in or out. In this embodiment, if the catheter tip moves through the blood vessel in a state in which the electrode 1500 is inserted into the side insert groove 1121, it is possible to prevent blood from flowing in through the side hole 1111, and it is also possible to prevent operations of each component located in the catheter from being disturbed by coagulated blood. In addition, it is also possible to prevent blood from flowing out to the proximal end of the catheter body 1100 through the inner space of the catheter body 1100.

Meanwhile, even though it has been illustrated in the embodiments of FIGS. 1 and 7 that a through hole for allowing the support member 1400 to pass through is formed at the side surface of the catheter body 1100, the present disclosure is not limited to these embodiments.

FIG. 8 is a cross-sectional view schematically showing a distal end of a catheter for denervation according to another embodiment of the present disclosure. In addition, FIG. 9 is a schematic diagram showing that the electrode 1500 moves away from the catheter body 1100 by the movement of the movable member 1200, in the configuration of FIG. 8. Hereinafter, components different from those of the former embodiment will be described in detail.

First, referring to FIG. 8, a plurality of front holes 1112 may be formed in a front surface of the catheter body 1100, which is located at the furthermost tip of the distal end. In addition, the plurality of support members 1400 may respectively move into or out of the catheter body 1100 through the front hole 1112. Here, the movable member 1200 may be connected to the proximal end of the plurality of support members 1400, and the electrode 1500 may be provided at the distal end thereof.

In this case, as shown in FIG. 9, if the movable member 1200 moves in a direction from the proximal end of the catheter body 1100 to the distal end thereof, the electrode 1500 may be taken out of the catheter body 1100.

Preferably, if the electrode 1500 is inserted into a portion of the catheter body 1100 where the front hole 1112 is formed, a front insert groove 1122 concave toward the inside of the catheter body 1100. In this case, when the catheter tip is moving in the blood vessel, the electrode 1500 may move in a state of being inserted into the front insert groove 1122. Therefore, it is possible to prevent the inside of the blood vessel from being damaged by extrusion of the electrode 1500 while the catheter tip is moving.

At this time, more preferably, if the electrode 1500 is inserted into the front insert groove 1122, the front hole 1112 may be closed. In this embodiment, since the catheter tip may move in a state in which the front hole 1112 is closed by the electrode 1500, it is possible to prevent blood or another fluid from flowing into the catheter through the front hole 1112.

Meanwhile, in this embodiment, a plurality of through holes are formed in the side surface or the front surface of the catheter body 1100, and only the support member 1400 may be partially received in the inner space of the catheter body 1100. However, the present disclosure is not limited thereto.

FIG. 10 is a cross-sectional view schematically showing a distal end of a catheter for denervation according to another embodiment of the present disclosure. In addition, FIG. 11 is a schematic diagram showing that an electrode 1500 moves away from the catheter body 1100 by the movement of the movable member 1200, in the configuration of FIG. 10. In this embodiment, components similar to those of the former embodiments will not be described in detail and components different therefrom will be described in detail.

Referring to FIGS. 10 and 11, an opening 1113 is formed at the front surface of the distal end of the catheter body 1100. In other words, the distal end of the catheter body 1100 may open the inner space of the catheter body 1100 through the opening 1113.

In addition, the plurality of support members 1400 and the plurality of electrodes 1500 may be inserted into and received in the inner space of the catheter body 1100 through the opening 1113 or be drawn out of the catheter body 1100 through the opening 1113.

In more detail, as shown in FIGS. 10 and 11, the plurality of support members 1400 may be respectively configured so that the movable member 1200 is connected to the proximal end thereof and the electrode 1500 is provided at the distal end thereof.

In this case, as shown in FIG. 11, if the movable member 1200 moves in a direction from the proximal end of the catheter body 1100 toward the distal end thereof, the electrode 1500 provided at the distal end of the support member 1400 may be drawn out of the catheter body 1100 through the opening 1113. In addition, the drawn electrode 1500 moves away from the central axis o1 of the catheter body 1100 to contact the inner wall of the blood vessel or approach thereto.

In this embodiment, the plurality of support members 1400 and the plurality of electrodes 1500 may be configured to be accommodated in the inner space of the catheter body 1100 while the catheter tip is moving, as shown in FIG. 10. After that, if the catheter tip reaches an operation target, the plurality of support members 1400 and the plurality of electrodes 1500 are drawn out of the catheter body 1100 through the opening 1113 as shown in FIG. 11, so that the electrode 1500 moves away from the catheter body 1100. After that, if nerves at the corresponding portion are blocked due to heat emission of the electrode 1500, the support member 1400 and the electrode 1500 are put into and received in the catheter body 1100 through the opening 1113 again, and in this state, the catheter tip may be drawn out of the human body along the wall of the blood vessel or moved to another portion of the human body.

Preferably, in several embodiments of the present disclosure, the plurality of electrodes 1500 may be configured to be spaced apart from each other by a predetermined distance in the longitudinal direction of the catheter body 1100 in a state in which the other end of the support member 1400 is far from the catheter body 1100.

For example, referring to the embodiment of FIG. 3, in a state in which three electrodes 1500 move away from the catheter body 1100, as indicated by the arrows g11 and g12, the three electrodes 1500 may be configured to be spaced apart from each other by a predetermined distance in the longitudinal direction of the catheter body 1100.

If the plurality of electrodes 1500 respectively emits heat, heated portions of the blood vessel may swell toward the inside of the blood vessel, which may cause stenosis. However, if three electrodes 1500 are spaced apart from each other by a predetermined distance in the longitudinal direction of the catheter body 1100 as in this embodiment, the heated portions of the blood vessel are spaced apart from each other by a predetermined distance in the longitudinal direction of the blood vessel, thereby preventing such stenosis from occurring.

In particular, the distance between electrodes 1500 in the longitudinal direction of the catheter body 1100 as indicated by the arrows g11 and g12 may be variously set according to a size of the catheter or an operation target. For example, the catheter may be configured so that in a state in which the plurality of electrodes 1500 is far from the catheter body 1100, the distance between electrodes 1500 in the longitudinal direction of the catheter body 1100 is 0.3 to 0.8 cm. In this embodiment, it is possible to prevent stenosis of the blood vessel and prevent nerves around the blood vessel from passing between the electrodes 1500 to the minimum.

Meanwhile, in a state in which the plurality of electrodes 1500 is far from the catheter body 1100 as in this embodiment, the electrodes 1500 may be configured to be spaced apart from each other by a predetermined distance in the longitudinal direction of the catheter body 1100 in various ways.

For example, in order to space the electrodes 1500 from each other, the plurality of support members 1400 may be configured so that distances between one end and the other end thereof are different from each other. In other words, the plurality of support members 1400 may have a rod shape extending in one direction, and their lengths may be different from each other. For example, in the embodiment of FIG. 2, the three support members 1400 may be configured to have rod shapes with different lengths. Therefore, when the movable member 1200 moves in the right direction, an electrode 1500 provided at a support member 1400 having a longest length may be located at a foremost position in the longitudinal direction of the catheter body 1100, and an electrode 1500 provided at a support member 1400 having a shortest length may be located at a rearmost position in the longitudinal direction of the catheter body 1100. In particular, in a state in which the electrode 1500 is far from the catheter body 1100, in order to space the plurality of support members 1400 from each other by 0.3 cm to 0.8 cm, the plurality of support members 1400 may be configured to have length differences of 0.3 cm to 0.8 cm from each other.

As another example, in order to space the electrodes 1500 from each other, the movable member 1200 may have a step formed at a surface thereof to which the plurality of support members 1400 is connected. For example, in the embodiment of FIG. 3, the step may be formed at the right surface of the movable member 1200, and the plurality of movable members 1200 may be connected to different steps. In this embodiment, even though the plurality of support members 1400 have the same length, due to the steps formed at the movable member 1200, the electrodes 1500 may be spaced apart from each other as much as step lengths.

In addition, various schemes may be used to space the electrodes 1500 from each other, and for example, the electrodes 1500 may be spaced apart from each other by inclining the surface of the movable member 1200, to which the support member 1400 is connected, by a predetermined angle with respect to a direction perpendicular to the central axis o1 of the catheter.

Also preferably, in various embodiments of the present disclosure, in a state in which the other end of the support member 1400 is far from the catheter body 1100, the plurality of electrodes 1500 may be configured to be spaced apart from each other by a predetermined angle based on the central axis o1 of the catheter body 1100 in the longitudinal direction.

For example, as shown in FIG. 5, in a state in which three electrodes 1500 move away from the catheter body 1100 according to the movement of the movable member 1200, assuming that angles among three electrodes 1500 are h11, h12 and h13 based on the central axis o1 of the catheter, h11, h12 and h13 have predetermined angles, so that the three electrodes 1500 are spaced apart from each other by the predetermined angles. For example, h11, h12 and h13 may be identically 120°.

In addition, in an embodiment including four or more support members 1400 and four or more electrodes 1500, the plurality of electrodes 1500 may also be spaced apart from each other by predetermined angles based on the central axis o1 of the catheter.

In the embodiment in which the electrodes 1500 are spaced apart from each other by predetermined angles based on the central axis o1 of the catheter body 1100 as described above, the electrodes 1500 may be configured to spread widely in all directions around the catheter body 1100. Therefore, even though nerves are disposed in a local portion of the blood vessel, the electrodes 1500 may cover the nerves.

Also preferably, as shown in the figures of various embodiments, the catheter body 1100 may include a stopper 1130 in the inner space. The stopper 1130 limits a moving distance of the movable member 1200, and the catheter body 1100 may include at least one stopper.

More preferably, the stopper 1130 may include a first stopper 1131 and a second stopper 1132. Here, the first stopper 1131 may be provided close to the proximal end in comparison to the movable member 1200 so that the movable member 1200 is limited not to move further toward the proximal end. In addition, the second stopper 1132 may be provided close to the distal end in comparison to the movable member 1200 so that the movable member 1200 is limited not to move further toward the distal end.

In the embodiment including the stopper 1130 at the catheter body 1100 as described above, it is possible to facilitate an operator's manipulation and also prevent various components included in the catheter from being damaged. For example, in the embodiment of FIG. 2, the first stopper 1131 may limit the movable member 1200 not to move further in the left direction, which may prevent a connection between the electrode 1500 and the support member 1400 or a connection between the electrode 1500 and the lead wire 1600 from being cut. In another example, in the embodiment of FIG. 3, the second stopper 1132 may limit the movable member 1200 no to move further in the right direction, which may prevent the lead wire 1600 from being cut or prevent a connection between the lead wire 1600 and the fixing unit 1140 from being cut.

Also preferably, the catheter body 1100 may have a guide hole formed at the distal end thereof so that a guide wire may pass through. Here, the guide wire is used for guiding the catheter to an operation target and may reach the operation target prior to the catheter. In this embodiment, the guide wire may be inserted into the catheter through the guide hole, and the catheter tip may reach the operation target along the guide wire.

At least one guide hole may be formed in the catheter body 1100. For example, the catheter body 1100 may have a single guide hole at the distal end, so that a guide wire is inserted into the guide hole. In this case, when the catheter body 1100 moves, the guide wire inserted through the guide hole may move along the inner space of the catheter body 1100. In another example, the catheter body 1100 may include two guide holes at the distal end. In this case, the guide wire may be inserted into the catheter body 1100 through one guide hole and be drawn out of the catheter body 1100 through the other guide hole.

As described above, in the embodiment in which a guide hole is formed in the catheter body 1100, since the guide wire inserted into the guide hole guides movement of the catheter tip, the catheter may smoothly reach an operation target, and the catheter may be easily manipulated. Moreover, since the catheter does not need to include a component for adjusting a moving direction of the catheter, the catheter may have a simpler structure, which is advantageous in reducing the size of the catheter.

Also preferably, the catheter for denervation according to the present disclosure may further include an elastic member (not shown).

The elastic member may be connected between the catheter body 1100 and the movable member 1200. For example, in the embodiments of FIGS. 2, 8 and 10, the elastic member may be connected between the fixing unit 1140 of the catheter body 1100 and the movable member 1200. In addition, in the embodiment of FIG. 6, the elastic member may be connected between the movable member 1200 and the terminal (a right tip portion of the catheter body 1100 of FIG. 6) of the catheter body 1100.

As described above, in the embodiment including the elastic member, the movable member 1200 may return to its original state more easily due to the restoring force of the elastic member.

For example, as shown in FIG. 3, in a state in which the movable member 1200 is moved in the right direction, after nerves are blocked by the electrode 1500, the movable member 1200 should move in the left direction again. However, if an elastic member is included between the fixing unit 1140 and the movable member 1200, the movable member 1200 may move more easily in the left direction due to the restoring force of the elastic member. Therefore, after nerves are blocked by the electrode 1500, an operator may not give great efforts to insert the electrode 1500 into the side insert groove 1121.

In addition, if the elastic member is provided, it is possible to prevent the electrode 1500 from deviating from the side insert groove 1121 of the catheter body 1100 while the catheter tip is moving, and thus it is also possible to prevent the blood vessel from being damaged due to deviation or protrusion of the electrode 1500. Moreover, even though the stopper 1130 is not provided, the moving distance of the movable member 1200 may be limited by the elastic member, which may prevent various components from being damaged due to excessive movement of the movable member 1200.

FIG. 12 is a perspective view schematically showing a distal end of a catheter for denervation according to another embodiment of the present disclosure.

Referring to FIG. 12, the catheter for denervation according to the present disclosure may further include an end tip 1700.

The end tip 1700 is provided at the front surface of the distal end of the catheter body. In other words, the end tip 1700 may be regarded as being located farther from the terminal of the catheter body. In this case, the end tip 1700 may be a component serving as the terminal of the catheter for denervation according to the present disclosure.

The end tip 1700 may be made of soft and flexible material. In particular, the end tip 1700 may be made of a composition containing polyether block amide (PEBA). Here, the composition for the end tip 1700 may contain other additives in addition to the polyether block amide. For example, the end tip 1700 may be made of a composition containing 70 weight % of polyether block amide and 30 weight % of barium sulfate, based on the entire weight of the composition.

In this configuration of the present disclosure, when the distal end 1101 of the catheter body moves along a blood vessel or the like, the end tip 1700 made of soft and flexible material is located at a foremost position, which may reduce damages to the blood vessel and facilitate easier change of a moving direction. Further, the end tip 1700 made of the above material may be photographed by X-ray, and thus a location of the distal end of the catheter body may be easily figured out.

Preferably, the end tip 1700 may have a hollow tube shape. In addition, the hollow of the end tip 1700 may extend in the same direction of the longitudinal direction of the catheter body. If the end tip 1700 has a tube shape as described above, a guide wire may pass through the hollow of the end tip. For example, the end tip may have a tube shape with a length of 6 mm and a hollow diameter of 0.7 mm.

The end tip may extend along the longitudinal direction of the catheter body. At this time, the end tip may have different sizes along the length thereof. In particular, if the end tip has a cylindrical shape, a distal end of the end tip may have the smallest diameter in comparison to other regions. For example, the distal end of the end tip may have a smallest diameter of 1.1 mm, when the thickest region of the end tip has a diameter of 1.3 mm.

The end tip 1700 may have a suitable length, which is not too long and not too short. For example, in the configuration of FIG. 12, the length of the end tip 1700, indicated by L1, may be 5 mm to 15 mm. In this configuration, when the catheter moves along the inner space of a blood vessel or the inner space of a sheath, it is possible to prevent the movement from being disturbed by the end tip 1700. In addition, in this configuration, a shape of the blood vessel or the like at which the end tip 1700 is located may be easily figured out from a bending shape or a bending direction of the end tip 1700.

Also preferably, the catheter for denervation according to the present disclosure may further include a temperature measuring member (not shown).

In particular, the temperature measuring member may be provided around the electrode 1500 to measure a temperature of the electrode 1500 or around the electrode 1500. In addition, the temperature measured by the temperature measuring member as described above may be used for controlling the temperature of the electrode 1500. Here, the temperature measuring member may be connected to the lead wire 1600 through a separate wire, and the separate wire may extend to the proximal end of the catheter body 1100 through the inner space of the catheter body 1100 and be drawn out of the catheter body 1100.

Meanwhile, even though the several embodiments have been illustrated so that three support members 1400 and three electrodes 1500 are provided, the number of support members 1400 and electrodes 1500 are not limited to the above in the present disclosure, and the number of support members 1400 and electrodes 1500 may be variously set.

A denervation apparatus according to the present disclosure includes the catheter for denervation. In addition, the denervation apparatus may further include an energy supplying unit and an opponent electrode in addition to the catheter for denervation. Here, the energy supplying unit may be electrically connected to the electrode 1500 through the lead wire 1600. In addition, the opponent electrode may be electrically connected to the energy supplying unit through a lead wire 1600 which is different from the above lead wire 1600. In this case, the energy supplying unit may supply energy to the electrode 1500 of the catheter in the form of high frequency or the like, and the electrode 1500 of the catheter generates heat to ablate nerves around the blood vessel, thereby block the nerves.

Next, a catheter for denervation according to a second aspect of the present disclosure will be described with reference to FIGS. 13 to 26.

FIG. 13 is a perspective view schematically showing a distal end of a catheter according to the second aspect of the present disclosure, and FIG. 14 is a cross-sectional view, taken along the line A2-A2' of FIG. 13. FIG. 14 shows a support member, an electrode and a lead wire included in the catheter of FIG. 13 for convenience.

Here, as described above, the distal end of the catheter means an end of the catheter which reaches a portion of a human body under a surgical procedure, between both ends of the catheter extending in the longitudinal direction, and it may also be called a catheter tip. In addition, an end of the catheter opposite to the distal end may be called a proximal end. Hereinafter, regarding various components which extend in the longitudinal direction of the catheter and thus have both ends in the longitudinal direction, an end of a component, located at the distal end of the catheter, will be called a distal end of the corresponding component, and a proximal end of a component, located at the proximal end of the catheter, will be called a proximal end of the corresponding component.

Referring to FIGS. 13 and 14, the catheter according to the present disclosure may include a catheter body 2100, a movable member 2200, an operating member 2300, a support member 2400, n electrode 2500 and a lead wire 2600.

The catheter body 2100 has a pipe or tube shape extending in one direction and has an inner space therein along the longitudinal direction. Here, the catheter body 2100 has both ends along the longitudinal direction, where an end of the catheter body 2100 firstly inserted into a human body during a surgical procedure using the catheter and reaching a destination, namely a target for the surgical procedure, is called a distal end 2101, and an end of the catheter body 2100 located near an operator and manipulated by the operator is called a proximal end (not shown), as described above.

The catheter body 2100 has a hollow tube shape and has an inner space therein along the longitudinal direction. Therefore, various components for a surgical procedure may be provided in or move through the inner space, and substances such as drugs or washing liquids may be injected through the inner space. For this, the proximal end of the catheter body 2100 may be formed so that the inner space is open to the outside.

The catheter body 2100 may have various shapes depending on its target or purpose and may also have various inner or outer diameters. In addition, the catheter body 2100 may be made of various materials, for example soft materials such as rubber and plastic or hard material such as metal. The present disclosure is not limited to a specific shape, material or size of the catheter body 2100, and the catheter body 2100 may have various shapes, materials, sizes or the like.

The movable member 2200 is provided at the distal end 2101 of the catheter body and may be configured to be movable in the longitudinal direction of the catheter body 2100. In addition, by means of the movement of the movable member 2200, a distance between the terminal 2110 of the catheter body and the movable member 2200 may increase or decrease.

In particular, as shown in FIGS. 13 and 14, the movable member 2200 may be provided out of the catheter body 2100. In other words, the movable member 2200 may be separated from the catheter body 2100 and located at an outer side in comparison to the terminal 2110 of the catheter body (in the right side in FIG. 14). In this case, if the movable member 2200 moves in the left direction, the distance between the movable member 2200 and the catheter body 2100 may decrease, and if the movable member 2200 moves in the right direction, the distance between the movable member 2200 and the catheter body 2100 may increase.

Preferably, the distal end 2101 of the catheter body and/or the movable member 2200 may be made of soft and flexible material. Since the distal end 2101 of the catheter body and the movable member 2200 are located at a front end of the catheter, when the catheter moves along a blood vessel or the like, the distal end 2101 of the catheter body and the movable member 2200 are likely to contact an inner wall of the blood vessel or the like. However, if the distal end 2101 of the catheter body and the movable member 2200 are made of such a soft and flexible material, it is possible to minimize or prevent a damage of the blood vessel or the like, caused by the distal end 2101 of the catheter body and the movable member 2200, and it is also easy to change a moving direction of the distal end 2101 of the catheter body and the movable member 2200.

In addition, in a similar way, the distal end 2101 of the catheter body and/or the movable member 2200 may have a rounded edge. In particular, as shown in the figure, the movable member 2200 may have an outer surface (the right surface in FIG. 14) which circularly protrudes toward the front end of the catheter. In addition, the inner surface (the left surface in FIG. 14) of the movable member 2200 may also have a rounded edge.

The operating member 2300 may be formed to extend long along the longitudinal direction of the catheter body 2100, and may move the movable member 2200 in the longitudinal direction. For this, one end of the operating member 2300, namely a distal end thereof, is connected and fixed to the movable member 2200, and the operating member 2300 may be located according to the inner space of the catheter body 2100. In addition, the other end of the operating member 2300, namely a proximal end thereof, may be exposed out of the catheter body 2100 through the open portion of the proximal end of the catheter body 2100. In this case, an operator may pull or push the operating member 2300 manually or automatically using a separate tool. In this case, the operating member 2300 may move in the lateral direction as indicated by the arrow b22 of FIG. 14, and by doing so, the movable member 2200 connected to one end of the operating member 2300 may move the lateral direction as indicated by the arrow b21.

Meanwhile, in the embodiment of FIG. 14, since the operating member 2300 is connected to the movable member 2200 out of the catheter body 2100, an operation hole 2120 may be formed in the catheter body 2100 so that the operating member 2300 may move through the operation hole 2120.

The support member 2400 may have a rod or plate shape extending in one direction and may be connected between the catheter body 2100 and the movable member 2200. In other words, one end of the support member 2400 may be connected to the terminal 2110 of the catheter body, namely to a farthest end of the distal end 2101 of the catheter body, and the other end thereof may be connected to the movable member 2200. For example, in the configuration of FIG. 14, the proximal end (left end) of the support member 2400 may be fixed to the outer surface of the terminal 2110 of the catheter body, and the distal end (right end) of the support member 2400 may be fixed to the left surface of the movable member 2200.

Here, the catheter body 2100 and the movable member 2200 provided at both ends of the support member 2400 may have flat surfaces when standing in a direction perpendicular to the longitudinal direction of the catheter body 2100. In other words, based on FIG. 14, the right surface of the terminal 2110 of the catheter body to which the proximal end of the support member 2400 is connected and the left surface of the movable member 2200 to which the distal end of the support member 2400 is connected may be vertically flat with each other and stand perpendicular to the central axis of the catheter body 2100 in the longitudinal direction.

Meanwhile, as described above, the movable member 2200 may be configured to move close to or away from the terminal 2110 of the catheter body in the longitudinal direction of the catheter body 2100 by means of the operating member 2300.

In particular, in the present disclosure, if the movable member 2200 moves to decrease the distance between the terminal 2110 of the catheter body and the movable member 2200, the support member 2400 may be bent at least partially, and this bending portion may be configured to move away from the catheter body 2100. This will be described in more detail with reference to FIGS. 15 to 17.

FIG. 15 a cross-sectional view schematically showing that the bending portion of the support member 2400 moves away from the catheter body 2100 by the movement of the movable member 2200, in the configuration of FIG. 14. In addition, FIG. 16 is a perspective view of FIG. 15, and FIG. 17 is a front view of FIG. 16.

Referring to FIGS. 15 to 17, if the movable member 2200 moves toward the catheter body 2100 as indicated by the arrow e2, the distance between the movable member 2200 and the catheter body 2100 may decrease. If so, distances between both ends of the plurality of support members 2400 provided between the movable member 2200 and the catheter body 2100 may decrease so that the plurality of support members 2400 may be bent at least partially. In addition, if the movable member 2200 moves toward the catheter body 2100 further, the bending portion of the support member 2400 may be gradually away from the catheter body 2100. Here, as indicated by the arrow c22 in FIG. 15, the bending portion may be regarded as meaning an apex of the bending portion, namely a point of the bending portion of the support member 2400 at which the degree of bending is greatest, or a point of the bending portion of the support member 2400 which is located farthest from the central axis o2 of the catheter body 2100. In addition, here, the bending portion moving away from the catheter body 2100 means that the bending direction of the bending portion is formed toward the outside of the catheter body, so that the bending portion moves away from the central axis o2 of the catheter body 2100. In addition, if the bending portion of the support member 2400 gradually moves away from the catheter body 2100, the bending portion may have a gradually decreasing bending angle.

Since the support member 2400 should form a bending portion according to the movement of the movable member 2200, the support member 2400 may be made of material which may be bent when a distance between both ends thereof decreases. For example, the support member 2400 may be made of metal or polymer. However, the present disclosure is not limited to such specific materials of the support member 2400, and the support member 2400 may be made of various materials which may form a partial bending portion.

Meanwhile, the electrode 2500 is provided at the bending portion c22 of the plurality of support members 2400. For example, as shown in the embodiment of FIGS. 13 to 16, the electrode 2500 may be provided at each bending portion c22 of the plurality of support members 2400.

The electrode 2500 may be connected to an energy supplying unit (not shown) through the lead wire 2600 to generate heat. In addition, the heat generated by the electrode 2500 may ablate surrounding tissues. For example, the electrode 2500 may ablate nerves around a blood vessel by generating heat of about 40° C. or above, preferably 40 to 80° C., and thus the nerves may be blocked. However, the temperature of the heat generated by the electrode 2500 may be set in various ways according to the use or purpose of the catheter.

The electrode 2500 may apply heat to nerve tissues around a blood vessel in contact with a wall of the blood vessel, and thus the electrode 2500 is preferably closely adhered to the wall of the blood vessel. Therefore, the electrode 2500 may have a curved shape, for example a circular, semicircular or oval shape, to conform to the shape of the inner wall of the blood vessel. In this embodiment, the electrode 2500 may be more clearly adhered to the wall of the blood vessel, and thus the heat generated by the electrode 2500 may be efficiently transferred to nerve tissues around the blood vessel.

Meanwhile, the electrode 2500 may be provided at a point of the bending portion of the support member 2400 which is farthest from the central axis o2 of the catheter body 2100. In other words, if the distance between the movable member 2200 and the terminal 2110 of the catheter body decreases to form a bending portion in the support member 2400, the electrode 2500 may be provided at an apex of the bending portion which is located farthest from the central axis o2 of the catheter body 2100. In this embodiment, by protruding the electrode 2500 from the catheter body 2100 to the maximum, a contact force of the electrode 2500 to the wall of the blood vessel may be further improved.

The electrode 2500 may be made of material such as platinum or stainless steel, but the present disclosure is not limited to such specific materials of the electrode 2500. The electrode 2500 may be made of various materials in consideration of various factors such as a heat generation method and an operation target.

Preferably, the electrode 2500 may generate heat by means of radio frequency (RF). For example, the electrode 2500 may be connected to a high frequency generating unit through the lead wire 2600 and emits high frequency energy to ablate nerves.

Meanwhile, the electrode 2500 provided at the catheter may be a negative electrode, and a positive electrode corresponding to the negative electrode may be connected to an energy supplying unit such as a high frequency generating unit, similar to the negative electrode, and attached to a specific portion of a human body in the form or patch or the like.

Since the electrode 2500 is provided at the bending portion of the support member 2400, when the distance between the catheter body 2100 and the movable member 2200 decreases due to the movement of the movable member 2200, the electrode 2500 may move away from the central axis o2 of the catheter body 2100. Meanwhile, if the movable member 2200 moves to increase the distance between the catheter body 2100 and the movable member 2200, the electrode 2500 provided at the bending portion may move close to the central axis o2 of the catheter body 2100.

For example, as shown in FIG. 15, if the movable member 2200 moves along the arrow e2, the bending portion gradually moves away from the central axis o2 of the catheter body 2100, and the electrode 2500 provided at the bending portion also moves in a direction away from the central axis o2 of the catheter body 2100, as indicated by the arrows f21, f22 and f23. On the contrary, if the movable member 2200 moves in a direction opposite to the arrow e2 of FIG. 15, the electrode 2500 provided at the bending portion of the support member 2400 may be configured to move close to the catheter body 2100 again.

In other words, according to the movement of the movable member 2200, the electrode 2500 may move toward the outside of the catheter body 2100 or into the catheter body 2100, based on the central axis o2 of the catheter body 2100 in the longitudinal direction.

For this, the support member 2400 having the electrode 2500 at the bending portion thereof to support the electrode 2500 may have suitable material or shape so that the electrode 2500 may move closer to or farther from the central axis o2 of the catheter body 2100 according to the movement of the movable member 2200.

For example, as indicated by the arrow c21 in FIG. 14, the support member 2400 may have a curved portion formed at least partially. In other words, even in a state in which the distance between the movable member 2200 and the catheter body 2100 is greatest, the support member 2400 may not be perfectly flat but slightly bent in the curved portion. In this case, if the movable member 2200 moves to decrease the distance between both ends of the support member 2400, the degree of bending of the curved portion c21 increases, which may form a bending portion c22. Therefore, in this embodiment, the bending portion c22 may be formed in a region where the curved portion c21 of the support member 2400 is formed.

In addition, the support member 2400 may be pre-shaped so that the bending portion does not move toward the central axis of the catheter body 2100 but moves away from the central axis of the catheter body 2100. For example, the support member 2400 may be pre-shaped to have the shape as shown in FIGS. 15 and 16 when the distance between both ends of the support member 2400 decreases.

In this case, the support member 2400 may also be made of a shape memory alloy such as nitinol. In this embodiment, the support member 2400 may be configured so that when the distance between the movable member 2200 and the catheter body 2100 decreases, the bending portion moves away from the catheter body 2100 according to the memorized shape.

In addition, the bending portion of the support member 2400 may be provided by forming a notch at a predetermined portion of the support member 2400. In this case, if the distance between both ends of the support member 2400 decreases, a bending portion may be formed at a portion of the support member 2400 where the notch is formed. In this embodiment, by adjusting a direction of the notch, the bending portion may move away from the catheter body 2100 when the distance between both ends of the support member 2400 decreases.

As described above, in the catheter for denervation according to the present disclosure, the electrode 2500 is provided at the bending portion of the support member 2400 to move close to or away from the catheter body 2100. Therefore, if the catheter according to the present disclosure is used to perform denervation, in a state in which the bending portion of the support member 2400 having the electrode 2500 is close to the catheter body 2100, the distal end of the catheter, namely the catheter tip, may be moved to a target for operation through the blood vessel. In addition, if the catheter tip reaches the operation target, by moving the bending portion of the support member 2400 having the electrode 2500 away from the catheter body 2100, the electrode 2500 may contact or approach the inner wall of the blood vessel. In addition, in this state, by emitting energy for generating heat, for example high frequency energy, through the electrode 2500, nerves around the blood vessel may be blocked. After that, if the denervation is completed with the energy emitted through the electrode 2500, the bending portion of the support member 2400 having the electrode 2500 moves again close to the catheter body 2100, and then the catheter may be extracted from the blood vessel or moved to another location.

Meanwhile, in a state in which the electrode 2500 moves away from the central axis of the catheter body 2100, the distance between the electrode 2500 and the central axis of the catheter body 2100 may be selected in various ways according to a size of an operation target, for example an inner diameter of the blood vessel. For example, in a state in which the electrode 2500 moves farthest away from the central axis of the catheter body 2100, a distance between each electrode 2500 and the central axis of the catheter body 2100 may be 2 mm to 4 mm.

The lead wire 2600 is respectively electrically connected to the plurality of electrodes 2500 to give a power supply path to the plurality of electrodes 2500. In other words, the lead wire 2600 is connected between the electrode 2500 and the energy supplying unit so that the energy supplied from the energy supplying unit is transferred to the electrode 2500. For example, one end of the lead wire 2600 is connected to the high frequency generating unit and the other end thereof is connected to the electrode 2500 so that the energy generated by the high frequency generating unit is transferred to the electrode 2500, thereby allowing the electrode 2500 to generate heat by high frequency.

The lead wire 2600 may be attached to an upper or lower portion of the support member 2400 or provided in the support member 2400, between the terminal 2110 of the catheter body and the electrode 2500. In addition, the lead wire 2600 may not be fixed to the support member 2400 but connected to the electrode 2500 to be separated from the support member 2400.

Moreover, the lead wire 2600 may not be provided separate from the support member 2400 but implemented to be integrated with the support member 2400. For example, at least a part of the support member 2400 may be made of electrically conductive material, so that the support member 2400 may serve as the lead wire 2600 in a region between the terminal 2110 of the catheter body and the electrode 2500.

Preferably, in the present disclosure, the plurality of electrodes 2500 may be configured so that the plurality of electrodes 2500 are spaced from each other in the longitudinal direction of the catheter body 2100 in a state in which the bending portion of the support member 2400 is away from the catheter body 2100.

For example, referring to the embodiment of FIG. 15, in a state in which three electrodes 2500 move away from the catheter body 2100, as indicated by the arrows d21 and d22, the three electrodes 2500 may be configured to be spaced apart from each other by a predetermined distance in the longitudinal direction of the catheter body 2100.

If the plurality of electrodes 2500 respectively emits heat, heated portions of the blood vessel may swell toward the inside of the blood vessel, which may cause stenosis. However, if three electrodes 2500 are spaced apart from each other by a predetermined distance in the longitudinal direction of the catheter body 2100 as in this embodiment, the heated portions of the blood vessel are spaced apart from each other by a predetermined distance in the longitudinal direction of the blood vessel, thereby preventing such stenosis from occurring.

In particular, the distance between electrodes 2500 in the longitudinal direction of the catheter body 2100 as indicated by the arrows d21 and d22 may be variously set according to a size of the catheter or an operation target. For example, the catheter may be configured so that in a state in which the plurality of electrodes 2500 is far from the catheter body 2100, the distance between electrodes 2500 in the longitudinal direction of the catheter body 2100 is 0.3 to 0.8 cm. In this embodiment, it is possible to prevent stenosis of the blood vessel and minimize the problem that nerves around the blood vessel pass between the electrodes 2500 and are not ablated by the electrodes 2500.

Meanwhile, in a state in which the plurality of electrodes 2500 is far from the catheter body 2100 as in this embodiment, the electrodes 2500 may be configured to be spaced apart from each other by a predetermined distance in the longitudinal direction of the catheter body 2100 in various ways.

For example, as described above, a curved portion may be formed at the plurality of support members 2400 so that a bending portion is formed in the curved portion. In this embodiment, the curved portions of the plurality of support members 2400 may be spaced apart from each other by a predetermined distance in the longitudinal direction of the catheter body 2100.

In addition, in an embodiment in which the support member 2400 is made of a shape memory alloy, the bending portions of the plurality of support members 2400 may be spaced apart from each other by a predetermined distance in the longitudinal direction of the catheter body 2100 by using the plurality of shape-memorized support members 2400.

Also preferably, in the present disclosure, in a state in which the bending portion of the support member 2400 is far from the catheter body 2100, the plurality of electrodes 2500 may be configured to be spaced apart from each other by a predetermined angle based on the central axis of the catheter body 2100 in the longitudinal direction.

For example, as shown in FIG. 17, in a state in which three electrodes 2500 move away from the catheter body 2100 according to the movement of the movable member 2200, assuming that angles among three electrodes 2500 are g21, g22 and g23 based on the central axis o2 of the catheter, g21, g22 and g23 have predetermined angles, so that the three electrodes 2500 are spaced apart from each other by the predetermined angles. For example, g21, g22 and g23 may be identically 120°.

In addition, in an embodiment including four or more support members 2400 and four or more electrodes 2500, the plurality of electrodes 2500 may also be spaced apart from each other by predetermined angles based on the central axis o2 of the catheter.

In the embodiment in which the electrodes 2500 are spaced apart from each other by predetermined angles based on the central axis of the catheter body 2100 as described above, the electrodes 2500 may be configured to spread widely in all directions around the catheter body 2100. Therefore, even though nerves are disposed in a local portion of the blood vessel, the electrodes 2500 may cover the nerves.

FIG. 18 is a cross-sectional view schematically showing a distal end of a catheter for denervation according to another embodiment of the present disclosure, and FIG. 19 is a cross-sectional view schematically showing that an electrode 2500 moves away from the catheter body 2100 by the movement of the movable member 2200, in the configuration of FIG. 18.

Referring to FIGS. 18 and 19, the catheter for denervation according to the present disclosure may include a reinforcing member 2700.

The reinforcing member 2700 may have a rod or plate shape extending in the longitudinal direction of the catheter body 2100 and be provided between the catheter body 2100 and the movable member 2200. In addition, a distal end of the reinforcing member 2700 may be connected and fixed to the movable member 2200 to be movable according to the movement of the movable member 2200.

At this time, a through hole 2130 may be formed in the catheter body 2100, and a proximal end of the movable member 2200 may be inserted into the through hole 2130.

In this embodiment, as shown in FIG. 19, if the movable member 2200 moves in the left direction, namely toward the catheter body 2100, the reinforcing member 2700 may also move in the left direction. At this time, the proximal end of the reinforcing member 2700 is inserted into the through hole 2130 of the catheter body 2100, so that the reinforcing member 2700 may slide through the through hole 2130 according to the movement of the movable member 2200.

In this embodiment, the connection between the catheter body 2100 and the movable member 2200 may be supported by the reinforcing member 2700 more strongly. In other words, if the movable member 2200 is separated from the catheter body 2100, in case of connecting the catheter body 2100 and the movable member 2200 by using a single operating member 2300, the connection state and supporting force between the catheter body 2100 and the movable member 2200 may be weak. However, if the reinforcing member 2700 is provided separately from the operating member 2300 as in this embodiment, the supporting force to the movable member 2200 separated from the catheter body 2100 is more reinforced, and the connection state between the catheter body 2100 and the movable member 2200 may be firmly maintained. In addition, since the reinforcing member 2700 may guide movement of the movable member 2200, the moving direction of the movable member 2200 may be kept without deviating from the central axis of the catheter body 2100.

Meanwhile, even though the embodiments of FIGS. 18 and 19 illustrate that only one reinforcing member 2700 is provided, two or more reinforcing members 2700 may also be provided.

In addition, even though it is depicted in several drawings that only one operating member 2300 is provided, two or more operating members 2300 may also be provided.

Also preferably, the catheter for denervation according to the present disclosure may include a stopper 2800. The stopper 2800 limits a moving distance of the movable member 2200, and the catheter body may include at least one stopper.

More preferably, the stopper 2800 may be fixed to the operating member 2300, as shown in FIGS. 18 and 19. At this time, the stopper 2800 may include a first stopper 2810 fixed to a portion of the operating member 2300 located in the catheter body 2100 and a second stopper 2820 fixed to a portion of the operating member 2300 located out of the catheter body 2100. Here, the first stopper 2810 may limit the movement of the movable member 2200 so that the movable member 2200 does not move further in a direction away from the catheter body 2100. In addition, the second stopper 2820 may limit the movement of the movable member 2200 so that the movable member 2200 does not move further in a direction closer to the catheter body 2100.

In the embodiment including the stopper 2800 as described above, it is possible to facilitate an operator's manipulation and also prevent various components included in the catheter from being damaged. For example, in the embodiment of FIG. 18, the first stopper 2810 limits the movable member 2200 not to move further in the right direction, thereby preventing the movable member 2200 from moving excessively away from the catheter body 2100 and thus cutting the connection between the support member 2400 and the catheter body 2100 or the connection between the support member 2400 and the movable member 2200. In another example, the second stopper 2820 may limit the movable member 2200 not to move further in the left direction, thereby preventing the movable member 2200 from moving excessively close to the catheter body 2100 and thus damaging the support member 2400 or cutting the connection between the support member 2400 and the catheter body 2100 or the connection between the support member 2400 and the movable member 2200. Moreover, an operator may not pay attention to an operating distance of the operating member 2300 since the operating distance is limited by the stopper 2800 while the operating member 2300 is pushed or pulled.

FIG. 20 is a cross-sectional view schematically showing a distal end of a catheter for denervation according to another embodiment of the present disclosure, and FIG. 21 is a cross-sectional view schematically showing that an electrode 2500 moves away from the catheter body 2100 by the movement of the movable member 2200, in the configuration of FIG. 20.

Referring to FIGS. 20 and 21, the catheter body 2100 may have a guide hole 2140 formed in the distal end thereof so that a guide wire w2 may pass through. Here, the guide wire w2 is to guide the catheter to an operation target and may reach the operation target prior to the catheter. In this embodiment, the guide wire w2 may be inserted into the catheter through the guide hole 2140, and the catheter tip may reach the operation target along the guide wire w2.

The catheter body 2100 may have one or more guide hole 2140. For example, as shown in FIGS. 20 and 21, the catheter body 2100 has a first guide hole 2141 formed at the terminal thereof and a second guide hole 2142 formed at a position spaced apart from the terminal 2110 of the catheter body by a predetermined distance. In this case, the guide wire may be inserted into the inner space of the catheter body 2100 through the first guide hole 2141 and then drawn out of the catheter body 2100 through the second guide hole 2142. However, the second guide hole 2142 may not be provided, and in this case, the guide wire inserted into the inner space of the catheter body 2100 through the first guide hole 2141 may extend long along the inner space of the catheter body 2100 and then be drawn out of the catheter body 2100 at the proximal end of the catheter body 2100.

If the second guide hole 2142 is provided, the second guide hole may be located at various positions depending on various situations. In particular, the second guide hole 2142 may be formed at a point spaced apart by 10 cm to 15 cm from the terminal 2110 of the catheter body in the longitudinal direction of the catheter body. Even though FIG. 20 shows that the second guide hole 2142 is located close to the terminal 2110 of the catheter body, it is just for illustration, and the distance from the terminal of the catheter body to the second guide hole, indicated by L21, may be 10 cm to 15 cm. In this embodiment, while the catheter body is moving, it is possible to prevent the problem that the guide wire drawn from the catheter body through the second guide hole is entangled with the catheter body, thereby facilitating smooth movement of the catheter body. However, the present disclosure is not limited to such a location of the second guide hole.

Meanwhile, in this embodiment, a guide hole 2210 may also be formed in the movable member 2200 so that a guide wire may pass through.

In an embodiment in which the guide hole 2140 is formed in the catheter body 2100 as described above, since the guide wire inserted into the guide hole guides movement of the catheter tip, the catheter may smoothly reach an operation target, and the catheter may be easily manipulated. Moreover, since the catheter does not need to include a component for adjusting a moving direction of the catheter, the catheter may have a simpler structure, which is advantageous in reducing the size of the catheter.

Also preferably, the catheter for denervation according to the present disclosure may further include an elastic member 2900.

One end of the elastic member 2900 may be connected to the movable member 2200 to give a restoring force when the movable member 2200 is moving. For example, as shown in FIG. 20, the elastic member 2900 may be connected between the terminal 2110 of the catheter body and the movable member 2200. In this case, as shown in FIG. 21, if the movable member 2200 moves in the left direction so that the electrode 2500 moves away from the catheter body 2100, the restoring force, namely the elastic restoring force, of the elastic member 2900 is applied in the right direction. Therefore, after nerves are completely blocked by the electrode 2500, the movable member 2200 should move again in the right direction and return to its original state as shown in FIG. 20. Here, the movement of the movable member 2200 in the right direction may be more easily performed by means of the restoring force of the elastic member 2900. Therefore, after nerves are blocked by the electrode 2500, an operator may not give great efforts to move the electrode 2500 close to the central axis of the catheter body 2100.

In addition, in an embodiment in which the elastic member 2900 is provided as described above, it is possible to prevent the electrode 2500 from deviating from the central axis of the catheter body 2100 while the catheter tip is moving, and thus it is also possible to prevent the blood vessel from being damaged due to protrusion of the electrode 2500 and facilitate easy movement of the catheter tip. Moreover, even though the stopper 2800 is not provided, the moving distance of the movable member 2200 may be limited by the elastic member 2900, which may prevent various components from being damaged due to excessive movement of the movable member 2200.

Also preferably, the catheter for denervation according to the present disclosure may further include a temperature measuring member (not shown).

In particular, the temperature measuring member may be provided around the electrode 2500 to measure a temperature of the electrode 2500 or around the electrode 2500. In addition, the temperature measured by the temperature measuring member as described above may be used for controlling the temperature of the electrode 2500. Here, the temperature measuring member may be connected to the lead wire 2600 through a separate wire, and the separate wire may extend to the proximal end of the catheter body 2100 through the inner space of the catheter body 2100 and be drawn out of the catheter body 2100.

Meanwhile, even though various embodiments illustrate that the movable member 2200 is provided out of the catheter body 2100, the present disclosure is not limited thereto.

FIG. 22 is a cross-sectional view schematically showing a distal end of a catheter for denervation according to another embodiment of the present disclosure, and FIG. 23 is a cross-sectional view showing the catheter of FIG. 22 along the longitudinal direction. However, features to which the description in relation to the embodiment of FIGS. 13 to 21 can be applied will not be described in detail, but different features will be described in detail.

Referring to FIGS. 22 and 23, the movable member 2200 may be provided in the inner space of the catheter body 2100. In addition, the movable member 2200 may move in the lateral direction in the inner space of the catheter body 2100. Here, different from the embodiments of FIGS. 13 to 21, the proximal end of the support member 2400 may be connected and fixed to the movable member 2200, and the distal end thereof may be fixed to the terminal 2110 of the catheter body.

Since the movable member 2200 is located closer to the proximal end of the catheter in comparison to the catheter body 2100, if an operator pushes the operating member 2300, the movable member 2200 moves in the right direction of FIG. 23, so that a distance between the movable member 2200 and the terminal 2110 of the catheter body decreases. Meanwhile, if an operator pulls the operating member 2300, the movable member 2200 moves in the left direction of FIG. 23, so that the distance between the movable member 2200 and the terminal 2110 of the catheter body increases.

Even in this embodiment, if the distance between the movable member 2200 and the terminal 2110 of the catheter body decreases, the electrode 2500 provided at the bending portion of the support member 2400 may move away from the catheter body 2100, which will be described in more detail with reference to FIGS. 24 and 25.

FIG. 24 is a cross-sectional view schematically showing that the electrode 2500 moves away from the catheter body 2100 by the movement of the movable member 2200, in the configuration of FIG. 23, and FIG. 25 is a perspective view of FIG. 24.

Referring to FIGS. 24 and 25, if the movable member 2200 moves toward the terminal 2110 of the catheter body (in the right direction of FIG. 24) so that the distance between the movable member 2200 and the terminal 2110 of the catheter body decreases, a distance between both ends of the support member 2400 may decrease. Therefore, the bending portion of the support member 2400 may move away from the catheter body 2100, and the electrode 2500 provided at the bending portion move away from the catheter body 2100.

As described above, in the embodiment of FIGS. 22 to 25, the support member 2400 and the electrode 2500 located in the inner space of the catheter body 2100 may protrude toward the outside of the catheter body 2100 according to the movement of the movable member 2200. For this, the catheter body 2100 may have an opening 2150 through which the support member 2400 and the electrode 2500 may protrude outwards. In other words, if the movable member 2200 moves so that the distance between the movable member 2200 and the terminal 2110 of the catheter body decreases, the bending portion of the support member 2400 and the electrode 2500 may be drawn out of the catheter body 2100 through the opening 2150 of the catheter body 2100. Meanwhile, if the movable member 2200 moves so that the distance between the movable member 2200 and the terminal 2110 of the catheter body increases, the bending portion of the support member 2400 and the electrode 2500 may be inserted into the inner space of the catheter body 2100 through the opening 2150 of the catheter body 2100.

Meanwhile, the features of the embodiment of FIGS. 13 to 21 may also be applied to the catheter according to the embodiment of FIGS. 22 to 25. For example, in the embodiment of FIGS. 22 to 25, the plurality of electrodes 2500 may be spaced apart from each other by a predetermined length in the longitudinal direction of the catheter body 2100 in a state in which the bending portion of the support member 2400 is far from the catheter body 2100. In addition, the plurality of electrodes 2500 may also be configured to be spaced apart from each other by a predetermined angle based on the central axis of the catheter body 2100 in the longitudinal direction, in a state in which the bending portion of the support member 2400 is far from the catheter body 2100.

In addition, in the embodiment of FIGS. 22 to 25, a guide hole may also be formed in the catheter body 2100, and the catheter may also further include a stopper or an elastic member.

In particular, if the catheter includes a stopper, one or more stopper may be fixed to the catheter body 2100. In other words, since the movable member 2200 may move right or left in the inner space of the catheter body 2100 along the longitudinal direction, the stopper is provided in a left space and/or a right space of the inner space of the catheter body 2100 based on the movable member 2200 to limit the movement of the movable member 2200 in the lateral direction.

In addition, if the catheter includes an elastic member, the elastic member may be provided between the movable member 2200 and the terminal 2110 of the catheter body. In other words, the proximal end of the elastic member may be connected and fixed to the movable member 2200, and the distal end of the elastic member may be fixed to the terminal 2110 of the catheter body, so that the elastic member may give a restoring force in the left direction when the movable member 2200 moves in the right direction.

FIG. 26 is a perspective view schematically showing a distal end of a catheter for denervation according to another embodiment of the present disclosure.

Referring to FIG. 26, the catheter for denervation according to the present disclosure may further include an end tip 2950.

The end tip 2950 is provided at the front surfaces of the distal ends of the catheter body 2100 and the movable member 2200. For example, if the movable member is located closer to the distal end in comparison to the catheter body as in the embodiment of FIG. 26, the end tip 2950 may be provided at the front surface of the distal end of the movable member. However, if the terminal of the catheter body is located closer to the distal end in comparison to the movable member as in the embodiment of FIG. 22, the end tip 2950 may be provided at the front surface of the distal end of the catheter body. In other words, the end tip 2950 may be regarded as being located farther from the terminal of the catheter body and the movable member. In this case, the end tip 2950 may be a component serving as the terminal of the catheter for denervation according to the present disclosure.

Meanwhile, the end tip 2950 may be configured to be separated from the movable member or the catheter body. For example, in the configuration of FIG. 26, the end tip 2950 may be separated from the movable member. In this case, if the operating member operates to move the movable member, the end tip 2950 does not move, and the distance between the movable member and the end tip 2950 may change. However, the end tip 2950 may also be fixed to the movable member or the catheter body.

The end tip 2950 may be made of soft and flexible material. In particular, the end tip 2950 may be made of a composition containing polyether block amide (PEBA). Here, the composition for the end tip 2950 may contain other additives in addition to the polyether block amide. For example, the end tip 2950 may be made of a composition containing 70 weight % of polyether block amide and 30 weight % of barium sulfate, based on the entire weight of the composition.

In this configuration of the present disclosure, when the distal end 2101 of the catheter body moves along a blood vessel or the like, the end tip 2950 made of soft and flexible material is located at a foremost position, which may reduce damages to the blood vessel and facilitate easier change of a moving direction. Further, the end tip 2950 made of the above material may be photographed by X-ray, and thus a location of the distal end of the catheter body may be easily figured out.

Preferably, the end tip 2950 may have a hollow tube shape. In addition, the hollow of the end tip 2950 may extend in the same direction of the longitudinal direction of the catheter body. If the end tip 2950 has a tube shape as described above, a guide wire may pass through the hollow of the end tip 2950. For example, the end tip may have a tube shape with a length of 6 mm and a hollow diameter of 0.7 mm.

The end tip may extend along the longitudinal direction of the catheter body. At this time, the end tip may have different sizes along the length thereof. In particular, if the end tip has a cylindrical shape, a distal end of the end tip may have the smallest diameter in comparison to other regions. For example, the distal end of the end tip may have a smallest diameter of 1.1 mm, when the thickest region of the end tip has a diameter of 1.3 mm.

The end tip 2950 may have a suitable length, which is not too long and not too short. For example, in the configuration of FIG. 26, the length of the end tip 2950, indicated by L22, may be 5 mm to 15 mm. In this configuration, when the catheter moves along the inner space of a blood vessel or the inner space of a sheath, it is possible to prevent the movement from being disturbed by the end tip 2950. In addition, in this configuration, a shape of the blood vessel or the like at which the end tip 2950 is located may be easily figured out from a bending shape or a bending direction of the end tip 2950.

In addition, the catheter for denervation according to the present disclosure may further include a passing tube (not shown). The passing tube may have a hollow tube shape, which is included in the inner space of the catheter body, and the operating member may be located in the hollow of the passing tube. In other words, the operating member may move in a state of being inserted into the inner space of the passing tube. In this case, the passing tube may be exposed not only to the inner space of the catheter body but also to the outside. For example, in the configuration of FIG. 26, the passing tube may be provided in a space between the catheter body and the movable member. In addition, the movable member may have a ring shape which is movable while surrounding the outer circumference of the passing tube. In this configuration, a moving path of the movable member may be fixed, and a coupling force between the catheter body and the movable member may be further reinforced.

Meanwhile, even though the several embodiments have been illustrated so that three support members 2400 and three electrodes 2500 are provided, the number of support members 2400 and electrodes 2500 are not limited to the above in the present disclosure, and the number of support members 2400 and electrodes 2500 may be variously set.

In addition, even though the several embodiments have been illustrated so that a single bending portion is formed in a single support member 2400, two or more bending portions may be formed in a single support member 2400, and accordingly two or more electrodes 2500 may be provided at a single support member 2400.

A denervation apparatus according to the present disclosure includes the catheter for denervation. In addition, the denervation apparatus may further include an energy supplying unit and an opponent electrode in addition to the catheter for denervation. Here, the energy supplying unit may be electrically connected to the electrode 2500 through the lead wire 2600. In addition, the opponent electrode may be electrically connected to the energy supplying unit through a lead wire 2600 which is different from the above lead wire 2600. In this case, the energy supplying unit may supply energy to the electrode 2500 of the catheter in the form of high frequency or the like, and the electrode 2500 of the catheter generates heat to ablate nerves around the blood vessel, thereby block the nerves.

Next, a catheter for denervation according to a third aspect of the present disclosure will be described with reference to FIGS. 27 to 42.

FIG. 27 is a perspective view schematically showing a distal end of a catheter according to the third aspect of the present disclosure, and FIG. 28 is a cross-sectional view, taken along the line A31-A31' of FIG. 27. FIG. 28 shows a support member 3400, an electrode 3500 and a lead wire 3600 included in the catheter of FIG. 27 for convenience.

Here, as described above, the distal end of the catheter means an end of the catheter which reaches a portion of a human body under a surgical procedure, between both ends of the catheter extending in the longitudinal direction, and it may also be called a catheter tip. In addition, an end of the catheter opposite to the distal end may be called a proximal end. Hereinafter, regarding various components which extend in the longitudinal direction of the catheter and thus have both ends in the longitudinal direction, an end of a component, located at the distal end of the catheter, will be called a distal end of the corresponding component, and a proximal end of a component, located at the proximal end of the catheter, will be called a proximal end of the corresponding component.

Referring to FIGS. 27 and 28, the catheter according to the present disclosure may include a catheter body 3100, a movable member 3200, an operating member 3300, a support member 3400, n electrode 3500 and a lead wire 3600.

The catheter body 3100 has a pipe or tube shape extending in one direction and has an inner space therein along the longitudinal direction. Here, the catheter body 3100 has both ends along the longitudinal direction, where an end of the catheter body 3100 firstly inserted into a human body during a surgical procedure using the catheter and reaching a destination, namely a target for the surgical procedure, is called a distal end, and an end of the catheter body 3100 located near an operator and manipulated by the operator is called a proximal end (not shown), as described above.

The catheter body 3100 has a hollow tube shape and has an inner space therein along the longitudinal direction. Therefore, various components for a surgical procedure may be provided in or move through the inner space, and substances such as drugs or washing liquids may be injected through the inner space. For this, the proximal end of the catheter body 3100 may be formed so that the inner space is open to the outside.

The catheter body 3100 may have various shapes depending on its target or purpose and may also have various inner or outer diameters. In addition, the catheter body 3100 may be made of various materials, for example soft materials such as rubber and plastic or hard material such as metal. The present disclosure is not limited to a specific shape, material or size of the catheter body 3100, and the catheter body 3100 may have various shapes, materials, sizes or the like.

The movable member 3200 is provided at the distal end 3101 of the catheter body and may be configured to be movable in the longitudinal direction of the catheter body 3100. In addition, by means of the movement of the movable member 3200, a distance between the terminal 3110 of the catheter body and the movable member 3200 may increase or decrease.

In particular, as shown in FIGS. 27 and 28, the movable member 3200 may be provided out of the catheter body 3100. In other words, the movable member 3200 may be separated from the catheter body 3100 and located at an outer side in comparison to the terminal 3110 of the catheter body (in the right side in FIG. 28). In this case, if the movable member 3200 moves in the left direction, the distance between the movable member 3200 and the catheter body 3100 may decrease, and if the movable member 3200 moves in the right direction, the distance between the movable member 3200 and the catheter body 3100 may increase.

Preferably, the distal end 3101 of the catheter body and/or the movable member 3200 may be made of soft and flexible material. Since the distal end 3101 of the catheter body and the movable member 3200 are located at a front end of the catheter, when the catheter moves along a blood vessel or the like, the distal end 3101 of the catheter body and the movable member 3200 are likely to contact an inner wall of the blood vessel or the like. However, if the distal end 3101 of the catheter body and the movable member 3200 are made of such a soft and flexible material, it is possible to minimize or prevent a damage of the blood vessel or the like, caused by the distal end 3101 of the catheter body and the movable member 3200, and it is also easy to change a moving direction of the distal end 3101 of the catheter body and the movable member 3200.

In addition, in a similar way, the distal end 3101 of the catheter body and/or the movable member 3200 may have a rounded edge. In particular, as shown in the figure, the movable member 3200 may have an outer surface (the right surface in FIG. 28) which circularly protrudes toward the front end of the catheter. In addition, the inner surface (the left surface in FIG. 28) of the movable member 3200 may also have a rounded edge.

The operating member 3300 may be formed to extend long along the longitudinal direction of the catheter body 3100, and may move the movable member 3200 in the longitudinal direction. For this, one end of the operating member 3300, namely a distal end thereof, is connected and fixed to the movable member 3200, and the operating member 3300 may be located according to the inner space of the catheter body 3100. In addition, the other end of the operating member 3300, namely a proximal end thereof, may be exposed out of the catheter body 3100 through the open portion of the proximal end of the catheter body 3100. In this case, an operator may pull or push the operating member 3300 manually or automatically using a separate tool. In this case, the operating member 3300 may move in the lateral direction as indicated by the arrow b32 of FIG. 28, and by doing so, the movable member 3200 connected to one end of the operating member 3300 may move the lateral direction as indicated by the arrow b31.

Meanwhile, in the embodiment of FIG. 28, since the operating member 3300 is connected to the movable member 3200 out of the catheter body 3100, an operation hole 3120 may be formed in the catheter body 3100 so that the operating member 3300 may move through the operation hole 3120.

The support member 3400 may have a rod or plate shape extending in one direction and may be connected between the catheter body 3100 and the movable member 3200. In other words, one end of the support member 3400 may be connected to the terminal 3110 of the catheter body, namely to a farthest end of the distal end 3101 of the catheter body, and the other end thereof may be connected to the movable member 3200. For example, in the configuration of FIG. 28, the proximal end (left end) of the support member 3400 may be fixed to the outer surface of the terminal 3110 of the catheter body, and the distal end (right end) of the support member 3400 may be fixed to the left surface of the movable member 3200.

Meanwhile, as described above, the movable member 3200 may be configured to move close to or away from the terminal 3110 of the catheter body in the longitudinal direction of the catheter body 3100 by means of the operating member 3300.

In particular, in the present disclosure, if the movable member 3200 moves to decrease the distance between the terminal 3110 of the catheter body and the movable member 3200, the support member 3400 may be bent at least partially, and this bending portion may be configured to move away from the catheter body 3100. This will be described in more detail with reference to FIGS. 29 to 31.

FIG. 29 a cross-sectional view schematically showing that the bending portion of the support member 3400 moves away from the catheter body 3100 by the movement of the movable member 3200, in the configuration of FIG. 28. In addition, FIG. 30 is a perspective view of FIG. 29, and FIG. 31 is a front view of FIG. 30.

Referring to FIGS. 29 to 31, if the movable member 3200 moves toward the catheter body 3100 as indicated by the arrow g3, the distance between the movable member 3200 and the catheter body 3100 may decrease. If so, distances between both ends of the plurality of support members 3400 provided between the movable member 3200 and the catheter body 3100 may decrease so that the plurality of support members 3400 may be bent at least partially. In addition, if the movable member 3200 moves toward the catheter body 3100 further, the bending portion of the support member 3400 may be gradually away from the catheter body 3100. Here, as indicated by the arrow p3 in FIG. 29, the bending portion may be regarded as meaning an apex of the bending portion, namely a point of the bending portion of the support member 3400 at which the degree of bending is greatest, or a point of the bending portion of the support member 3400 which is located farthest from the central axis of the catheter body 3100. In addition, here, the bending portion moving away from the catheter body 3100 means that the bending direction of the bending portion p3 is formed toward the outside of the catheter body, so that the bending portion p3 moves away from the central axis of the catheter body 3100.

Since the support member 3400 should form a bending portion according to the movement of the movable member 3200, the support member 3400 may be made of material which may be bent when a distance between both ends thereof decreases. For example, the support member 3400 may be made of metal or polymer. However, the present disclosure is not limited to such specific materials of the support member 3400, and the support member 3400 may be made of various materials which may form a partial bending portion.

Meanwhile, the electrode 3500 is provided at the bending portion p3 of the plurality of support members 3400. For example, as shown in the embodiment of FIGS. 27 to 30, the electrode 3500 may be provided at each bending portion p3 of the plurality of support members 3400.

The electrode 3500 may be connected to an energy supplying unit (not shown) through the lead wire 3600 to generate heat. In addition, the heat generated by the electrode 3500 may ablate surrounding tissues. For example, the electrode 3500 may ablate nerves around a blood vessel by generating heat of about 40° C. or above, preferably 40 to 80° C., and thus the nerves may be blocked. However, the temperature of the heat generated by the electrode 3500 may be set in various ways according to the use or purpose of the catheter.

The electrode 3500 may apply heat to nerve tissues around a blood vessel in contact with a wall of the blood vessel, and thus the electrode 3500 is preferably closely adhered to the wall of the blood vessel. Therefore, the electrode 3500 may have a curved shape, for example a circular, semicircular or oval shape, to conform to the shape of the inner wall of the blood vessel. In this embodiment, the electrode 3500 may be more clearly adhered to the wall of the blood vessel, and thus the heat generated by the electrode 3500 may be efficiently transferred to nerve tissues around the blood vessel.

Meanwhile, the electrode 3500 may be provided at a point of the bending portion of the support member 3400 which is farthest from the central axis of the catheter body 3100. In other words, if the distance between the movable member 3200 and the terminal 3110 of the catheter body decreases to form a bending portion in the support member 3400, the electrode 3500 may be provided at an apex of the bending portion which is located farthest from the central axis of the catheter body 3100. In this embodiment, by protruding the electrode 3500 from the catheter body 3100 to the maximum, a contact force of the electrode 3500 to the wall of the blood vessel may be further improved.

The electrode 3500 may be made of material such as platinum or stainless steel, but the present disclosure is not limited to such specific materials of the electrode 3500. The electrode 3500 may be made of various materials in consideration of various factors such as a heat generation method and an operation target.

Preferably, the electrode 3500 may generate heat by means of radio frequency (RF). For example, the electrode 3500 may be connected to a high frequency generating unit through the lead wire 3600 and emits high frequency energy to ablate nerves.

Meanwhile, the electrode 3500 provided at the catheter may be a negative electrode, and a positive electrode corresponding to the negative electrode may be connected to an energy supplying unit such as a high frequency generating unit, similar to the negative electrode, and attached to a specific portion of a human body in the form or patch or the like.

Since the electrode 3500 is provided at the bending portion of the support member 3400, when the distance between the catheter body 3100 and the movable member 3200 decreases due to the movement of the movable member 3200, the electrode 3500 may move away from the central axis of the catheter body 3100. Meanwhile, if the movable member 3200 moves to increase the distance between the catheter body 3100 and the movable member 3200, the electrode 3500 provided at the bending portion may move close to the central axis of the catheter body 3100.

For example, as shown in FIG. 29, if the movable member 3200 moves along the arrow g3, the bending portion p3 gradually moves away from the central axis of the catheter body 3100, and the electrode 3500 provided at the bending portion also moves in a direction away from the central axis of the catheter body 3100, as indicated by the arrows h31, h32 and h33. On the contrary, if the movable member 3200 moves in a direction opposite to the arrow g3 of FIG. 29, the electrode 3500 provided at the bending portion of the support member 3400 may be configured to move close to the catheter body 3100 again.

In other words, according to the movement of the movable member 3200, the electrode 3500 may move toward the outside of the catheter body 3100 or into the catheter body 3100, based on the central axis of the catheter body 3100 in the longitudinal direction.

For this, the support member 3400 having the electrode 3500 at the bending portion thereof to support the electrode 3500 may have suitable material or shape so that the bending direction of the bending portion may move farther from the central axis of the catheter body 3100 when the distance between the movable member 3200 and the catheter body 3100 decreases, namely the distance between both ends thereof decreases.

For example, the support member 3400 may be configured so that an outer surface length of a section in the width direction is longer than an inner surface length thereof. This configuration will be described in more detail with reference to FIG. 32.

FIG. 32 is a cross-sectional view, taken along the line A32-A32' of FIG. 27. However, FIG. 32 does not depict the operating member 3300, the electrode 3500 and the lead wire 3600 but shows a single support member 3400 as an enlarged view for convenience.

Referring to FIG. 32, in view of the section cut in the width direction, the support member 3400 may be configured so that an outer surface has a greater length than an inner surface. Here, the length of the outer surface means a length of a surface located farther from the central axis of the catheter body 3100 as indicated by L31 in FIG. 32, and the length of the inner surface means a length of a surface located closer to the central axis of the catheter body 3100 as indicated by L32 in FIG. 32.

If the outer surface length L31 of the support member 3400 is longer than the inner surface length L32 as described above, when a force in the longitudinal direction is applied to the support member 3400, the support member 3400 may be bent from the inner surface toward the outer surface. In other words, in this embodiment, when the movable member 3200 moves so that the distance between both ends of the support member 3400 decreases, each support member 3400 may have a bending direction moving away from the central axis of the catheter body 3100, as indicated by the arrows 131, 132 and 133 in FIG. 32. Therefore, if the distance between the catheter body 3100 and the movable member 3200 decreases, the electrode 3500 provided at the bending portion of the support member 3400 may move away from the catheter body 3100, as shown in FIGS. 29 and 30.

As another example, the support member 3400 may have a curved portion formed at least partially in a direction away from the central axis of the catheter body 3100. In other words, even in a state in which the distance between the movable member 3200 and the catheter body 3100 is greatest, the support member 3400 may not be perfectly flat but have a portion bent outwards. In this case, if the movable member 3200 moves to decrease the distance between both ends of the support member 3400, the degree of bending of the curved portion increases, which may form a bending portion, and the bending portion may have a bending direction toward the outside of the catheter body 3100. In addition, if the movable member 3200 moves further, the bending portion may gradually move away from the catheter body 3100.

In addition, the support member 3400 may be pre-shaped so that the bending portion does not move toward the central axis of the catheter body 3100 but moves away from the central axis of the catheter body 3100, when the distance between the movable member 3200 and the catheter body 3100 decreases. For example, the support member 3400 may be pre-shaped to have the shape as shown in FIGS. 29 and 30 when the distance between both ends of the support member 3400 decreases.

In this case, the support member 3400 may also be made of a shape memory alloy such as nitinol. In this embodiment, the support member 3400 may be configured so that when the distance between the movable member 3200 and the catheter body 3100 decreases, the bending portion moves away from the catheter body 3100 according to the memorized shape.

In addition, the bending portion of the support member 3400 may be provided by forming a notch at a predetermined portion of the support member 3400. In this case, if the distance between both ends of the support member 3400 decreases, a bending portion may be formed at a portion of the support member 3400 where the notch is formed. In this embodiment, by adjusting a direction of the notch, the bending portion may move away from the catheter body 3100 when the distance between both ends of the support member 3400 decreases.

As described above, in the catheter for denervation according to the present disclosure, the electrode 3500 is provided at the bending portion of the support member 3400 to move close to or away from the catheter body 3100. Therefore, if the catheter according to the present disclosure is used to perform denervation, in a state in which the bending portion of the support member 3400 having the electrode 3500 is close to the catheter body 3100, the distal end of the catheter, namely the catheter tip, may be moved to a target for operation through the blood vessel. In addition, if the catheter tip reaches the operation target, by moving the bending portion of the support member 3400 having the electrode 3500 away from the catheter body 3100, the electrode 3500 may contact or approach the inner wall of the blood vessel. In addition, in this state, by emitting energy for generating heat, for example high frequency energy, through the electrode 3500, nerves around the blood vessel may be blocked. After that, if the denervation is completed with the energy emitted through the electrode 3500, the bending portion of the support member 3400 having the electrode 3500 moves again close to the catheter body 3100, and then the catheter may be extracted from the blood vessel or moved to another location.

Meanwhile, in a state in which the electrode 3500 moves away from the central axis of the catheter body 3100, the distance between the electrode 3500 and the central axis of the catheter body 3100 may be selected in various ways according to a size of an operation target, for example an inner diameter of the blood vessel. For example, in a state in which the electrode 3500 moves farthest away from the central axis of the catheter body 3100, a distance between each electrode 3500 and the central axis of the catheter body 3100 may be 2 mm to 4 mm.

The lead wire 3600 is respectively electrically connected to the plurality of electrodes 3500 to give a power supply path to the plurality of electrodes 3500. In other words, the lead wire 3600 is connected between the electrode 3500 and the energy supplying unit so that the energy supplied from the energy supplying unit is transferred to the electrode 3500. For example, one end of the lead wire 3600 is connected to the high frequency generating unit and the other end thereof is connected to the electrode 3500 so that the energy generated by the high frequency generating unit is transferred to the electrode 3500, thereby allowing the electrode 3500 to generate heat by high frequency.

The lead wire 3600 may be attached to an upper or lower portion of the support member 3400 or provided in the support member 3400, between the terminal 3110 of the catheter body and the electrode 3500. In addition, the lead wire 3600 may not be fixed to the support member 3400 but connected to the electrode 3500 to be separated from the support member 3400.

Moreover, the lead wire 3600 may not be provided separate from the support member 3400 but implemented to be integrated with the support member 3400. For example, at least a part of the support member 3400 may be made of electrically conductive material, so that the support member 3400 may serve as the lead wire 3600 in a region between the terminal 3110 of the catheter body and the electrode 3500.

In particular, in the catheter according to the present disclosure, at least one of the catheter body 3100 and the movable member 3200 connected to both ends of the support member 3400 may be configured so that connection points connected to the support member 3400 are spaced apart by a predetermined distance in the longitudinal direction of the catheter body 3100.

In more detail, referring to FIG. 28, proximal ends (left ends) of the plurality of support members 3400 are connected and fixed to an outer surface (right surface) of the terminal 3110 of the catheter body, and the connection points are respectively designated by $c31$, $c32$ and $c33$. At this time, the connection points $c31$, $c32$ and $c33$ of the support members 3400 with respect to the catheter body 3100 may be spaced apart from each other by a predetermined distance, as indicated by $f31$ and $f32$. In other words, the catheter body 3100 may be configured so that connection points of proximal ends of at least two support members 3400 are spaced apart from each other by a predetermined distance in the longitudinal direction of the catheter body 3100 (in the lateral direction of FIG. 28).

In addition, referring to FIG. 28, distal ends (right ends) of the plurality of support members 3400 are connected and fixed to an inner surface (left surface) of the movable member 3200, and the connection points are respectively designated by $e31$, $e32$ and $e33$. At this time, the connection points $e31$, $e32$ and $e33$ of the support members 3400 with respect to the movable member 3200 may be spaced apart from each other by a predetermined distance, as indicated by $f33$ and $f34$. In other words, the movable member 3200 may be configured so that connection points of distal ends of at least two support members 3400 are spaced apart from each other by a predetermined distance in the longitudinal direction of the catheter body 3100.

In order to space the connection points of the support members 3400 from each other, as shown in FIG. 28, at least one of the catheter body 3100 and the movable member 3200 may have a step formed at a surface thereof to which the support members 3400 are connected. For example, if three support members 3400 are connected to the outer surface of the terminal 3110 of the catheter body, the outer surface of the terminal 3110 of the catheter body may have three stages formed by steps.

As described above, in the catheter of the present disclosure, since the connection points of the support members 3400 are spaced apart from each other by a predetermined distance in the longitudinal direction of the catheter body 3100, if the distance between the movable member 3200 and the catheter body 3100 decreases so that the electrodes 3500 move away from the catheter body 3100, the electrodes 3500 may be spaced apart from each other in the longitudinal direction of the catheter body 3100.

In other words, if the distance between the catheter body 3100 and the movable member 3200 decreases so that the distance between both ends of the support member 3400 decreases, the support member 3400 may be bent. At this time, as shown in FIG. 29, the bending portion is likely to be formed at a central portion of the support member 3400 in the longitudinal direction. Therefore, if a step is formed with respect to the movable member 3200 and the catheter body 3100 as in this embodiment, the central portions of the support members 3400 may be spaced apart from each other in the longitudinal direction of the catheter body 3100. In addition, if the electrodes 3500 are provided at the center portions of the support members 3400, the electrodes 3500 may be spaced apart from each other in the longitudinal direction of the catheter body 3100. In particular, if the distance between the catheter body 3100 and the movable member 3200 decreases so that the electrode 3500 moves away from the catheter body 3100, the plurality of electrodes 3500 may be spaced apart from each other in the longitudinal direction of the catheter body 3100, as indicated by d31 and d32 in FIG. 29.

As described above, according to an embodiment of the present disclosure, the distance between the catheter body 3100 and the movable member 3200 decreases so that the electrode 3500 moves away from the catheter body 3100, the electrodes 3500 may be spaced apart from each other in the longitudinal direction of the catheter body 3100, thereby preventing stenosis. In other words, if the plurality of electrodes 3500 respectively emits heat, heated portions of the blood vessel may swell toward the inside of the blood vessel. At this time, if the distance between the electrodes 3500 is short in the longitudinal direction of the blood vessel, stenosis may occur. However, in the present disclosure, since the plurality of electrodes 3500 are spaced apart from each other by a predetermined distance in the longitudinal direction of the catheter body 3100, the heated portions of the blood vessel are spaced apart by a predetermined distance in the longitudinal direction of the blood vessel. Therefore, even though heat is applied to ablate nerves around a blood vessel by using the catheter of the present disclosure, it is possible to prevent stenosis from occurring at the corresponding portion.

Preferably, in an embodiment in which connection points of the catheter body 3100 and the movable member 3200 with respect to the support members 3400 are spaced apart from each other, surfaces of the catheter body 3100 and the movable member 3200 which face each other may be matched with each other. Here, matching the facing surfaces of the catheter body 3100 and the movable member 3200 means that when the catheter body 3100 and the movable member 3200 are moved to approach each other, their surfaces facing each other are substantially in agreement.

For example, as shown in FIG. 28, if steps are formed at the outer surface of the catheter body 3100 and the inner surface of the movable member 3200, the step formed at the catheter body 3100 may be matched with the step formed at the movable member 3200. In this case, differences in distances f31 and f32 between the connection points of the catheter body 3100 may be substantially identical to differences in distances f33 and f34 between the connection points of the movable member 3200.

In this embodiment, the plurality of support members 3400 may be configured to have the same length, and the electrode 3500 may be provided at a center portion of each support member 3400 in the longitudinal direction. In this case, as shown in FIG. 29, if the distance between the catheter body 3100 and the movable member 3200 decreases so that the electrode 3500 moves away from the catheter body 3100, the distance d31 between the electrodes 3500 may be substantially identical to f31 (=f33), and the d32 distance between the electrodes 3500 may be substantially identical to f32 (=f34).

Therefore, if the facing surfaces of the catheter body 3100 and the movable member 3200 are configured to be matched with each other, the distance between them may be controlled by adjusting a difference in distances between the connection points when the electrodes 3500 are far from the catheter body 3100. Therefore, in this configuration, the distance between the electrodes 3500 may be easily adjusted.

Here, when the distance between the movable member 3200 and the catheter body 3100 decreases, namely when the electrode 3500 moves away from the catheter body 3100, the distance d31 and d32 between the electrodes 3500 may be variously selected depending on a size of the catheter or an operation target. For example, the catheter may be configured so that in a state in which the plurality of electrodes 3500 is far from the catheter body 3100, the distance between the electrodes 3500 in the longitudinal direction of the catheter body 3100 is 0.3 to 0.8 cm. In this embodiment, it is possible to prevent stenosis of the blood vessel and minimize the problem that nerves around the blood vessel pass between the electrodes 3500 and are not ablated by the electrodes 3500.

The support member 3400 may have a predetermined curved portion or notch formed at a location where a bending portion is to be formed, for facilitating easier formation of the bending portion. For example, the support member 3400 may include the electrode 3500 at the center portion in the longitudinal direction, and a predetermined curved portion may be formed at the center portion so that the bending portion is to be formed at the center portion.

Meanwhile, in the embodiment of FIGS. 27 to 30, steps are formed at the surfaces of the catheter body 3100 and the movable member 3200, so that the connection points with respect to the plurality of support members 3400 are spaced apart from each other by a predetermined distance in the longitudinal direction of the catheter body 3100. However, the present disclosure is not limited thereto, and in order to space the connection points with respect to the plurality of support members 3400 apart from each other, the catheter body 3100 and the movable member 3200 may be configured in various shapes.

FIG. 33 is a cross-sectional view schematically showing a distal end of a catheter for denervation according to another embodiment of the present disclosure.

Referring to FIG. 33, the catheter body 3100 and the movable member 3200 may have an inclination at their surfaces connected to the support member 3400. In other words, the outer surface of the terminal 3110 of the catheter body connected to the proximal end of the support member 3400 and the inner surface of the movable member 3200 connected to the distal end of the support member 3400 may be formed to be inclined downwards.

In particular, as shown in the figures, the surface of the catheter body 3100 having an inclination and the surface of the movable member 3200 having an inclination may have the same inclination pattern so that they may be matched with each other. In this case, the plurality of support members 3400 may have the same length, and the electrodes 3500 may be respectively located at the center portion of the support members 3400.

In this embodiment, if the distance between the catheter body 3100 and the movable member 3200 decreases, a bending portion may be formed at the center portion of the support member 3400. At this time, since ends of the support members 3400 are spaced apart from each other, the bending portions of the support members 3400 may also be spaced apart from each other. Therefore, if the distance between the catheter body 3100 and the movable member 3200 decreases so that the support member 3400 is bent, the plurality of electrodes 3500 may move away from the catheter body 3100 in a state of being spaced apart from each other by a predetermined distance in the longitudinal direction of the catheter body 3100.

Meanwhile, in the embodiment of FIGS. 28 and 33, it has been illustrated that connection points of both the catheter body 3100 and the movable member 3200 with respect to at least two support members 3400 are spaced apart from each other by a predetermined distance in the longitudinal direction of the catheter body 3100, but the present disclosure is not limited thereto. For example, it is also possible that a surface of either the catheter body 3100 or the movable member 3200, which is connected to the support member 3400, may have a step or an inclination.

Preferably, in the present disclosure, the plurality of electrodes 3500 may be configured to be spaced apart from each other by a predetermined angle based on the central axis of the catheter body 3100 in the longitudinal direction, in a state in which the bending portion of the support member 3400 is far from the catheter body 3100.

For example, as shown in FIG. 31, in a state in which three electrodes 3500 move away from the catheter body 3100 by the movement of the movable members 3200, assuming that angles among three electrodes 3500 are J31, J32 and J33 based on the central axis o3 of the catheter, J31, J32 and J33 have predetermined angles, so that the three electrodes 3500 are spaced apart from each other by the predetermined angles. For example, J31, J32 and J33 may be identically 120°

In addition, in an embodiment including four or more support members 3400 and four or more electrodes 3500, the plurality of electrodes 3500 may also be spaced apart from each other by predetermined angles based on the central axis o3 of the catheter.

In the embodiment in which the electrodes 3500 are spaced apart from each other by predetermined angles based on the central axis o3 of the catheter body 3100 as described above, the electrodes 3500 may be configured to spread widely in all directions around the catheter body 3100. Therefore, even though nerves are disposed in a local portion of the blood vessel, the electrodes 3500 may cover the nerves.

FIG. 34 is a cross-sectional view schematically showing a distal end of a catheter for denervation according to another embodiment of the present disclosure, and FIG. 35 is a cross-sectional view schematically showing that an electrode 3500 moves away from the catheter body 3100 by the movement of the movable member 3200, in the configuration of FIG. 34.

Referring to FIGS. 34 and 35, the catheter for denervation according to the present disclosure may include a reinforcing member 3700.

The reinforcing member 3700 may have a rod or plate shape extending in the longitudinal direction of the catheter body 3100 and be provided between the catheter body 3100 and the movable member 3200. In addition, a distal end of the reinforcing member 3700 may be connected and fixed to the movable member 3200 to be movable according to the movement of the movable member 3200.

At this time, a through hole 3130 may be formed in the catheter body 3100, and a proximal end of the movable member 3200 may be inserted into the through hole 3130.

In this embodiment, as shown in FIG. 35, if the movable member 3200 moves in the left direction, namely toward the catheter body 3100, the reinforcing member 3700 may also move in the left direction. At this time, the proximal end of the reinforcing member 3700 is inserted into the through hole 3130 of the catheter body 3100, so that the reinforcing member 3700 may slide through the through hole 3130 according to the movement of the movable member 3200.

In this embodiment, the connection between the catheter body 3100 and the movable member 3200 may be supported by the reinforcing member 3700 more strongly. In other words, if the movable member 3200 is separated from the catheter body 3100, in case of connecting the catheter body 3100 and the movable member 3200 by using a single operating member 3300, the connection state and supporting force between the catheter body 3100 and the movable member 3200 may be weak. However, if the reinforcing member 3700 is provided separately from the operating member 3300 as in this embodiment, the supporting force to the movable member 3200 separated from the catheter body 3100 is more reinforced, and the connection state between the catheter body 3100 and the movable member 3200 may be firmly maintained. In addition, since the reinforcing member 3700 may guide movement of the movable member 3200, the moving direction of the movable member 3200 may be kept without deviating from the central axis of the catheter body 3100.

Meanwhile, even though the embodiments of FIGS. 34 and 35 illustrate that only one reinforcing member 3700 is provided, two or more reinforcing members 3700 may also be provided.

In addition, even though it is depicted in several drawings that only one operating member 3300 is provided, two or more operating members 3300 may also be provided.

Also preferably, the catheter for denervation according to the present disclosure may include a stopper 3800. The stopper 3800 limits a moving distance of the movable member 3200, and the catheter body may include at least one stopper.

More preferably, the stopper 3800 may be fixed to the operating member 3300, as shown in FIGS. 34 and 35. At this time, the stopper 3800 may include a first stopper 3810 fixed to a portion of the operating member 3300 located in the catheter body 3100 and a second stopper 3820 fixed to a portion of the operating member 3300 located out of the catheter body 3100. Here, the first stopper 3810 may limit the movement of the movable member 3200 so that the movable member 3200 does not move further in a direction away from the catheter body 3100. In addition, the second stopper 3820 may limit the movement of the movable member 3200 so that the movable member 3200 does not move further in a direction closer to the catheter body 3100.

In the embodiment including the stopper 3800 as described above, it is possible to facilitate an operator's manipulation and also prevent various components included in the catheter from being damaged. For example, in the embodiment of FIG. 34, the first stopper 3810 limits the movable member 3200 not to move further in the right direction, thereby preventing the movable member 3200 from moving excessively away from the catheter body 3100 and thus cutting the connection between the support member 3400 and the catheter body 3100 or the connection between the support member 3400 and the movable member 3200. In another example, the second stopper 3820 may limit the movable member 3200 not to move further in the left direction, thereby preventing the movable member 3200 from moving excessively close to the catheter body 3100 and thus damaging the support member 3400 or cutting the connection between the support member 3400 and the catheter body 3100 or the connection between the support member 3400 and the movable member 3200. Moreover, an operator may not pay attention to an operating distance of the operating member 3300 since the operating distance is limited by the stopper 3800 while the operating member 3300 is pushed or pulled.

FIG. 36 is a cross-sectional view schematically showing a distal end of a catheter for denervation according to another embodiment of the present disclosure, and FIG. 37 is a cross-sectional view schematically showing that an electrode 3500 moves away from the catheter body 3100 by the movement of the movable member 3200, in the configuration of FIG. 36.

Referring to FIGS. 36 and 37, the catheter body 3100 may have a guide hole 3140 formed in the distal end thereof so that a guide wire W3 may pass through. Here, the guide wire W3 is to guide the catheter to an operation target and may reach the operation target prior to the catheter. In this embodiment, the guide wire W3 may be inserted into the catheter through the guide hole 3140, and the catheter tip may reach the operation target along the guide wire W3.

The catheter body 3100 may have one or more guide hole 3140. For example, as shown in FIGS. 36 and 37, the catheter body 3100 has a first guide hole 3141 formed at the terminal thereof and a second guide hole 3142 formed at a position spaced apart from the terminal 3110 of the catheter body by a predetermined distance. In this case, the guide wire may be inserted into the inner space of the catheter body 3100 through the first guide hole 3141 and then drawn out of the catheter body 3100 through the second guide hole 3142. However, the second guide hole 3142 may not be provided, and in this case, the guide wire inserted into the inner space of the catheter body 3100 through the first guide hole 3141 may extend long along the inner space of the catheter body 3100 and then be drawn out of the catheter body 3100 at the proximal end of the catheter body 3100.

If the second guide hole 3142 is provided, the second guide hole may be located at various positions depending on various situations. In particular, the second guide hole 3142 may be formed at a point spaced apart by 10 cm to 15 cm from the terminal 3110 of the catheter body in the longitudinal direction of the catheter body. Even though FIG. 36 shows that the second guide hole 3142 is located close to the terminal 3110 of the catheter body, it is just for illustration, and the distance from the terminal of the catheter body to the second guide hole, indicated by L33, may be 10 cm to 15 cm. In this embodiment, while the catheter body is moving, it is possible to prevent the problem that the guide wire drawn from the catheter body through the second guide hole is entangled with the catheter body, thereby facilitating smooth movement of the catheter body. However, the present disclosure is not limited to such a location of the second guide hole.

Meanwhile, in this embodiment, a guide hole 3210 may also be formed in the movable member 3200 so that a guide wire may pass through.

In an embodiment in which the guide hole 3140 is formed in the catheter body 3100 as described above, since the guide wire inserted into the guide hole guides movement of the catheter tip, the catheter may smoothly reach an operation target, and the catheter may be easily manipulated. Moreover, since the catheter does not need to include a component for adjusting a moving direction of the catheter, the catheter may have a simpler structure, which is advantageous in reducing the size of the catheter.

Also preferably, the catheter for denervation according to the present disclosure may further include an elastic member 3900.

One end of the elastic member 3900 may be connected to the movable member 3200 to give a restoring force when the movable member 3200 is moving. For example, as shown in FIG. 36, the elastic member 3900 may be connected between the terminal 3110 of the catheter body and the movable member 3200. In this case, as shown in FIG. 37, if the movable member 3200 moves in the left direction so that the electrode 3500 moves away from the catheter body 3100, the restoring force, namely the elastic restoring force, of the elastic member 3900 is applied in the right direction. Therefore, after nerves are completely blocked by the electrode 3500, the movable member 3200 should move again in the right direction and return to its original state as shown in FIG. 36. Here, the movement of the movable member 3200 in the right direction may be more easily performed by means of the restoring force of the elastic member 3900. Therefore, after nerves are blocked by the electrode 3500, an operator may not give great efforts to move the electrode 3500 close to the central axis of the catheter body 3100.

In addition, in an embodiment in which the elastic member 3900 is provided as described above, it is possible to prevent the electrode 3500 from deviating from the central axis of the catheter body 3100 while the catheter tip is moving, and thus it is also possible to prevent the blood vessel from being damaged due to protrusion of the electrode 3500 and facilitate easy movement of the catheter tip. Moreover, even though the stopper 3800 is not provided, the moving distance of the movable member 3200 may be limited by the elastic member 3900, which may prevent various components from being damaged due to excessive movement of the movable member 3200.

Also preferably, the catheter for denervation according to the present disclosure may further include a temperature measuring member (not shown).

In particular, the temperature measuring member may be provided around the electrode 3500 to measure a temperature of the electrode 3500 or around the electrode 3500. In addition, the temperature measured by the temperature measuring member as described above may be used for controlling the temperature of the electrode 3500. Here, the temperature measuring member may be connected to the lead wire 3600 through a separate wire, and the separate wire may extend to the proximal end of the catheter body 3100 through the inner space of the catheter body 3100 and be drawn out of the catheter body 3100.

Meanwhile, even though various embodiments illustrate that the movable member 3200 is provided out of the catheter body 3100, the present disclosure is not limited thereto.

FIG. 38 is a cross-sectional view schematically showing a distal end of a catheter for denervation according to another embodiment of the present disclosure, and FIG. 39 is a cross-sectional view showing the catheter of FIG. 38 along the longitudinal direction. However, features to which the description in relation to the embodiment of FIGS. 27 to 37 can be applied will not be described in detail, but different features will be described in detail.

Referring to FIGS. 38 and 39, the movable member 3200 may be provided in the inner space of the catheter body 3100. In addition, the movable member 3200 may move in the lateral direction in the inner space of the catheter body 3100. Here, different from the embodiments of FIGS. 27 to 37, the proximal end of the support member 3400 may be connected and fixed to the movable member 3200, and the distal end thereof may be fixed to the terminal 3110 of the catheter body.

In addition, in this embodiment, a configuration for making a difference in distances between the connection points of the support members 3400, for example a step or an inclination, may be formed at the outer surface (the right surface in FIG. 39) of the movable member 3200 and/or the inner surface (the left surface in FIG. 39) of the terminal 3110 of the catheter body.

Since the movable member 3200 is located closer to the proximal end of the catheter in comparison to the catheter body 3100, if an operator pushes the operating member 3300, the movable member 3200 moves in the right direction of FIG. 39, so that a distance between the movable member 3200 and the terminal 3110 of the catheter body decreases. Meanwhile, if an operator pulls the operating member 3300, the movable member 3200 moves in the left direction of FIG. 39, so that the distance between the movable member 3200 and the terminal 3110 of the catheter body increases.

Even in this embodiment, if the distance between the movable member 3200 and the terminal 3110 of the catheter body decreases, the electrode 3500 provided at the bending portion of the support member 3400 may move away from the catheter body 3100, which will be described in more detail with reference to FIGS. 40 and 41.

FIG. 40 is a cross-sectional view schematically showing that the electrode 3500 moves away from the catheter body 3100 by the movement of the movable member 3200, in the configuration of FIG. 39, and FIG. 41 is a perspective view of FIG. 40.

Referring to FIGS. 40 and 41, if the movable member 3200 moves toward the terminal 3110 of the catheter body (in the right direction of FIG. 40) so that the distance between the movable member 3200 and the terminal 3110 of the catheter body decreases, a distance between both ends of the support member 3400 may decrease. Therefore, the bending portion of the support member 3400 may move away from the catheter body 3100, and the electrode 3500 provided at the bending portion move away from the catheter body 3100.

As described above, in the embodiment of FIGS. 38 to 41, the support member 3400 and the electrode 3500 located in the inner space of the catheter body 3100 may protrude toward the outside of the catheter body 3100 according to the movement of the movable member 3200. For this, the catheter body 3100 may have an opening 3150 through which the support member 3400 and the electrode 3500 may protrude outwards. In other words, if the movable member 3200 moves so that the distance between the movable member 3200 and the terminal 3110 of the catheter body decreases, the bending portion of the support member 3400 and the electrode 3500 may be drawn out of the catheter body 3100 through the opening 3150 of the catheter body 3100. Meanwhile, if the movable member 3200 moves so that the distance between the movable member 3200 and the terminal 3110 of the catheter body increases, the bending portion of the support member 3400 and the electrode 3500 may be inserted into the inner space of the catheter body 3100 through the opening 3150 of the catheter body 3100.

Meanwhile, the features of the embodiment of FIGS. 27 to 37 may also be applied to the catheter according to the embodiment of FIGS. 38 to 41. For example, in the embodiment of FIGS. 38 to 41, the plurality of electrodes 3500 may be spaced apart from each other by a predetermined angle based on the central axis of the catheter body 3100 in the longitudinal direction, in a state in which the bending portion of the support member 3400 is far from the catheter body 3100.

In addition, in the embodiment of FIGS. 38 to 41, a guide hole may also be formed in the catheter body 3100, and the catheter may also further include a stopper or an elastic member.

In particular, if the catheter includes a stopper, one or more stopper may be fixed to the catheter body 3100. In other words, since the movable member 3200 may move right or left in the inner space of the catheter body 3100 along the longitudinal direction, the stopper is provided in a left space and/or a right space of the inner space of the catheter body 3100 based on the movable member 3200 to limit the movement of the movable member 3200 in the lateral direction.

In addition, if the catheter includes an elastic member, the elastic member may be provided between the movable member 3200 and the terminal 3110 of the catheter body. In other words, the proximal end of the elastic member may be connected and fixed to the movable member 3200, and the distal end of the elastic member may be fixed to the terminal 3110 of the catheter body, so that the elastic member may give a restoring force in the left direction when the movable member 3200 moves in the right direction.

FIG. 42 is a perspective view schematically showing a distal end of a catheter for denervation according to another embodiment of the present disclosure.

Referring to FIG. 42, the catheter for denervation according to the present disclosure may further include an end tip 3950.

The end tip 3950 is provided at the front surfaces of the distal ends of the catheter body 3100 and the movable member 3200. For example, if the movable member is located closer to the distal end in comparison to the catheter body as in the embodiment of FIG. 42, the end tip 3950 may be provided at the front surface of the distal end of the movable member. However, if the terminal of the catheter body is located closer to the distal end in comparison to the movable member as in the embodiment of FIG. 38, the end tip 3950 may be provided at the front surface of the distal end of the catheter body. In other words, the end tip 3950 may be regarded as being located farther from the terminal of the catheter body and the movable member. In this case, the end tip 3950 may be a component serving as the terminal of the catheter for denervation according to the present disclosure.

Meanwhile, the end tip 3950 may be configured to be separated from the movable member or the catheter body. For example, in the configuration of FIG. 42, the end tip 3950 may be separated from the movable member. In this case, if the operating member operates to move the movable member, the end tip 3950 does not move, and the distance between the movable member and the end tip 3950 may change. However, the end tip 3950 may also be fixed to the movable member or the catheter body.

The end tip 3950 may be made of soft and flexible material. In particular, the end tip 3950 may be made of a composition containing polyether block amide (PEBA). Here, the composition for the end tip 3950 may contain other additives in addition to the polyether block amide. For example, the end tip 3950 may be made of a composition containing 70 weight % of polyether block amide and 30 weight % of barium sulfate, based on the entire weight of the composition.

In this configuration of the present disclosure, when the distal end 3101 of the catheter body moves along a blood vessel or the like, the end tip 3950 made of soft and flexible material is located at a foremost position, which may reduce damages to the blood vessel and facilitate easier change of a moving direction. Further, the end tip 3950 made of the above material may be photographed by X-ray, and thus a location of the distal end of the catheter body may be easily figured out.

Preferably, the end tip 3950 may have a hollow tube shape. In addition, the hollow of the end tip 3950 may extend in the same direction of the longitudinal direction of the catheter body. If the end tip 3950 has a tube shape as described above, a guide wire may pass through the hollow of the end tip 3950. For example, the end tip may have a tube shape with a length of 6 mm and a hollow diameter of 0.7 mm.

The end tip may extend along the longitudinal direction of the catheter body. At this time, the end tip may have different sizes along the length thereof. In particular, if the end tip has a cylindrical shape, a distal end of the end tip may have the smallest diameter in comparison to other regions. For example, the distal end of the end tip may have a smallest diameter of 1.1 mm, when the thickest region of the end tip has a diameter of 1.3 mm.

The end tip 3950 may have a suitable length, which is not too long and not too short. For example, in the configuration of FIG. 42, the length of the end tip 3950, indicated by L34, may be 5 mm to 15 mm. In this configuration, when the catheter moves along the inner space of a blood vessel or the inner space of a sheath, it is possible to prevent the movement from being disturbed by the end tip 3950. In addition, in this configuration, a shape of the blood vessel or the like at which the end tip 3950 is located may be easily figured out from a bending shape or a bending direction of the end tip 3950.

In addition, the catheter for denervation according to the present disclosure may further include a passing tube (not shown). The passing tube may have a hollow tube shape, which is included in the inner space of the catheter body, and the operating member may be located in the hollow of the passing tube. In other words, the operating member may move in a state of being inserted into the inner space of the passing tube. In this case, the passing tube may be exposed not only to the inner space of the catheter body but also to the outside. For example, in the configuration of FIG. 42, the passing tube may be provided in a space between the catheter body and the movable member. In addition, the movable member may have a ring shape which is movable while surrounding the outer circumference of the passing tube. In this configuration, a moving path of the movable member may be fixed, and a coupling force between the catheter body and the movable member may be further reinforced.

Meanwhile, even though the several embodiments have been illustrated so that three support members 3400 and three electrodes 3500 are provided, the number of support members 3400 and electrodes 3500 are not limited to the above in the present disclosure, and the number of support members 3400 and electrodes 3500 may be variously set.

In addition, even though the several embodiments have been illustrated so that a single bending portion is formed in a single support member 3400, two or more bending portions may be formed in a single support member 3400, and accordingly two or more electrodes 3500 may be provided at a single support member 3400.

A denervation apparatus according to the present disclosure includes the catheter for denervation. In addition, the denervation apparatus may further include an energy supplying unit and an opponent electrode in addition to the catheter for denervation. Here, the energy supplying unit may be electrically connected to the electrode 3500 through the lead wire 3600. In addition, the opponent electrode may be electrically connected to the energy supplying unit through a lead wire 3600 which is different from the above lead wire 3600. In this case, the energy supplying unit may supply energy to the electrode 3500 of the catheter in the form of high frequency or the like, and the electrode 3500 of the catheter generates heat to ablate nerves around the blood vessel, thereby block the nerves.

Next, a catheter for denervation according to a fourth aspect of the present disclosure will be described with reference to FIGS. 43 to 60.

FIG. 43 is a perspective view schematically showing a distal end of a catheter according to the fourth aspect of the present disclosure, and FIG. 44 is a cross-sectional view, taken along the line A4-A4' of FIG. 43. FIG. 44 shows a first support member, a second support member and an electrode and lead wire included in the catheter of FIG. 43 for convenience.

Here, as described above, the distal end of the catheter means an end of the catheter which reaches a portion of a human body under a surgical procedure, between both ends of the catheter extending in the longitudinal direction, and it may also be called a catheter tip. In addition, an end of the catheter opposite to the distal end may be called a proximal end. Hereinafter, regarding various components which extend in the longitudinal direction of the catheter and thus have both ends in the longitudinal direction, an end of a component, located at the distal end of the catheter, will be called a distal end of the corresponding component, and a proximal end of a component, located at the proximal end of the catheter, will be called a proximal end of the corresponding component.

Referring to FIGS. 43 and 44, the catheter according to the present disclosure may includes a catheter body 4100, a movable member 4200, an operating member 4300, an intermediate member 4400, a first stopper 4310, a first support member 4510, a second support member 4520, an electrode 4600 and a lead wire 4700.

The catheter body 4100 has a pipe or tube shape extending in one direction and has an inner space therein along the longitudinal direction. Here, the catheter body 4100 has both ends along the longitudinal direction, where an end of the catheter body 4100 firstly inserted into a human body during a surgical procedure using the catheter and reaching a destination, namely a target for the surgical procedure, is called a distal end, and an end of the catheter body 4100 located near an operator and manipulated by the operator is called a proximal end (not shown), as described above.

The catheter body 4100 has a hollow tube shape and has an inner space therein along the longitudinal direction. Therefore, various components for a surgical procedure may be provided in or move through the inner space, and substances such as drugs or washing liquids may be injected through the inner space. For this, the proximal end of the catheter body 4100 may be formed so that the inner space is open to the outside.

The catheter body 4100 may have various shapes depending on its target or purpose and may also have various inner or outer diameters. In addition, the catheter body 4100 may be made of various materials, for example soft materials such as rubber and plastic or hard material such as metal. The present disclosure is not limited to a specific shape, material or size of the catheter body 4100, and the catheter body 4100 may have various shapes, materials, sizes or the like.

The movable member 4200 is provided at the distal end 4101 of the catheter body and may be configured to be movable in the longitudinal direction of the catheter body 4100. In addition, by means of the movement of the movable member 4200, a distance between the intermediate member 4400 and the movable member 4200 may increase or decrease.

In particular, as shown in FIGS. 43 and 44, the movable member 4200 may be provided out of the catheter body 4100 together with the intermediate member 4400. In other words, the movable member 4200 and the intermediate member 4400 may be separated from the catheter body 4100 and located at an outer side in comparison to the terminal 4110 of the catheter body (in the right side in FIG. 44). In this case, if the movable member 4200 moves in the left direction, the distance between the movable member 4200 and the intermediate member 4400 may decrease, and if the movable member 4200 moves in the right direction, the distance between the movable member 4200 and the intermediate member 4400 may increase.

The operating member 4300 may be formed to extend long along the longitudinal direction of the catheter body 4100, and may move the movable member 4200 in the longitudinal direction. For this, one end of the operating member 4300, namely a distal end thereof, is connected and fixed to the movable member 4200, and the operating member 4300 may be located according to the inner space of the catheter body 4100. In addition, the other end of the operating member 4300, namely a proximal end thereof, may be exposed out of the catheter body 4100 through the open portion of the proximal end of the catheter body 4100. In this case, an operator may pull or push the operating member 4300 manually or automatically using a separate tool. In this case, the operating member 4300 may move in the lateral direction as indicated by the arrow b42 of FIG. 44, and by doing so, the movable member 4200 connected to one end of the operating member 4300 may move the lateral direction as indicated by the arrow b41.

Meanwhile, in the embodiment of FIG. 44, since the operating member 4300 is connected to the movable member 4200 out of the catheter body 4100, an operation hole 4120 may be formed in the catheter body 4100 so that the operating member 4300 may move through the operation hole 4120.

The intermediate member 4400 is provided between the terminal 4110 of the catheter body and the movable member 4200. For example, as shown in the embodiment of FIG. 44, if the intermediate member 4400 and the movable member 4200 are provided out of the catheter body 4100, the intermediate member 4400 may be located at the right of the terminal 4110 of the catheter body and at the left of the movable member 4200.

The intermediate member 4400 may be configured to be movable along the longitudinal direction of the catheter body 4100, similar to the movable member 4200. In addition, by the movement of the intermediate member 4400, the distance between the terminal 4110 of the catheter body and the intermediate member 4400 may increase or decrease.

Since the intermediate member 4400 is located between the catheter body 4100 and the movable member 4200, in an embodiment in which the intermediate member 4400 is provided out of the catheter body 4100 together with the movable member 4200, an insert hole 4401 may be formed therein through which the operating member 4300 may be inserted. In addition, the operating member 4300 may move in the lateral direction while sliding through the insert hole 4401 of the intermediate member 4400.

Since the operating member 4300 moves through the insert hole 4401 of the intermediate member 4400 as described above, the intermediate member 4400 may not move only by the movement of the operating member 4300. Therefore, in order to move the intermediate member 4400 by the movement of the operating member 4300, the catheter according to the present disclosure includes a first stopper 4310.

Regarding the first stopper 4310, if the distance between the movable member 4200 and the intermediate member 4400 decreases to a predetermined level, the operating member 4300 operates to move the intermediate member 4400.

Preferably, the first stopper 4310 may be provided at a portion of the operating member 4300 located between the movable member 4200 and the intermediate member 4400. For example, as shown in FIG. 44, the first stopper 4310 may be fixed to the operating member 4300 at a location spaced apart by a predetermined distance in the outer direction from the intermediate member 4400.

The first stopper 4310 may be configured to be hooked by the insert hole 4401 of the intermediate member 4400. For example, the first stopper 4310 may be configured so that at least its partial portion has a size greater than the diameter of the insert hole 4401 formed in the intermediate member 4400. In this case, the operating member 4300 moves to escape from the insert hole of the intermediate member 4400 to a predetermined distance, and then if a portion to which the first stopper 4310 is fixed reaches the insert hole 4401, the first stopper 4310 is hooked by the insert hole 4401. Therefore, the operating member 4300 cannot move further from the insert hole 4401 of the intermediate member 4400, and the intermediate member 4400 may move together when the operating member 4300 moves.

Like this, the first stopper 4310 limits so that the distance between the movable member 4200 and the intermediate member 4400 decreases only to a predetermined level, and after distance between the movable member 4200 and the intermediate member 4400 decreases to the predetermined level, the movable member 4200 and the intermediate member 4400 may move together while maintaining the predetermined distance.

Meanwhile, the distal end 4101 of the catheter body, the movable member 4200 and/or the intermediate member 4400 may be made of soft and flexible material. Since the distal end 4101 of the catheter body, the movable member 4200 and the intermediate member 4400 are located at a front end of the catheter, when the catheter moves along a blood vessel or the like, they are likely to contact an inner wall of the blood vessel or the like. However, if they are made of such a soft and flexible material, it is possible to minimize or prevent a damage of the blood vessel or the like, and it is also easy to change a moving direction.

In addition, in a similar way, the distal end 4101 of the catheter body, the movable member 4200 and/or the intermediate member 4400 may have a rounded edge. In particular, as shown in FIG. 43, if the movable member 4200 is located at a foremost position, the movable member 4200 may have an outer surface (the right surface in FIG. 44) which circularly protrudes toward the front end of the catheter. In addition, the movable member 4200 may also have an inner surface (the left surface in FIG. 44) which has a rounded edge. In addition, an edge of an inner or outer surface of the intermediate member 4400 and an edge of the terminal 4110 of the catheter body may also have a rounded shape.

The first support member 4510 may have a rod or plate shape extending in one direction and may be connected between the intermediate member 4400 and the movable member 4200. In other words, one end of the first support member 4510 may be connected to the intermediate member 4400, the other end thereof may be connected to the movable member 4200. For example, in the configuration of FIG. 44, the proximal end (left end) of the first support member 4510 may be fixed to the outer surface of the intermediate member 4400, and the distal end (right end) of the first support member 4510 may be fixed to the inner surface of the movable member 4200.

Meanwhile, as described above, the movable member 4200 may be configured to move close to or away from the intermediate member 4400 in the longitudinal direction of the catheter body 4100 by means of the operating member 4300.

In particular, in the present disclosure, if the movable member 4200 moves to decrease the distance between the intermediate member 4400 and the movable member 4200, the first support member 4510 may be bent at least partially, and this bending portion may be configured to move away from the catheter body 4100. This will be described in more detail with reference to FIG. 45.

FIG. 45 a cross-sectional view schematically showing that the bending portion of the first support member 4510 moves away from the catheter body 4100 by the movement of the movable member 4200, in the configuration of FIG. 44.

Referring to FIG. 45, when the operating member 4300 is pulled in the left direction, the movable member 4200 moves in the left direction, as indicated by the arrow c41. At this time, since the operating member 4300 moves through the insert hole of the intermediate member 4400, the intermediate member 4400 does not move for a while in spite of the movement of the operating member 4300. Therefore, since the intermediate member 4400 is fixed and only the movable member 4200 moves toward the intermediate member 4400, the distance between the intermediate member 4400 and the movable member 4200 may decrease.

If so, distances between both ends of the first support member 4510 provided between the movable member 4200 and the intermediate member 4400 may decrease so that the first support member 4510 may be bent at least partially. In addition, if the movable member 4200 moves toward the intermediate member 4400 further, the bending portion of the first support member 4510 may be gradually away from the catheter body 4100. Here, as indicated by the arrow e4 in FIG. 45, the bending portion may be regarded as meaning an apex of the bending portion, namely a point of the bending portion of the first support member 4510 at which the degree of bending is greatest, or a point of the bending portion of the first support member 4510 which is located farthest from the central axis of the catheter body 4100. In addition, here, the bending portion moving away from the catheter body 4100 means that the bending direction of the bending portion is formed toward the outside of the catheter body 4100, so that the bending portion moves away from the central axis of the catheter body 4100.

The second support member 4520 may have a rod or plate shape extending in one direction, similar to the first support member 4510. However, the second support member 4520 may be connected between the catheter body 4100 and the intermediate member 4400. In other words, one end of the second support member 4520 is connected to the terminal 4110 of the catheter body, namely a farthest end of the distal end 4101 of the catheter body, and the other end thereof may be connected to the intermediate member 4400. For example, in the configuration of FIG. 44, the proximal end of the second support member 4520 may be fixed to the terminal 4110 of the catheter body outer surface, and the distal end of the second support member 4520 may be fixed to the inner surface of the intermediate member 4400.

Meanwhile, if the operating member 4300 keeps moving into the catheter body 4100 (in the left direction in FIG. 44) in a state in which the first stopper 4310 is hooked by the insert hole 4401 of the intermediate member 4400 as described above, the intermediate member 4400 may move into the catheter body 4100.

In particular, in the present disclosure, if the intermediate member 4400 moves to decrease the distance between the terminal 4110 of the catheter body and the intermediate member 4400, the second support member 4520 may be bent at least partially, and the bending portion may be configured to move away from the catheter body 4100. This will be described in more detail with reference to FIGS. 46 to 48.

FIG. 46 is a cross-sectional view schematically showing that the bending portion of the second support member 4520 moves away from the catheter body 4100 by the movement of an intermediate member 4400, in the configuration of FIG. 45. In addition, FIG. 47 is a perspective view of FIG. 46, and FIG. 48 is a front view of FIG. 47.

First, as shown in FIG. 45, if the first stopper 4310 is hooked by the intermediate member 4400 while the movable member 4200 is primarily moving in the left direction due to the movement of the operating member 4300 in the left direction, the intermediate member 4400 may secondarily move due to the movement of the operating member 4300. In other words, after the stopper is hooked by the intermediate member 4400, if the operating member 4300 keeps pulled to move in the left direction, the movable member 4200 moves in the left direction, and the intermediate member 4400 may also move in the left direction.

If the intermediate member 4400 moves toward the catheter body 4100 as indicated by the arrow c42 in FIG. 46, the distance between the intermediate member 4400 and the catheter body 4100 may decrease. If so, the distance between both ends of the second support member 4520 provided between the intermediate member 4400 and the catheter body 4100 decreases, and thus at least a partial portion of the second support member 4520 may be bent toward the outside of the catheter body 4100. In addition, if the intermediate member 4400 moves further toward the catheter body 4100, the bending portion of the second support member 4520 may gradually move away from the central axis of the catheter body 4100.

In the catheter of the present disclosure, since the first support member 4510 and the second support member 4520 should form bending portions according to the movement of the movable member 4200 and the intermediate member 4400, the first support member 4510 and the second support member 4520 may be made of material which may be bent when a distance between both ends thereof decreases. For example, the first support member 4510 and the second support member 4520 may be made of metal or polymer. However, the present disclosure is not limited to such specific materials of the support member.

Meanwhile, the electrodes 4600 may be provided at the bending portions e4 of the first support member 4510 and the second support member 4520. In particular, since the catheter according to the present disclosure includes the electrodes 4600 at the first support member 4510 and the second support member 4520, it is possible to provide a plurality of electrodes 4600.

The electrode 4600 may be connected to an energy supplying unit (not shown) through the lead wire 4700 to generate heat. In addition, the heat generated by the electrode 4600 may ablate surrounding tissues. For example, the electrode 4600 may ablate nerves around a blood vessel by generating heat of about 40° C. or above, preferably 40 to 80° C., and thus the nerves may be blocked. However, the temperature of the heat generated by the electrode 4600 may be set in various ways according to the use or purpose of the catheter.

The electrode 4600 may apply heat to nerve tissues around a blood vessel in contact with a wall of the blood vessel, and thus the electrode 4600 is preferably closely adhered to the wall of the blood vessel. Therefore, the electrode 4600 may have a curved shape, for example a circular, semicircular or oval shape, to conform to the shape of the inner wall of the blood vessel. In this embodiment, the electrode 4600 may be more clearly adhered to the wall of the blood vessel, and thus the heat generated by the electrode 4600 may be efficiently transferred to nerve tissues around the blood vessel.

Meanwhile, the electrode 4600 may be provided at a point of the bending portions of the first support member 4510 and the second support member 4520 which is farthest from the central axis of the catheter body 4100. In other words, if the distance between both ends decreases to form bending portions in the first support member 4510 and the second support member 4520, the electrode 4600 may be provided at an apex of the bending portion which is located farthest from the central axis of the catheter body 4100. In this embodiment, by protruding the electrode 4600 from the catheter body 4100 to the maximum, a contact force of the electrode 4600 to the wall of the blood vessel may be further improved.

The electrode 4600 may be made of material such as platinum or stainless steel, but the present disclosure is not limited to such specific materials of the electrode 4600. The electrode 4600 may be made of various materials in consideration of various factors such as a heat generation method and an operation target.

Preferably, the electrode 4600 may generate heat by means of radio frequency (RF). For example, the electrode 4600 may be connected to a high frequency generating unit through the lead wire 4700 and emits high frequency energy to ablate nerves.

Meanwhile, the electrode 4600 provided at the catheter may be a negative electrode, and a positive electrode corresponding to the negative electrode may be connected to an energy supplying unit such as a high frequency generating unit, similar to the negative electrode, and attached to a specific portion of a human body in the form or patch or the like.

Since the electrode 4600 is provided at the bending portions of the first support member 4510 and the second support member 4520, when the distance between both ends decreases, the electrode 4600 may move away from the central axis of the catheter body 4100.

For example, in the configuration depicted in FIG. 45, if the movable member 4200 moves along the arrow c41, the bending portion of the first support member 4510 gradually moves away from the central axis of the catheter body 4100, and the electrode 4600 provided at the bending portion of the first support member 4510 also moves in a direction away from the central axis of the catheter body 4100, as indicated by the arrows f41 and f42. On the contrary, if the movable member 4200 moves in a direction opposite to the arrow c41 of FIG. 45, the electrode 4600 provided at the bending portion of the first support member 4510 may be configured to move close to the central axis of the catheter body 4100 again.

In addition, in the configuration depicted in FIG. 46, if the intermediate member 4400 moves in the direction of c42, the bending portion of the second support member 4520 gradually moves away from the central axis of the catheter body 4100, and the electrode 4600 provided at the bending portion of the second support member 4520 also moves away from the central axis of the catheter body 4100, as indicated by the arrows f43 and f44. On the contrary, if the movable member 4200 moves in a direction opposite to the direction c42 of FIG. 46, the electrode 4600 provided at the bending portion of the second support member 4520 may be configured to move close to the central axis of the catheter body 4100 again.

Like this, according to the movement of the movable member 4200 or the intermediate member 4400, the electrode 4600 may move toward the outside of the catheter body 4100 or into the catheter body 4100, based on the central axis of the catheter body 4100 in the longitudinal direction.

For this, the first support member 4510 and/or the second support member 4520 having the electrode 4600 at the bending portion thereof to support the electrode 4600 may have suitable material or shape so that the bending direction of the bending portion may move farther from the central axis of the catheter body 4100 when the distance between both ends decreases.

For example, at least one of the first support member 4510 and the second support member 4520 may be configured so that an outer surface length of a section in the width direction is longer than an inner surface length thereof. This configuration will be described in more detail with reference to FIG. 49.

FIG. 49 is a schematic diagram showing arrangements and sections in the width direction of the first support member 4510 and the second support member 4520 according to an embodiment of the present disclosure. In FIG. 49, for convenience, the first support member 4510 and the second support member 4520 are shown on one plane, and other components than the catheter body 4100, the first support member 4510 and the second support member 4520 are not shown. In addition, a single support member is enlarged.

Referring to FIG. 49, in view of the section cut in the width direction, the first support member 4510 and the second support member 4520 may be configured so that an outer surface has a greater length than an inner surface. Here, the width direction means a direction orthogonal to the longitudinal direction of the catheter.

For illustration, an enlarged view showing the section of the second support member 4520 in the width direction is shown in a right portion of FIG. 49. Referring to the enlarged view, the length of the outer surface of the second support member 4520 means a length of a surface located far from the central axis of the catheter body 4100 as indicated by L41, and the length of the inner surface of the second support member 4520 means a length of a surface located close to the central axis of the catheter body 4100 as indicated by L42.

As seen from FIG. 49, the second support member 4520 is configured so that the length L41 of the outer surface is longer than the length L42 of the inner surface, and the first support member 4510 is also configured so that the length of the outer surface is longer than the length of the inner surface.

If the outer surface length of the first support member 4510 and the second support member 4520 is longer than the inner surface length as described above, when a force is applied to each support member in the longitudinal direction, each support member may be bent in a direction from the inner surface toward the outer surface. In other words, in this embodiment, when the movable member 4200 moves so that the distance between both ends of the first support member 4510 decreases and the intermediate member 4400 moves to decrease the distance between both ends of the second support member 4520, the first support member 4510 and the second support member 4520 may respectively have a bending direction moving away from the central axis of the catheter body 4100, as indicated by the arrows 141, 142, 143 and 144 in FIG. 49. Therefore, if the distance between the movable member 4200 and the intermediate member 4400 decreases and the distance between the intermediate member 4400 and the catheter body 4100 decreases, the electrode 4600 provided at the bending portions of the first support member 4510 and the second support member 4520 may move away from the catheter body 4100, as shown in FIGS. 46 and 47.

As another example, at least one of the first support member 4510 and the second support member 4520 may have a curved portion formed at least partially in a direction away from the central axis of the catheter body 4100. In other words, even in a state in which the distance between the movable member 4200 and the intermediate member 4400 is greatest, the first support member 4510 may not be perfectly flat but have a portion bent toward the outside of the central axis of the catheter body 4100. In addition, in a state in which the distance between the intermediate member 4400 and the terminal 4110 of the catheter body is greatest, the second support member 4520 may not be perfectly flat but have a portion bent toward the outside of the central axis of the catheter body 4100.

In this case, if the movable member 4200 and the intermediate member 4400 move to decrease the distance between both ends of the first support member 4510 and the second support member 4520, the degree of bending of the curved portions increases, which may form a bending portion, and the bending portion may have a bending direction toward the outside of the catheter body 4100. In addition, if the movable member 4200 and the intermediate member 4400 move further, the bending portion may gradually move away from the catheter body 4100.

As another example, at least one of the first support member 4510 and the second support member 4520 may be pre-shaped so that the bending portion does not move toward the central axis of the catheter body 4100 but moves away from the central axis of the catheter body 4100, when the distance between both ends decreases. For example, the first support member 4510 and the second support member 4520 may be pre-shaped to have the shape as shown in FIGS. 46 and 47 when the distance between both ends thereof decreases.

In this case, the first support member 4510 and the second support member 4520 may also be made of a shape memory alloy such as nitinol. In this embodiment, the first support member 4510 may be configured so that when the distance between the movable member 4200 and the intermediate member 4400 decreases, the bending portion moves away from the catheter body 4100 according to the memorized shape. In addition, the second support member 4520 may be configured so that when the distance between the intermediate member 4400 and the catheter body 4100 decreases, the bending portion moves away from the catheter body 4100 according to the memorized shape.

In addition, the bending portions of the first support member 4510 and the second support member 4520 may be provided by forming a notch at a predetermined portion thereof. In this case, if the distance between both ends of each support member decreases, a bending portion may be formed at a portion of the support member where the notch is formed. In this embodiment, by adjusting a direction of the notch, the bending portion may move away from the catheter body 4100 when the distance between both ends of the support member decreases.

As described above, in the catheter for denervation according to the present disclosure, the electrode 4600 is provided at the bending portions of the first support member 4510 and the second support member 4520 to move close to or away from the central axis of the catheter body 4100. Therefore, if the catheter according to the present disclosure is used to perform denervation, in a state in which the bending portions of the first support member 4510 and the second support member 4520 having the electrodes 4600 are close to the catheter body 4100, the distal end of the catheter, namely the catheter tip, may be moved to a target for operation through the blood vessel. In addition, if the catheter tip reaches the operation target, the bending portion of the first support member 4510 is primarily moved away from the catheter body 4100, and then the bending portion of the second support member 4520 is secondarily moved away from the catheter body 4100. By doing so, the plurality of electrodes 4600 provided at the bending portions of the first support member 4510 and the second support member 4520 may contact or approach the inner wall of the blood vessel. In addition, in this state, by emitting energy for generating heat, for example high frequency energy, through the electrode 4600, nerves around the blood vessel may be blocked. After that, if the denervation is completed with the energy emitted through the electrode 4600, the bending portions of the first support member 4510 and the second support member 4520 having the electrodes 4600 move again close to the catheter body 4100, and then the catheter may be extracted from the blood vessel or moved to another location.

Here, in a state in which the electrode 4600 moves away from the central axis of the catheter body 4100, the distance between the electrode 4600 and the central axis of the catheter body 4100 may be selected in various ways according to a size of an operation target, for example an inner diameter of the blood vessel. For example, in a state in which the electrode 4600 moves farthest away from the central axis of the catheter body 4100, a distance between each electrode 4600 and the central axis of the catheter body 4100 may be 2 mm to 4 mm.

Preferably, the first support member 4510 and/or the second support member 4520 may include a plurality of unit support members.

For example, as shown in the embodiment of FIG. 43, the first support member 4510 and the second support member 4520 may respectively include two unit support members. In addition, the first support member 4510 and the second support member 4520 may also include three or more unit support members, respectively.

If the first support member 4510 and the second support member 4520 include at least two unit support members as described above, the electrode 4600 may be provided at each unit support member. Therefore, more electrodes 4600 may be provided at the first support member 4510 and the second support member 4520, and the electrodes 4600 may be located at various positions. Therefore, in this embodiment, it is possible to prevent nerves from passing between the electrodes 4600, thereby improving the nerve blocking effect.

The lead wire 4700 is respectively electrically connected to the plurality of electrodes 4600 to give a power supply path to the plurality of electrodes 4600. In other words, the lead wire 4700 is connected between the electrode 4600 and the energy supplying unit so that the energy supplied from the energy supplying unit is transferred to the electrode 4600. For example, one end of the lead wire 4700 is connected to the high frequency generating unit and the other end thereof is connected to the electrode 4600 so that the energy generated by the high frequency generating unit is transferred to the electrode 4600, thereby allowing the electrode 4600 to generate heat by high frequency.

The lead wire 4700 may be attached to an upper or lower portion of the first support member 4510 or the second support member 4520 or provided in the first support member 4510 or the second support member 4520, between the terminal 4110 of the catheter body and the electrode 4600. In addition, the lead wire 4700 may not be fixed to the first support member 4510 or the second support member 4520 but connected to the electrode 4600 to be separated from the first support member 4510 or the second support member 4520.

Moreover, the lead wire 4700 may not be provided separate from the first support member 4510 or the second support member 4520 but implemented to be integrated with the support member. For example, at least a part of the first support member 4510 may be made of electrically conductive material, so that the first support member 4510 may serve as the lead wire 4700 in a region between intermediate member 4400 and the electrode 4600.

In the catheter of the present disclosure, the first support member 4510 and the second support member 4520 are arranged in order along the longitudinal direction of the catheter body 4100. For example, in the catheter according to the embodiment of FIG. 43, the catheter body 4100, the second support member 4520 and the first support member 4510 are arranged in order in a direction from the proximal end toward the distal end.

Since the first support member 4510 and the second support member 4520 are arranged in order along the longitudinal direction of the catheter body 4100 as described above, the electrode 4600 provided at the first support member 4510 and the electrode 4600 provided at the second support member 4520 may be disposed to be spaced apart from each other along the longitudinal direction of the catheter body 4100.

In particular, in a state in which the bending portions of the first support member 4510 and the second support member 4520 are located away from the catheter body 4100, the electrode 4600 provided at the first support member 4510 and the electrode 4600 provided at the second support member 4520 may be spaced apart from each other by a predetermined distance.

In more detail, in the embodiment of FIG. 46, in a state in which the first support member 4510 and the second support member 4520 are respectively bent toward the outside of the catheter body 4100, the electrode 4600 provided at the bending portion of the first support member 4510 and the electrode 4600 provided at the bending portion of the second support member 4520 may be spaced apart from each other by a predetermined distance in the longitudinal direction of the catheter body 4100, as indicated by d41.

In the present disclosure, since the electrode 4600 provided at the first support member 4510 and the electrode 4600 provided at the second support member 4520 are spaced apart from each other by a predetermined distance as described above, it is possible to prevent stenosis from occurring. If the plurality of electrodes 4600 respectively emits heat, heated portions of the blood vessel may swell toward the inside of the blood vessel. At this time, in the catheter of the present disclosure, since at least two electrodes 4600 are spaced apart from each other by a predetermined distance in the longitudinal direction of the catheter body 4100, the heated portions of the blood vessel are spaced apart from each other by a predetermined distance in the longitudinal direction of the blood vessel. Therefore, in the present disclosure, it is possible to prevent stenosis from occurring.

Here, the distance between the electrode 4600 provided at the first support member 4510 and the electrode 4600 provided at the second support member 4520 in the longitudinal direction of the catheter body 4100 as indicated by d41 may be variously selected depending on a size of the catheter or an operation target. For example, the catheter may be configured so that in a state in which the electrode 4600 provided at the first support member 4510 and the electrode 4600 provided at the second support member 4520 are far from the catheter body 4100, the distance between the electrodes 4600 in the longitudinal direction of the catheter body 4100 is 0.3 to 0.8 cm. In this embodiment, it is possible to prevent stenosis of the blood vessel and minimize the problem that nerves around the blood vessel pass between the electrodes 4600 and are not ablated by the electrodes 4600.

Meanwhile, if a plurality of electrodes 4600 is provided at the first support member 4510 or the second support member 4520, the plurality of electrodes 4600 provided at the first support member 4510 or the plurality of electrodes 4600 provided at the second support member 4520 may also be spaced apart from each other by a predetermined distance. For example, even though two electrodes 4600 provided at the first support member 4510 have no difference in distance along the longitudinal direction of the catheter body 4100 in the configuration depicted in FIG. 46, the two electrodes 4600 may also be configured to have different distances.

Preferably, in the present disclosure, the plurality of electrodes 4600 may be configured to be spaced apart from each other by a predetermined angle based on the central axis of the catheter body 4100 in the longitudinal direction, in a state in which the bending portions of the first support member 4510 and the second support member 4520 are far from the central axis of the catheter body 4100 in the longitudinal direction.

For example, as shown in FIG. 48, in a state in which the electrodes 4600 provided at the first support member 4510 and the second support member 4520 move away from the catheter body 4100, assuming that angles among four electrodes 4600 are g41, g42, g43 and g44 based on the central axis o4 of the catheter, g41, g42, g43 and g44 have predetermined angles, so that the four electrodes 4600 are spaced apart from each other by the predetermined angles. For example, g41, g42, g43 and g44 may be identically 90°

In the embodiment in which the electrodes 4600 are spaced apart from each other by predetermined angles based on the central axis o4 of the catheter body 4100 as described above, the electrodes 4600 may be configured to spread widely in all directions around the catheter body 4100. Therefore, even though nerves are disposed in a local portion of the blood vessel, the electrodes 4600 may cover the nerves to the maximum.

FIG. 50 is a cross-sectional view schematically showing a distal end of a catheter for denervation according to another embodiment of the present disclosure, and FIG. 51 is a cross-sectional view schematically showing that an electrode 4600 moves away from the catheter body 4100 by the movement of the movable member 4200 and the intermediate member 4400, in the configuration of FIG. 50.

Referring to FIGS. 50 and 51, the catheter for denervation according to the present disclosure may include a second stopper 4320.

The second stopper 4320 may prevent the distance between the intermediate member 4400 and the catheter body 4100 from decreasing below a predetermined level. For this, the second stopper 4320 may be provided at a portion of the operating member 4300 located between the intermediate member 4400 and the terminal 4110 of the catheter body. In this case, the second stopper 4320 may be hooked by the operation hole 4120 of the catheter body 4100 through which the operating member 4300 is inserted.

In more detail, in the catheter according to the embodiment of FIG. 50, if an operator pulls the operating member 4300 to the left, at first, the intermediate member 4400 is fixed, and the movable member 4200 moves in the left direction, by which the first support member 4510 may bend since the distance between both ends thereof decreases. And then, if the first stopper 4310 is hooked by the insert hole 4401 of the intermediate member 4400, the intermediate member 4400 starts moving in the left direction. If so, the distance between the intermediate member 4400 and the terminal 4110 of the catheter body decreases, by which the second support member 4520 may bent since the distance between both ends thereof decreases. After that, if the second stopper 4320 is hooked by the operation hole 4120 of the catheter body 4100 as shown in FIG. 51, the intermediate member 4400 does not move in the left direction any more, and thus the operator cannot pull the operating member 4300 in the left direction any more.

In the embodiment including the second stopper 4320 as described above, it is possible to facilitate an operator's manipulation and also prevent various components included in the catheter from being damaged. For example, in the embodiment of FIG. 51, the second stopper 4320 may limit the intermediate member 4400 not to move further in the left direction, thereby preventing the intermediate member 4400 from moving excessively close to the catheter body 4100 and thus damaging the second support member 4520 or cutting the connection between the second support member 4520 and the catheter body 4100 or the connection between the second support member 4520 and the intermediate member 4400. Moreover, an operator may not pay attention to an operating distance of the operating member 4300 since the operating distance is limited by the first stopper 4310 and the second stopper 4320 while the operating member 4300 is pushed or pulled.

In addition, the catheter for denervation according to the present disclosure may include a reinforcing member 4800, as shown in FIG. 50.

The reinforcing member 4800 may have a rod or plate shape extending in the longitudinal direction of the catheter body 4100 and be provided between the catheter body 4100 and the movable member 4200. In addition, a distal end of the reinforcing member 4800 may be connected and fixed to the movable member 4200 to be movable according to the movement of the movable member 4200.

At this time, a first through hole 4130 and a second through hole 4402 may be respectively formed in the catheter body 4100 and the intermediate member 4400, and the reinforcing member 4800 may be inserted through the through holes 4130, 4402.

In this embodiment, as shown in FIG. 51, if the movable member 4200 moves in the left direction, the reinforcing member 4800 may also move in the left direction. At this time, the reinforcing member 4800 is inserted into the first through hole 4130 of the catheter body 4100 and the second through hole 4402 of the intermediate member 4400, so that the reinforcing member 4800 may slide through the through holes 4130, 4402 according to the movement of the movable member 4200.

In this embodiment, the connections among the catheter body 4100, the intermediate member 4400 and the movable member 4200 may be supported more strongly by the reinforcing member 4800. In other words, if the movable member 4200 and the intermediate member 4400 are separated from the catheter body 4100 as in this embodiment, in case of connecting the catheter body 4100, the intermediate member 4400 and the movable member 4200 by using a single operating member 4300, the connection state and supporting force among the catheter body 4100, the intermediate member 4400 and the movable member 4200 may be weak. However, if the reinforcing member 4800 is provided separately from the operating member 4300 as in this embodiment, the supporting force to the movable member 4200 and the intermediate member 4400 separated from the catheter body 4100 is more reinforced, and the connection state among the catheter body 4100, the intermediate member 4400 and the movable member 4200 may be more firmly maintained. In addition, since the reinforcing member 4800 may guide movement of the movable member 4200 and the intermediate member 4400, the moving direction of the movable member 4200 and the intermediate member 4400 may be appropriately kept without deviating from the central axis of the catheter body 4100.

Meanwhile, in the embodiment including the reinforcing member 4800, the first stopper 4310 and/or the second stopper 4320 may be provided at the reinforcing member 4800. In other words, the first stopper 4310 and/or the second stopper 4320 may not be provided at the operating member 4300 but provided at the reinforcing member 4800, or the first stopper 4310 and/or the second stopper 4320 may be provided at both the operating member 4300 and the reinforcing member 4800.

In addition, even though the embodiment of FIGS. 50 and 51 illustrates that a single reinforcing member 4800 is provided, two or more reinforcing members 4800 may also be provided.

Moreover, even though it is depicted in several drawings that only one operating member 4300 is provided, two or more operating members 4300 may also be provided.

FIG. 52 is a cross-sectional view schematically showing a distal end of a catheter for denervation according to another embodiment of the present disclosure, and FIG. 53 is a cross-sectional view schematically showing that an electrode 4600 moves away from the catheter body 4100 by the movement of the movable member 4200 and the intermediate member 4400, in the configuration of FIG. 52.

Referring to FIGS. 52 and 53, the catheter body 4100 may have a guide hole 4140 formed in the distal end thereof so that a guide wire W4 may pass through. Here, the guide wire W4 is to guide the catheter to an operation target and may reach the operation target prior to the catheter. In this embodiment, the guide wire W4 may be inserted into the catheter through the guide hole 4140, and the catheter tip may reach the operation target along the guide wire W4.

The catheter body 4100 may have one or more guide hole 4140. For example, as shown in FIGS. 52 and 53, the catheter body 4100 has a first guide hole 4141 formed at the terminal thereof and a second guide hole 4142 formed at a position spaced apart from the terminal 4110 of the catheter body by a predetermined distance. In this case, the guide wire W4 may be inserted into the inner space of the catheter body 4100 through the first guide hole 4141 and then drawn out of the catheter body 4100 through the second guide hole 4142. However, the second guide hole 4142 may not be provided, and in this case, the guide wire W4 inserted into the inner space of the catheter body 4100 through the first guide hole 4141 may extend long along the inner space of the catheter body 4100 and then be drawn out of the catheter body 4100 at the proximal end of the catheter body 4100.

If the second guide hole 4142 is provided, the second guide hole may be located at various positions depending on various situations. In particular, the second guide hole 4142 may be formed at a point spaced apart by 10 cm to 15 cm from the terminal 4110 of the catheter body in the longitudinal direction of the catheter body. Even though FIG. 52 shows that the second guide hole 4142 is located close to the terminal 4110 of the catheter body, it is just for illustration, and the distance from the terminal of the catheter body to the second guide hole, indicated by L43, may be 10 cm to 15 cm. In this embodiment, while the catheter body is moving, it is possible to prevent the problem that the guide wire drawn from the catheter body through the second guide hole is entangled with the catheter body, thereby facilitating smooth movement of the catheter body. However, the present disclosure is not limited to such a location of the second guide hole.

Meanwhile, in this embodiment, a guide hole 4210 may be formed in the movable member 4200 so that a guide wire W4 may pass through, and a guide hole 4403 may also be formed in the intermediate member 4400 so that a guide wire W4 may pass through In an embodiment in which the guide hole 4140 is formed in the catheter body 4100 as described above, since the guide wire W4 inserted into the guide hole 4140 guides movement of the catheter tip, the catheter may smoothly reach an operation target, and the catheter may be easily manipulated. Moreover, since the catheter does not need to include a component for adjusting a moving direction of the catheter, the catheter may have a simpler structure, which is advantageous in reducing the size of the catheter.

Also preferably, the catheter for denervation according to the present disclosure may further include an elastic member 4900.

One end of the elastic member 4900 may be connected to the intermediate member 4400 to give a restoring force when the intermediate member 4400 is moving. For example, as shown in FIG. 52, the elastic member 4900 may be connected between the terminal 4110 of the catheter body and the intermediate member 4400. In this case, as shown in FIG. 53, if the operating member 4300 is continuously pulled in the left direction after the first stopper 4310 is hooked by the insert hole of the intermediate member 4400, the intermediate member 4400 moves in the left direction. In this case, the restoring force, namely the elastic restoring force, of the elastic member 4900 is applied in the right direction. Therefore, after nerves are completely blocked by the electrode 4600, the intermediate member 4400 should move again in the right direction and return to its original state as shown in FIG. 52. Here, the movement of the intermediate member 4400 in the right direction may be more easily performed by means of the restoring force of the elastic member 4900. Therefore, after nerves are blocked by the electrode 4600, an operator may not give great efforts to move the electrode 4600 close to the central axis of the catheter body 4100.

In addition, in an embodiment in which the elastic member 4900 is provided as described above, it is possible to prevent the electrode 4600 from deviating from the central axis of the catheter body 4100 while the catheter tip is moving, and thus it is also possible to prevent the blood vessel from being damaged due to protrusion of the electrode 4600 and facilitate easy movement of the catheter tip. Moreover, even though the second stopper 4320 is not provided, the moving distance of the intermediate member 4400 may be limited by the elastic member 4900, which may prevent various components from being damaged due to excessive movement of the intermediate member 4400.

Further, if the elastic member 4900 is provided between the terminal 4110 of the catheter body and the intermediate member 4400 as in this embodiment, while the movable member 4200 is moving to bend the first support member 4510, it is possible to prevent the intermediate member 4400 from being pushed toward the terminal 4110 of the catheter body. Therefore, it is possible to prevent the problem that the first support member 4510 is incompletely bent since the intermediate member 4400 moves before the first support member 4510 is completely bent.

In addition, even through the elastic member 4900 is provided between the intermediate member 4400 and the catheter body 4100 in the configuration depicted in FIGS. 52 and 53, the elastic member 4900 may also be provided between the intermediate member 4400 and the movable member 4200. Moreover, at least two elastic members 4900 may also be provided at different locations of the catheter.

Meanwhile, even though various embodiments illustrate that only a single intermediate member 4400 is provided between the movable member 4200 and the terminal 4110 of the catheter body, two or more intermediate members 4400 may also be provided between them.

FIG. 54 is a cross-sectional view schematically showing a distal end of a catheter for denervation according to another embodiment of the present disclosure.

Referring to FIG. 54, the intermediate member 4400 may include a plurality of unit intermediate members. Here, the unit intermediate member represents an individual unit intermediate member in case a plurality of intermediate members 4400 is provided. FIG. 54 shows that the intermediate member 4400 is composed of two unit intermediate members. Here, the unit intermediate member at the right portion of FIG. 54 is called a first unit intermediate member 4410, and the unit intermediate member at the left portion is called a second unit intermediate member 4420.

In this configuration, the first unit intermediate member 4410 may be connected to the proximal end of the first support member 4510, and the second unit intermediate member 4420 may be connected to the distal end of the second support member 4520.

In the embodiment in which the intermediate member 4400 includes a plurality of unit intermediate members as described above, the catheter may include a separate support member in addition to the first support member 4510 and the second support member 4520.

For example, the catheter may include a third support member 4530 between the first unit intermediate member 4410 and the second unit intermediate member 4420. The distal end of the third support member 4530 may be connected and fixed to the first unit intermediate member 4410, and the proximal end thereof may be connected and fixed to the second unit intermediate member 4420.

The third support member 4530 may be configured to have a shape similar to the first support member 4510 and the second support member 4520, even though its location is different from them. For example, the third support member 4530 may be configured so that at least a partial portion thereof is bent when the distance of both ends thereof decreases. At this time, the bending direction may be formed toward the outside of the catheter body 4100, so that the bending portion gradually moves away from the central axis of the catheter body 4100 when the distance of both ends thereof decreases. In addition, the third support member 4530 may have an electrode 4600 at the bending portion.

Moreover, in an embodiment including a plurality of unit intermediate members at the intermediate member 4400, a stopper may be further included in addition to the first stopper 4310.

For example, as shown in FIG. 54, the catheter may further include a third stopper 4330 in order to move the second unit intermediate member 4420. Here, the third stopper 4330 may be provided at a predetermined location of the operating member 4300 between the first unit intermediate member 4410 and the second unit intermediate member 4420.

In this embodiment, if an operator pulls the operating member 4300, first, the movable member 4200 moves so that the distance between the first unit intermediate member 4410 and the movable member 4200 decreases, thereby bending the first support member 4510. After that, if the first stopper 4310 is hooked by the insert hole 4401 of the first unit intermediate member 4410, the first unit intermediate member 4410 starts moving so that the distance between the first unit intermediate member 4410 and the second unit intermediate member 4420 decreases, thereby bending the third support member 4530. After that, if the third stopper 4330 is hooked by the insert hole 4401 of the second unit intermediate member 4420, the second unit intermediate member 4420 starts moving so that the distance between the second unit intermediate member 4420 and the catheter body 4100 decreases, thereby bending the second support member 4520.

In other words, in this embodiment, if an operator pulls the operating member 4300, the first support member 4510 may be primarily bent, the third support member 4530 may be secondarily bent, and the second support member may be thirdly bent.

In the embodiment in which a plurality of intermediate members 4400 is included between the movable member 4200 and the terminal 4110 of the catheter body as described above, the plurality of electrodes 4600 may be arranged in several stages to be spaced apart from each other by a predetermined distance in the longitudinal direction of the catheter body 4100. In addition, the electrodes 4600 may be arranged at more angles based on the central axis of the catheter body 4100. For example, in the embodiment of FIG. 54, based on the central axis o4 of the catheter body, six electrodes 4600 provided at the first support member 4510, the second support member 4520 and the third support member 4530 may be arranged to widely spread with an angle of 60° to adjacent electrodes. In this embodiment, it is possible to further improve the nerve blocking effect by the electrodes 4600.

Also preferably, the catheter for denervation according to the present disclosure may further include a temperature measuring member (not shown).

In particular, the temperature measuring member may be provided around the electrode 4600 to measure a temperature of the electrode 4600 or around the electrode 4600. In addition, the temperature measured by the temperature measuring member as described above may be used for controlling the temperature of the electrode 4600. Here, the temperature measuring member may be connected to the lead wire 4700 through a separate wire, and the separate wire may extend to the proximal end of the catheter body 4100 through the inner space of the catheter body 4100 and be drawn out of the catheter body 4100.

Meanwhile, even though various embodiments illustrate that the movable member 4200 is provided out of the catheter body 4100, the present disclosure is not limited thereto.

FIG. 55 is a cross-sectional view schematically showing a distal end of a catheter for denervation according to another embodiment of the present disclosure, and FIG. 56 is a cross-sectional view showing the catheter of FIG. 55 along the longitudinal direction. However, features to which the description in relation to the embodiment of FIGS. 43 to 54 can be applied will not be described in detail, but different features will be described in detail.

Referring to FIGS. 55 and 56, the movable member 4200 and the intermediate member 4400 may be provided in the inner space of the catheter body 4100. In addition, the movable member 4200 and intermediate member 4400 may move in the lateral direction in the inner space of the catheter body 4100.

In addition, the movable member 4200 may be located close to the proximal end of the catheter (in the left direction in FIG. 56) in comparison to the intermediate member 4400, and the operating member 4300 may be connected and fixed to the movable member 4200.

Here, the proximal end of the first support member 4510 may be connected and fixed to the movable member 4200, and the distal end thereof may be connected and fixed to the intermediate member 4400. In addition, the proximal end of the second support member 4520 may be connected and fixed to the intermediate member 4400, and the distal end thereof may be connected and fixed to the terminal 4110 of the catheter body.

Moreover, the first support member 4510 and the second support member 4520 may be bent toward the outside of the catheter body 4100 when the distance between both ends thereof decreases, similar to the former embodiments, so that the electrodes 4600 provided at the bending portions move away from the catheter body 4100.

Meanwhile, the first stopper 4310 may be provided to protrude toward the movable member 4200 on at least a partial portion of the intermediate member 4400 as shown in FIGS. 55 and 56 in order to limit the distance between the movable member 4200 and the intermediate member 4400 and also allow the intermediate member 4400 to move according to the operation of the operating member 4300. In another case, the first stopper 4310 may also be provided to protrude toward the intermediate member 4400 on at least a partial portion of the movable member 4200.

In this embodiment, since the movable member 4200 is located closer to the proximal end of the catheter in comparison to the intermediate member 4400, if an operator pushes the operating member 4300, the movable member 4200 may move in the right direction of FIG. 56.

FIG. 57 is a cross-sectional view schematically showing that the movable member 4200 moves in the right direction, in the configuration of FIG. 56.

Referring to FIG. 57, if the movable member 4200 moves in the right direction, since the intermediate member 4400 does not move at an initial stage, the distance between the movable member 4200 and the intermediate member 4400 decreases. Therefore, the first support member 4510 may be bent toward the outside of the catheter body 4100, and thus the electrode 4600 provided at the bending portion of the first support member 4510 may move away from the central axis of the catheter body 4100.

After that, if the movable member 4200 reaches the first stopper 4310, the distance between the movable member 4200 and the intermediate member 4400 does not decrease any more due to the first stopper 4310. In addition, if the operator keeps pushing the operating member 4300, the intermediate member 4400 may move in the right direction of FIG. 57.

FIG. 58 is a cross-sectional view schematically showing that the intermediate member 4400 moves in the right direction, in the configuration of FIG. 57, and FIG. 59 is a perspective view of FIG. 58.

Referring to FIGS. 58 and 59, if the intermediate member 4400 moves in the right direction, the distance between the terminal 4110 of the catheter body and the intermediate member 4400 decreases. Therefore, the second support member 4520 may be bent toward the outside of the catheter body 4100, and thus the electrode 4600 provided at the bending portion of the second support member 4520 may move away from the central axis of the catheter body 4100.

In addition, in the embodiment of FIGS. 55 to 59, the first support member 4510 and the second support member 4520, including the plurality of electrodes 4600 provided at these support member, located in the inner space of the catheter body 4100 may protrude toward the outside of the catheter body 4100 according to the movement of the movable member 4200 and the intermediate member 4400. For this, the catheter body 4100 may have an opening 4150 through which the first support member 4510 and the second support member 4520 as well as the electrodes 4600 protrude to the outside. In other words, if the movable member 4200 and the intermediate member 4400 move so that the distance between both ends of the first support member 4510 or the second support member 4520 decreases, the bending portion of the first support member 4510 or the second support member 4520 as well as the electrode 4600 may be drawn out of the catheter body 4100 through the opening 4150 of the catheter body 4100. Meanwhile, if the movable member 4200 and the intermediate member 4400 move so that the distance between both ends of the first support member 4510 or the second support member 4520 increases, the bending portion of the first support member 4510 or the second support member 4520 as well as the electrode 4600 may be inserted into the inner space of the catheter body 4100 through the opening 4150 of the catheter body 4100.

Meanwhile, the features of the embodiment of FIGS. 43 to 54 may also be applied to the catheter according to the embodiment of FIGS. 55 to 59.

For example, in the embodiment of FIGS. 55 to 59, the plurality of electrodes 4600 may be spaced apart from each other by a predetermined angle based on the central axis of the catheter body 4100 in the longitudinal direction, in a state in which the bending portions of the first support member 4510 and the second support member 4520 are far from the catheter body 4100.

In addition, in the embodiment of FIGS. 55 to 59, a plurality of intermediate members 4400 may be provided, and a second stopper 4320 or an elastic member 4900 may be further included. In particularly, the second stopper 4320 may be provided between the intermediate member 4400 and the terminal 4110 of the catheter body to limit the distance between the intermediate member 4400 and the terminal 4110 of the catheter body.

FIG. 60 is a perspective view schematically showing a distal end of a catheter for denervation according to another embodiment of the present disclosure.

Referring to FIG. 60, the catheter for denervation according to the present disclosure may further include an end tip 4950.

The end tip 4950 is provided at the front surfaces of the distal ends of the catheter body 4100 and the movable member 4200. For example, if the movable member is located closer to the distal end in comparison to the catheter body as in the embodiment of FIG. 60, the end tip 4950 may be provided at the front surface of the distal end of the movable member. However, if the terminal of the catheter body is located closer to the distal end in comparison to the movable member as in the embodiment of FIG. 55, the end tip 4950 may be provided at the front surface of the distal end of the catheter body. In other words, the end tip 4950 may be regarded as being located farther from the terminal of the catheter body and the movable member. In this case, the end tip 4950 may be a component serving as the terminal of the catheter for denervation according to the present disclosure.

Meanwhile, the end tip 4950 may be configured to be separated from the movable member or the catheter body. For example, in the configuration of FIG. 60, the end tip 4950 may be separated from the movable member. In this case, if the operating member operates to move the movable member, the end tip 4950 does not move, and the distance between the movable member and the end tip 4950 may change. However, the end tip 4950 may also be fixed to the movable member or the catheter body.

The end tip 4950 may be made of soft and flexible material. In particular, the end tip 4950 may be made of a composition containing polyether block amide (PEBA). Here, the composition for the end tip 4950 may contain other additives in addition to the polyether block amide. For example, the end tip 4950 may be made of a composition containing 70 weight % of polyether block amide and 30 weight % of barium sulfate, based on the entire weight of the composition.

In this configuration of the present disclosure, when the distal end 4101 of the catheter body moves along a blood vessel or the like, the end tip 4950 made of soft and flexible material is located at a foremost position, which may reduce damages to the blood vessel and facilitate easier change of a moving direction. Further, the end tip 4950 made of the above material may be photographed by X-ray, and thus a location of the distal end of the catheter body may be easily figured out.

Preferably, the end tip 4950 may have a hollow tube shape. In addition, the hollow of the end tip 4950 may extend in the same direction of the longitudinal direction of the catheter body. If the end tip 4950 has a tube shape as described above, a guide wire may pass through the hollow of the end tip 4950. For example, the end tip may have a tube shape with a length of 6 mm and a hollow diameter of 0.7 mm.

The end tip may extend along the longitudinal direction of the catheter body. At this time, the end tip may have different sizes along the length thereof. In particular, if the end tip has a cylindrical shape, a distal end of the end tip may have the smallest diameter in comparison to other regions. For example, the distal end of the end tip may have a smallest diameter of 1.1 mm, when the thickest region of the end tip has a diameter of 1.3 mm.

The end tip 4950 may have a suitable length, which is not too long and not too short. For example, in the configuration of FIG. 60, the length of the end tip 4950, indicated by L44, may be 5 mm to 15 mm. In this configuration, when the catheter moves along the inner space of a blood vessel or the inner space of a sheath, it is possible to prevent the movement from being disturbed by the end tip 4950. In addition, in this configuration, a shape of the blood vessel or the like at which the end tip 4950 is located may be easily figured out from a bending shape or a bending direction of the end tip 4950.

In addition, the catheter for denervation according to the present disclosure may further include a passing tube (not shown). The passing tube may have a hollow tube shape, which is included in the inner space of the catheter body, and the operating member may be located in the hollow of the passing tube. In other words, the operating member may move in a state of being inserted into the inner space of the passing tube. In this case, the passing tube may be exposed not only to the inner space of the catheter body but also to the outside. For example, in the configuration of FIG. 60, the passing tube may be provided in a space between the catheter body and the movable member. In addition, the movable member may have a ring shape which is movable while surrounding the outer circumference of the passing tube. In this configuration, a moving path of the movable member may be fixed, and a coupling force between the catheter body and the movable member may be further reinforced.

Meanwhile, even though the drawings for illustrating the above embodiments depict that two first support members 4510 and two second support members 4520 are used, the present disclosure is not limited to such a specific number of support members. In other words, the number of first support members 4510 and second support members 4520 may be three or more and may also be different from each other.

For example, two first support members 4510 and four second support members 4520 may be provided. In particular, in the configuration depicted in FIG. 43, if the number of second support members 4520 is greater than the number of first support members 4510, when an operator pulls the operating member 4300, it is possible to prevent the phenomenon that the intermediate member 4400 moves to bend the second support member 4520 before the first support member 4510 is completely bent.

In addition, event though the various embodiments illustrate that one electrode 4600 is provided at each unit support member included in the first support member 4510 and the second support member 4520, it is possible that two or more electrodes 4600 are provided at each unit support member, and it is also possible that no electrode is provided at some unit support members.

A denervation apparatus according to the present disclosure includes the catheter for denervation. In addition, the denervation apparatus may further include an energy supplying unit and an opponent electrode in addition to the catheter for denervation. Here, the energy supplying unit may be electrically connected to the electrode 4600 through the lead wire 4700. In addition, the opponent electrode may be electrically connected to the energy supplying unit through a lead wire 4700 which is different from the above lead wire 4700. In this case, the energy supplying unit may supply energy to the electrode 4600 of the catheter in the form of high frequency or the like, and the electrode 4600 of the catheter generates heat to ablate nerves around the blood vessel, thereby block the nerves.

The present disclosure has been described in detail. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

In addition, even though terms representing directions such as proximal, distal, upper, lower, right, left or the like have been used in the specification, the terms are just used to indicate relative locations for convenience and can be replaced with other words according to an observation point of an observer or an arrangement of a component, as obvious to those having ordinary skill in the art.

What is claimed is:

1. A catheter for denervation, comprising:
  a catheter body extending in one direction to have a proximal end and a distal end and having an inner space formed along a longitudinal direction thereof;
  a movable member provided at the distal end of the catheter body to be movable along the longitudinal direction of the catheter body;
  an operating member having a distal end connected to the movable member to move the movable member;
  a plurality of support members having one end connected and fixed to a terminal of the catheter body and another end connected and fixed to the movable member, wherein when the movable member moves to decrease a distance between the terminal of the catheter body and the movable member, at least a partial portion of the plurality of support members is bent so that the bending portion moves away from the catheter body;
  a plurality of electrodes respectively provided at the bending portion of the plurality of support members to generate heat; and
  a lead wire respectively electrically connected to the plurality of electrodes to give a power supply path for the plurality of electrodes,
  wherein at least one of the catheter body and the movable member is connected and fixed to at least two of the plurality of support members at points which are spaced apart from each other by a predetermined distance in the longitudinal direction of the catheter body,
  wherein at least one of the catheter body and the movable member has stepped surfaces to which the plurality of support members are connected and fixed,
  wherein at least two of the plurality of support members are connected and fixed to different stepped surfaces of the at least one of the catheter body and the movable member such
    that connection points of the at least two of the plurality of support members with respect to the catheter body are spaced apart from each other by a predetermined distance in the longitudinal direction of the catheter body, and/or
    that connection points of the at least two of the plurality of support members with respect to the movable member are spaced apart from each other by a predetermined distance in the longitudinal direction of the catheter body.

2. The catheter for denervation according to claim 1, wherein the movable member is located outside the catheter body.

3. The catheter for denervation according to claim 2, further comprising a reinforcing member extending in the longitudinal direction of the catheter body and provided between the catheter body and the movable member,
  wherein a distal end of the reinforcing member is fixed to the movable member and a proximal end of the reinforcing member is inserted into a through hole of the catheter body, so that the proximal end of the reinforcing member moves through the through hole of the catheter body according to movement of the movable member.

4. The catheter for denervation according to claim 1, wherein the movable member is located within the catheter body, and wherein the catheter body has an opening through which the bending portion of the support member is drawn out of the catheter body when the support member is bent.

5. The catheter for denervation according to claim 1, wherein in a state in which the bending portion of the support member moves away from the catheter body, the plurality of electrodes is spaced apart from each other by a predetermined distance in the longitudinal direction of the catheter body.

6. The catheter for denervation according to claim 5, wherein the predetermined distance is 0.3 cm to 0.8 cm in the longitudinal direction of the catheter body.

7. The catheter for denervation according to claim 5, wherein at least one of the plurality of support members has a curved portion to define the bending portion according to movement of the movable member.

8. The catheter for denervation according to claim 5, wherein at least one of the plurality of support members is pre-shaped to define the bending portion according to movement of the movable member.

9. The catheter for denervation according to claim 1, wherein in a state in which the bending portion of the support member moves away from the catheter body, the plurality of electrodes is spaced apart from each other by a predetermined angle based on a central axis of the catheter body in the longitudinal direction.

10. The catheter for denervation according to claim 1, wherein surfaces of the catheter body and the movable member connected to the plurality of support members are perpendicular to the longitudinal direction of the catheter body.

11. The catheter for denervation according to claim 1, wherein the plurality of electrodes is configured to generate heat by means of radio frequency.

12. The catheter for denervation according to claim 1, wherein the catheter body has a guide hole formed in the distal end thereof so that a guide wire moves therethrough.

13. The catheter for denervation according to claim 1, further comprising at least one stopper for limiting a moving distance of the movable member.

14. The catheter for denervation according to claim 13, wherein the at least one stopper is fixed to the operating member.

15. The catheter for denervation according to claim 13, wherein the at least one stopper is fixed to the catheter body.

16. The catheter for denervation according to claim 1, further comprising an elastic member connected to the movable member to give a restoring force with respect to movement of the movable member.

17. The catheter for denervation according to claim 1, further comprising an end tip made of a composition containing polyether block amide and located at a front surface of the distal end of the catheter body and the movable member.

18. The catheter for denervation according to claim 1 wherein a surface of the catheter body and a surface of the movable member, which are connected to the support member, are matched with each other.

19. The catheter for denervation according to claim 1, wherein a section of the plurality of support members in a width direction has an outer surface length longer than an inner surface length thereof.

20. A denervation apparatus, comprising:
the catheter defined in claim 1; and
a power supply connected to the catheter.

* * * * *